(12) United States Patent
Baker et al.

(10) Patent No.: US 11,191,875 B2
(45) Date of Patent: Dec. 7, 2021

(54) SALIVARY TISSUE REGENERATION USING LAMININ PEPTIDE-MODIFIED HYDROGELS

(71) Applicants: UNIVERSITY OF UTAH RESEARCH FOUNDATION, Salt Lake City, UT (US); UNIVERSITY AT BUFFALO, Amherst, NY (US)

(72) Inventors: Olga Baker, Salt Lake City, UT (US); Kihoon Nam, Salt Lake City, UT (US); Pedro Lei, Salt Lake City, UT (US); Stelios Andreadis, Salt Lake City, UT (US)

(73) Assignees: UNIVERSITY OF UTAH RESEARCH FOUNDATION, Salt Lake City, UT (US); UNIVERSITY AT BUFFALO, Amherst, NY (US)

( * ) Notice: Subject to any disclaimer, the term of this patent is extended or adjusted under 35 U.S.C. 154(b) by 0 days.

(21) Appl. No.: 16/326,326

(22) PCT Filed: Sep. 19, 2017

(86) PCT No.: PCT/US2017/052174
§ 371 (c)(1),
(2) Date: Feb. 18, 2019

(87) PCT Pub. No.: WO2018/053470
PCT Pub. Date: Mar. 22, 2018

(65) Prior Publication Data
US 2019/0192739 A1     Jun. 27, 2019

Related U.S. Application Data
(60) Provisional application No. 62/396,470, filed on Sep. 19, 2016.

(51) Int. Cl.
| | | |
|---|---|---|
| C07K 14/78 | (2006.01) | |
| A61L 27/52 | (2006.01) | |
| A61K 47/64 | (2017.01) | |
| C07K 14/75 | (2006.01) | |
| A61L 27/22 | (2006.01) | |
| C07K 19/00 | (2006.01) | |

(52) U.S. Cl.
CPC .............. *A61L 27/52* (2013.01); *A61K 47/64* (2017.08); *A61L 27/225* (2013.01); *C07K 14/75* (2013.01); *C07K 14/78* (2013.01); *C07K 19/00* (2013.01); *A61L 2430/22* (2013.01); *A61L 2430/40* (2013.01); *C07K 2319/50* (2013.01); *C07K 2319/60* (2013.01)

(58) Field of Classification Search
None
See application file for complete search history.

(56) References Cited

U.S. PATENT DOCUMENTS
| | | | |
|---|---|---|---|
| 4,563,304 A | 1/1986 | Carlsson et al. | |
| 2010/0184183 A1* | 7/2010 | Schussler | A61L 27/24 435/177 |

OTHER PUBLICATIONS

Meinhart et al. ('Enhanced endothelial cell retention on shear-stressed synthetic vascular grafts precoated with RGD-cross-linked fibrin' Tissue Engineering v11(5/6) 2005 pp. 887-895) (Year: 2005).*
Hozumi et al. ('Cell surface receptor-specific scaffold requirements for adhesion to laminin-derived peptide-chitosan membranes' Biomaterials v31 2010 pp. 3237-3243). (Year: 2010).*
Nam et al. ('Laminin-111 peptides conjugated to fibrin hydrogels promote formation of lumen containing parotid gland cell clusters' Biomacromolecules v17 2016 pp. 2293-2301). (Year: 2016).*
Schense et al. ('Enzymatic incorporation of bioactive peptides into fibrin matrices enhances neurite extension' Nature Biotechnology v18 Apr. 2000 pp. 415-419). (Year: 2000).*
Adams et al., "Self-Assembly of Surfactant-like Peptides," Langmuir, 2007, 23(25):12729-12736.
Aframian et al., "The growth and morphological behavior of salivary epithelial cells on matrix protein-coated biodegradable substrata," Tissue Eng., 2000, 6(3):209-16.
Akiyama, "Integrins in cell adhesion and signaling," Hum Cell, 1996, 9, (3):181-6.
Almståhl et al., "Microflora in oral ecosystems in subjects with radiation-induced hyposalivation," Oral Dis, 2008, 14:541-9.
Alston et al., "New method to prepare autologous fibrin glue on demand," Transl Res, 2007, 149:187-95.
Asakura et al., "Fibroblasts spread on immobilized fibrin monomer by mobilizing a beta1-class integrin, together with a vitronectin receptor alphavbeta3 on their surface," J Biol Chem, 1997, 272(13):8824-9.
Aumailley M., "The laminin family," Cell Adhesion & Migration, 2013, 7(1):48-55.
Aure et al., "Salivary Gland Homeostasis Is Maintained through Acinar Cell Self-Duplication," Developmental Cell, 2015, 33(2):231-237.
Baker et al., "Rat parotid gland cell differentiation in three-dimensional culture," Tissue Eng Part C Methods, 2010, 16(5):1135-44.
Baker, "Current trends in salivary gland tight junctions," Tissue Barriers, 2016, 4(3):e1162348.
Beck et al., "Structure and function of laminin: anatomy of a multidomain glycoprotein," FASEB Journal, 1990, 4(2): 148-160.
Beliveau et al., "Raf-induced MMP9 disrupts tissue architecture of human breast cells in three-dimensional culture and is necessary for tumor growth in vivo," Genes & Development, 2010, 24(24):2800-11.
Bellis, "Advantages of RGD peptides for directing cell association with biomaterials," Biomaterials, 2011, 32(18):4205-10.
Brett, "A Review of Collagen and Collagen-based Wound Dressings," Wounds, 2008, 20(12):347-56.

(Continued)

*Primary Examiner* — Ronald T Niebauer
(74) *Attorney, Agent, or Firm* — Michael Best & Friedrich LLP

(57) ABSTRACT

The invention is directed to a composition comprising a fibrin hydrogel conjugated to peptides of laminin-111 (L1) and methods for repairing damaged salivary tissue using the composition.

15 Claims, 51 Drawing Sheets

Specification includes a Sequence Listing.

(56) References Cited

OTHER PUBLICATIONS

Burgess et al., "Loss of human Greatwall results in G2 arrest and multiple mitotic defects due to deregulation of the cyclin B-Cdc2/PP2A balance," Proc Natl Acad Sci USA, 2010, 107(28):12564-9.
Callea et al., "Ear nose throat manifestations in hypoidrotic ectodermal dysplasia," Int J Pediatr Otorhinolaryngol, 2013, 77(11):1801-4.
Cantara et al., "Selective functionalization of nanofiber scaffolds to regulate salivary gland epithelial cell proliferation and polarity," Biomaterials, 2012, 33(33):8372-82.
Carlsson et al., "Protein thiolation and reversible protein-protein conjugation. N-Succinimidyl 3-(2-pyridyldithio)propionate, a new heterobifunctional reagent," Biochem J, 1978, 173(3):723-37.
Castro et al., "Oral dryness in Sjögren's syndrome patients. Not just a question of water," Autoimmun Rev, 2013, 12(5):567-74.
Catalan et al., "The salivary gland fluid secretion mechanism," J Med Invest, 2009, 56 Suppl, 192-6.
Cattavarayane et al., "α6β1- and αV-integrins are required for long-term self-renewal of murine embryonic stem cells in the absence of LIF," BMC Cell Biology, 2015, 16:3, 13 pages.
Chambers et al., "Radiation-induced xerostomia in patients with head and neck cancer: pathogenesis, impact on quality of life, and management," Head Neck, 2004, 26(9):796-807.
Colognato et al., "Form and function: the laminin family of heterotrimers," Dev. Dyn., 2000, 218(2):213-234.
D' Emanuele et al., "An electrically modulated drug delivery device: I," Pharm Res., 1991, 8:913-918.
Debye, "Molecular-weight determination by light scattering," J Phys Colloid Chem, 1947, 51(1):18-32.
Del Bufalo et al., "3D modeling of human cancer: A PEG-fibrin hydrogel system to study the role of tumor microenvironment and recapitulate the in vivo effect of oncolytic adenovirus," Biomaterials, 2016, 84:76-85.
Des Rieux et al., "Fibrin hydrogels for non-viral vector delivery in vitro," J Control Release, 2009, 136(2):148-54.
Dhandayuthapani et al., "Polymeric Scaffolds in Tissue Engineering Application: A Review," Int J Polym Sci, 2011, vol. 2011, Article ID 290602, 19 pages.
Dijkema et al., "MUC5B levels in submandibular gland saliva of patients treated with radiotherapy for head-and-neck cancer: A pilot study," Radiat Oncol, 2012, 7(1):91, 4 pages.
Edmondson et al., "Three-dimensional cell culture systems and their applications in drug discovery and cell-based biosensors," Assay Drug Dev Technol, 2014, 12(4):207-18.
Ehrlich et al., "Collagen Organization Critical Role in Wound Contraction," Advances in Wound Care, 2012, 1(1):3-9.
El-Sherbiny et al., "Hydrogel scaffolds for tissue engineering: Progress and challenges," Glob Cardiol Sci Pract 2013, 2013, 316-42.
Feng et al., "Isolation and characterization of human salivary gland calls for stem cell transplantation to reduce radiation-induced hyposalivation," Radiother Oncol 2009, 92, 466-71.
Ferreira et al., "Evaluation of poly(2-hydroxyethyl methacrylate) gels as drug delivery systems at different pH values," Int J Pharm., 2000, 194:169-180.
Foskett et al., "Activation of Salivary Secretion: Coupling of Cell Volume and $[Ca^{2+}]_i$ in Single Cells," Science 1989, 244, 1582-5.
Francisco et al., "Injectable Laminin-Functionalized Hydrogel for Nucleus Pulposus Regeneration," Biomaterials, 2013, 34(30):7381-7388.
Freitas et al., "SIKVAV, a laminin alpha1-derived peptide, interacts with integrins and increases protease activity of a human salivary gland adenoid cystic carcinoma cell line through the ERK 1/2 signaling pathway," Am J Pathol, 2007, 171(1):124-38.
Fridman et al., "Reconstituted basement membrane (matrigel) and laminin can enhance the tumorigenicity and the drug resistance of small cell lung cancer cell lines," Proc Natl Acad Sci USA, 1990, 87(17):6698-702.
Frith et al., "Tailored integrin-extracellular matrix interactions to direct human mesenchymal stem cell differentiation," Stem cells and development, 2012, 21(13):2442-56.
Gauthier et al., "Peptide/protein-polymer conjugates: synthetic strategies and design concepts," Chem Commun, 2008, 21(23):2591-611.
Geer et al., "Biomimetic delivery of keratinocyte growth factor upon cellular demand for accelerated wound healing in vitro and in vivo," Am J Pathol, 2005, 167(6):1575-86.
Geiger et al., "Molecular Architecture and Function of Matrix Adhesions," Cold Spring Harb Perspect Biol, 2011, 3(5):a005033, 21 pages.
Ghajar et al., "Extracellular matrix control of mammary gland morphogenesis and tumorigenesis: insights from imaging," Histochem Cell Biol, 2008, 130(6):1105-18.
Goodman et al., "3-D tissue culture systems for the evaluation and optimization of nanoparticle-based drug carriers," Bioconjug Chem, 2008, 19(10):1951-9.
Goudenege et al., "Laminin-111: a potential therapeutic agent for Duchenne muscular dystrophy," Mol. Ther., 2010, 18: 2155-2163.
Guenet, J.M., Thermoreversible gelation of polymers and biopolymers; Academic Press, New York (1992), p. 89.
Guler et al., "A Self-Assembled Nanofiber Catalyst for Ester Hydrolysis," J Am Chem Soc., 2007, 129(40):12082-12083.
Gutowska et al., "Heparin release from thermosensitive hydrogels," J Control Release, 1992, 22: 95-104.
Han et al., "Dry mouth: a critical topic for older adult patients," J Prosthodont Res, 2015, 59(1):6-19.
Hanenberg et al., "Colocalization of retrovirus and target cells on specific fibronectin fragments increases genetic transduction of mammalian cells," Nat Med, 1996, 2(8):876-82.
Hartgerink et al., "Self-assembly and mineralization of peptide-amphiphile nanofibers," Science, 2001, 294(5547):1684-1688.
He et al., "The influence of laminin-derived peptides conjugated to Lys-capped PLLA on neonatal mouse cerebellum C17.2 stem cells," Biomaterials, 2009, 30(8):1578-86.
Hersel et al., "RGD modified polymers: biomaterials for stimulated cell adhesion and beyond," Biomaterials, 2003, 24(24):4385-4415.
Hoffman et al., "Cell type-specific differences in glycosaminoglycans modulate the biological activity of a heparin-binding peptide (RKRLQVQLSIRT) from the G domain of the laminin alpha1 chain," The Journal of biological chemistry, 2001, 276(25):22077-85.
Hoffman et al., "Laminin-1 and laminin-2 G-domain synthetic peptides bind syndecan-1 and are involved in acinar formation of a human submandibular gland cell line," The Journal of biological chemistry, 1998, 273(44):28633-41.
Hoffman, "Hydrogels for biomedical applications," Ann. NY Acad. Sci., 2001, 944:62-73.
Hood et al., "Role of integrins in cell invasion and migration," Nat Rev Cancer, 2002, 2(2):91-100.
Horejs et al., "Biologically-active laminin-111 fragment that modulates the epithelial-to-mesenchymal transition in embryonic stem cells," Proceedings of the National Academy of Sciences of the United States of America, 2014, 111(16):5908-13.
Hosokawa et al., "Significant role of laminin-1 in branching morphogenesis of mouse salivary epithelium cultured in basement membrane matrix," Development, Growth & Differentiation. 1999, 41(2):207-16.
Hozumi et al., "Reconstitution of laminin-111 biological activity using multiple peptide coupled to chitosan scaffolds," Biomaterials, 2012, 33(17):4241-50.
Hsiao et al., "Data supporting chitosan facilitates structure formation of the salivary gland by regulating the basement membrane components," Data in Brief, 2015, 4:551-8.
Hwang et al., "Self-assembling biomaterials: Liquid crystal phases of cholesteryl oligo(l-lactic acid) and their interactions with cells," Proc. Natl. Acad. Sci. USA, 2002, 99(15):9662-9667.
Imhof et al., "Adhesion mechanisms regulating the migration of monocytes," Nat Rev Immunol 2004, 4(6):432-444.
International Search Report and Written Opinion for Application No. PCT/US2017/052174 dated Feb. 5, 2018 (11 pages).

(56) References Cited

OTHER PUBLICATIONS

Itoh et al., "Effects of a laminin peptide (YIGSR) immobilized on crab-tendon chitosan tubes on nerve regeneration," J Biomed Mater Res B Appl Biomater, 2005, 73(2):375-82.
Janmey et al., "Fibrin gels and their clinical and bioengineering applications," Journal of The Royal Society Interface, 2009, 6(30):1-10.
Jeong et al., "Human salivary gland stem cells ameliorate hyposalivation of radiation-damaged rat salivary glands," Exp Mol Med, 2013, 45:e58, 7 pages.
Jiang et al., "Distinct distribution of laminin and its integrin receptors in the pancreas," J Histochem Cytochem, 2002, 50(12):1625-32.
Jockenhoevel et al., "Fibrin gel—advantages of a new scaffold in cardiovascular tissue engineering," European Journal of Cardio-Thoracic Surgery, 2001, 19(4):424-430.
Ju et al., "pH/temperature-responsive semi-IPN hydrogels composed of alginate and poly(N-isopropylacrylamide)," J. Appl. Polym. Sci., 2002, 83:1128-1139.
Kalogeris et al., "Cell Biology of Ischemia/Reperfusion Injury," Int Rev Cell Mol Biol, 2012, 298:229-317.
Kałużny et al., "Radiotherapy induced xerostomia: mechanisms, diagnostics, prevention and treatment-evidence based up to 2013," Otolaryngologia Polska, 2014, 68(1):1-14.
Kesimer et al., "Identification of salivary mucin MUC7 binding proteins from *Streptococcus gordonii*," BMC Microbiol, 2009, 9:163, 10 pages.
Kidd et al., "Fibrin hydrogels for lentiviral gene delivery in vitro and in vivo," J Control Release, 2012, 157(1):80-5.
Kikkawa et al., "Laminin-111-derived peptides and cancer," Cell Adh Migr, 2013, 7(1):150-159.
Kinstler et al., "Mono-N-terminal poly(ethylene glycol)-protein conjugates," Adv Drug Deliv Rev, 2002, 54(4):477-85.
Kipper et al., "Covalent surface chemistry gradients for presenting bioactive peptides," Anal. Biochem., 2007, 363:175-184.
Kongkaneramit et al., "Dependence of reactive oxygen species and FLICE inhibitory protein on lipofectamine-induced apoptosis in human lung epithelial cells," J Pharmacol Exp Ther, 2008, 325(3):969-77.
Kruegel et al., "Basement membrane components are key players in specialized extracellular matrices," Cell Mol Life Sci, 2010, 67(17):2879-95.
Langer et al., "Designing materials for biology and medicine," Nature, 2004, 428:487-492.
Lawrence et al., "Oral health-related quality of life in a birth cohort of 32-year olds," Community Dent Oral Epidemiol, 2008, 36(4):305-16.
Lei et al., "Cell-controlled and spatially arrayed gene delivery from fibrin hydrogels," Biomaterials, 2009, 30(22):3790-9.
Leigh et al., "Three-dimensional cultures of mouse submandibular and parotid glands: a comparative study," Tissue Eng Regen Med, 2017, 11(3):618-626.
Li et al., "Fibrin gel as an injectable biodegradable scaffold and cell carrier for tissue engineering," ScientificWorld Journal, 2015, vol. 2015, Article ID 685690, 10 pages.
Li et al., "Structural and functional characteristics of irradiation damage to parotid glands in the miniature pig," Int J Radiat Oncol Biol Phys, 2005, 62(5):1510-6.
Liang et al., "Differential and synergistic effects of mechanical stimulation and growth factor presentation on vascular wall function," Biomaterials. 2013, 34(30):7281-91.
Liang et al., "Engineering fibrin-binding TGF-β1 for sustained signaling and contractile function of MSC based vascular constructs," Biomaterials, 2011, 32(33):8684-93.
Lin et al., "Effects of radiotherapy on salivary gland function in patients with head and neck cancers," Journal of Dental Sciences, 2015, 10(3):253-62.
Litvinov et al., "Multi-Step Fibrinogen Binding to the Integrin αIIbβ3 Detected Using Force Spectroscopy," Biophys J, 2005, 89(4):2824-34.

Maeda et al., "Cell-adhesive activity and receptor-binding specificity of the laminin-derived YIGSR sequence grafted onto Staphylococcal protein A," J Biochem, 1994, 115(2):182-9.
Marder et al., "High molecular weight derivatives of human fibrinogen produced by plasmin. I. Physicochemical and immunological characterization," J Biol Chem, 1969, 244(8):2111-9.
Maruyama et al., "Stem Cell Soluble Signals Enhance Multilumen Formation in SMG Cell Clusters," J Dent Res, 2015, 94(11):1610-7.
Matsuzaki et al., "Aquaporin-5 (AQP5), a water channel protein, in the rat salivary and lacrimal glands: immunolocalization and effect of secretory stimulation," Cell Tissue Res 1999, 295(3):513-21.
Matsuzaki et al., "Function of the Membrane Water Channel Aquaporin-5 in the Salivary Gland," Acta Histochemica et Cytochemica, 2012, 45(5):251-259.
McCall et al., "Growth Factors Polymerized Within Fibrin Hydrogel Promote Amylase Production in Parotid Cells," Tissue Eng Part A, 2013, 19(19-20):2215-25.
Mochizuki et al., "Laminin-1 peptide-conjugated chitosan membranes as a novel approach for cell engineering," FASEB J, 2003, 17(8):875-7.
Mullen et al., "Effect of Matrigel on the tumorigenicity of human breast and ovarian carcinoma cell lines," Int J Cancer, 1996, 67(6):816-20.
Nam et al., "L1 Peptide-Conjugated Fibrin Hydrogels Promote Salivary Gland Regeneration," J Dent Res, 2017, 96(7):798-806.
Nam et al., "Laminin-111 Peptides Conjugated to Fibrin Hydrogels Promote Formation of Lumen Containing Parotid Gland Cell Clusters," Biomacromolecules, 2016, 17(6):2293-301.
Nam et al., "Laminin-111-derived conjugated fibrin hydrogel restore salivary gland function," PLoS ONE, 2017, 12(11):e0187069.
Nam K, Jones JP, Lei P, Andreadis ST, Baker OJ. Laminin-111 Peptides Conjugated to Fibrin Hydrogels Promote Formation of Lumen Containing Parotid Gland Cell Clusters. Biomacromolecules. 2016, 17(6):2293-2301.
Nanduri et al., "Regeneration of irradiated salivary glands with stem cell marker expressing cells," Radiother Oncol, 2011, 99(3):367-72.
Nanduri et al., "Salisphere derived c-Kit+ cell transplantation restores tissue homeostasis in irradiated salivary gland," Radiother Oncol, 2013, 108(3):458-63.
O'Brien, "Biomaterials & scaffolds for tissue engineering," Mater Today, 2011, 14(3):88-95.
Odusanwo et al., "Resolvin D1 prevents TNF-α-mediated disruption of salivary epithelial formation," Am J Physiol Cell Physiol, 2012, 302(9):C1331-45.
Ogawa et al., "Functional salivary gland regeneration by transplantation of a bioengineered organ germ," Nat Commun, 2013, 4:2498, 10 pages.
Padmashali et al., "Engineering fibrinogen-binding VSV-G envelope for spatially- and cell-controlled lentivirus delivery through fibrin hydrogels," Biomaterials, 2011, 32(12):3330-9.
Parveen et al., "New Era in Health Care: Tissue Engineering," J Stem Cells Regen Med, 2006, 1(1):8-24.
Patel et al., "Salivary Gland Development: A Template for Regeneration," Semin Cell Dev Biol, 2014, 25-26:52-60.
Peña et al., "Biomimetic Polymers for Cardiac Tissue Engineering," Biomacromolecules, 2016, 17(5):1593-1601.
Peppas et al., "Hydrogels in pharmaceutical formulations," Eur. J. Pharm. Biopharm., 2000, 50(1):27-46.
Pillemer et al., "Incidence of physician-diagnosed primary Sjogren syndrome in residents of Olmsted County, Minnesota," Mayo Clin Proc, 2001, 76(6):593-9.
Pinna et al., "Xerostomia induced by radiotherapy: an overview of the physiopathology, clinical evidence, and management of the oral damage," Ther Clin Risk Manag, 2015, 11:171-88.
Pook et al., "Changes in Laminin Expression Pattern during Early Differentiation of Human Embryonic Stem Cells," PLoS One, 2015, 10(9):e0138346.
Porter et al., "An update of the etiology and management of xerostomia," Oral Surg Oral Med Oral Pathol Oral Radiol Endod, 2004, 97(1):28-46.
Pradhan-Bhatt et al., "A novel in vivo model for evaluating functional restoration of a tissue-engineered salivary gland," Laryngoscope, 2014, 124(2):456-61.

(56) References Cited

OTHER PUBLICATIONS

Quissel et al., "Development and characterization of immortalized rat parotid and submandibular acinar cell lines," Eur J Morphol, 1998, 36 Suppl, 50-4.
Rajasekaran et al., "Interactions of tight junctions with membrane channels and transporters," BBA-Biomembranes, 2008, 1778(3):757-69.
Rao et al., "Changes in the subunit composition of laminin during the increased tumorigenesis of mouse A9 cells," Connect Tissue Res, 1991, 25(3-4):321-9.
Rasmussen et al., "Collagen Type I Improves the Differentiation of Human Embryonic Stem Cells towards Definitive Endoderm," PLoS One, 2015, 10(12):e0145389.
Raut et al., "Fibrin-mediated lentivirus gene transfer: implications for lentivirus microarrays," J Control Release, 2010, 144(2):213-20.
Ravi et al., "3D cell culture systems: advantages and applications," J Cell Physiol, 2015, 230(1):16-26.
Riederer et al., "Laminin therapy for the promotion of muscle regeneration," FEBS Letters, 2015, 589(22):3449-3453.
Riopel et al., "β1 integrin-extracellular matrix interactions are essential for maintaining exocrine pancreas architecture and function," Lab Invest, 2013, 93(1):31-40.
Romanenko et al., "Tmem16A encodes the Ca2+-activated Cl-channel in mouse submandibular salivary gland acinar cells," J Biol Chem, 2010, 285(17):12990-13001.
Rooney et al., "Laminin-111 protein therapy prevents muscle disease in the mdx mouse model for Duchenne muscular dystrophy," Proc. Natl. Acad. Sci. USA, 2009, 106(19):7991-7996.
Rooney et al., "Laminin-111 Protein Therapy Reduces Muscle Pathology and Improves Viability of a Mouse Model of Merosin-Deficient Congenital Muscular Dystrophy," Am. J. Pathol., 2012, 180(4):1593-1602.
Rooney et al., "Laminin-111 Restores Regenerative Capacity in a Mouse Model for alpha7 Integrin Congenital Myopathy," Am. J. Pathol., 2009, 174(1):256-264.
Shaikh et al., "Fibrin: a natural biodegradable scaffold in vascular tissue engineering," Cells Tissues Organs, 2008, 188(4):333-46.
Shin et al., "Biomimetic materials for tissue engineering," Biomaterials, 2003, 24:4353-4364.
Silva-Barbosa et al., "Human myoblast engraftment is improved in laminin-enriched microenvironment," Transplantation, 2008, 85(4):566-575.
Skrinjar et al., "Comparison between three different saliva substitutes in patients with hyposalivation," Clinical oral investigations, 2015, 19(3):753-7.
Slaughter et al., "Hydrogels in regenerative medicine," Adv Mater, 2009, 21(32-33):3307-29.
Sonesson et al., "Mucins MUC5B and MUC7 in minor salivary gland secretion of children and adults," Arch Oral Biol, 2008, 53(6):523-7.
Soon et al., "Modulation of fibrin matrix properties via knob:hole affinity interactions using peptide-PEG conjugates," Biomaterials, 2011, 32(19):4406-14.
Soscia et al., "Salivary gland cell differentiation and organization on micropatterned PLGA nanofiber craters," Biomaterials, 2013, 34(28):6773-84.
Stipp, "Laminin-binding integrins and their tetraspanin partners as potential antimetastatic targets," Expert Rev Mol Med, 2010, 12:e3.
Stuchbury et al., "A reporter group delivery system with both absolute and selective specificity for thiol groups and an improved fluorescent probe containing the 7-nitrobenzo-2-oxa-1,3-diazole moiety," Biochem J, 1975, 151(2):417-32.
Suehiro et al., "Fibrinogen binds to integrin alpha(5)beta(1) via the carboxyl-terminal RGD site of the Aalpha-chain," J Biochem, 2000, 128(4):705-10.
Swartz et al., "Engineering of fibrin-based functional and implantable small-diameter blood vessels," Am J Physiol Heart Circ Physiol, 2005, 288(3):H1451-60.
Thakor et al., "Effects of prolonged reduction in blood flow on submandibular secretory function in anesthetized sheep," J Appl Physiol, 2003, 95(2):751-7.
Topley et al., "Effect of reconstituted basement membrane components on the growth of a panel of human tumour cell lines in nude mice," British journal of cancer, 1993, 67(5):953-8.
Turner et al., "A rat parotid gland cell line, Par-C10, exhibits neurotransmitter-regulated transepithelial anion secretion," Am J Physiol, 1998, 275(2):C367-74.
Turner et al., "Dry mouth and its effects on the oral health of elderly people," J Am Dent Assoc, 2007, 138, Supplement 1, S15-S20.
Van Ry et al., "Laminin-111 improves muscle repair in a mouse model of merosin-deficient congenital muscular dystrophy," Hum. Mol. Genet., 2014, 23(2):383-396.
Villa et al., "Diagnosis and management of xerostomia and hyposalivation," Therapeutics and clinical risk management, 2015, 11:45-51.
Virtanen et al., "Laminin alpha1-chain shows a restricted distribution in epithelial basement membranes of fetal and adult human tissues," Exp Cell Res, 2000, 257(2):298-309.
Walker et al., "Diverse Roles of E-Cadherin in the Morphogenesis of the Submandibular Gland: Insights Into the Formation of Acinar and Ductal Structures," Developmental dynamics: an official publication of the American Association of Anatomists, 2008, 237(11):3128-3141.
Wedgwood et al., "Rheological and Turbidity Study of Fibrin Hydrogels," Macromol Symp, 2013, 334(1):117-25.
Weisel, "The mechanical properties of fibrin for basic scientists and clinicians," Biophys Chem, 2004, 112(2-3):267-76.
Weis-Fogh, "Fibrinogen prepared from small blood samples for autologous use in a tissue adhesive system," Eur Surg Res, 1988, 20(5-6):381-9.
Wells et al., "Lumen formation in salivary gland development," Front Oral Biol, 2010, 14:78-89.
Williams et al., "Self-assembled peptide nanoarrays: an approach to studying protein-protein interactions," Angew Chem Int Ed., 2007, 46(17):3051-3054.
Wohlrab et al., "Cell adhesion and proliferation on RGD-modified recombinant spider silk proteins," Biomaterials, 2012, 33(28):6650-9.
Wolf et al., "Collagen-based cell migration models in vitro and in vivo," Semin Cell Dev Biol, 2009, 20(8):931-41.
Yamada et al., "Laminin-111-derived peptide-hyaluronate hydrogels as a synthetic basement membrane," Biomaterials, 2013, 34(28):6539-47.
Yan et al., "Rheological properties of peptide-based hydrogels for biomedical and other applications," Chem Soc Rev, 2010, 39(9):3528-40.
Yang et al., "Chitosan facilitates structure formation of the salivary gland by regulating the basement membrane components," Biomaterials, 2015, 66:29-40.
Yang et al., "TMEM16A confers receptor-activated calcium-dependent chloride conductance," Nature, 2008, 455(7217):1210-1215.
Yao et al., "Composite fibrin scaffolds increase mechanical strength and preserve contractility of tissue engineered blood vessels," Pharm Res, 2008, 25(5):1212-21.
Yao et al., "Fibrin-based tissue-engineered blood vessels: differential effects of biomaterial and culture parameters on mechanical strength and vascular reactivity," Tissue Eng, 2005, 11(7-8):991-1003.
Yoshida et al., "The laminin-derived peptide YIGSR (Tyr-Ile-Gly-Ser-Arg) inhibits human pre-B leukaemic cell growth and dissemination to organs in SCID mice," Br J Cancer, 1999, 80(12):1898-904.
Yuan et al., "Hybrid Biomaterial with Conjugated Growth Factors and Mesenchymal Stem Cells for Ectopic Bone Formation," Tissue Eng Part A, 2016, 22(13-14):928-39.
Zhang et al., "Neurite outgrowth on well-characterized surfaces: preparation and characterization of chemically and spatially controlled fibronectin and RGD substrates with good bioactivity," Biomaterials, 2005, 26(1):47-61.
Zhu et al., "Design properties of hydrogel tissue-engineering scaffolds," Expert Rev Med Devices, 2011, 8(5):607-26.

(56) References Cited

OTHER PUBLICATIONS

Zhu et al., "Synthesis and characterization of a redox-initiated, injectable, biodegradable hydrogel," J Appl Polym Sci., 2006, 99(5):2375-2583.
European Patent Office Extended Search Report for Application No. 17851757.9 dated May 26, 2020 (6 pages).

* cited by examiner

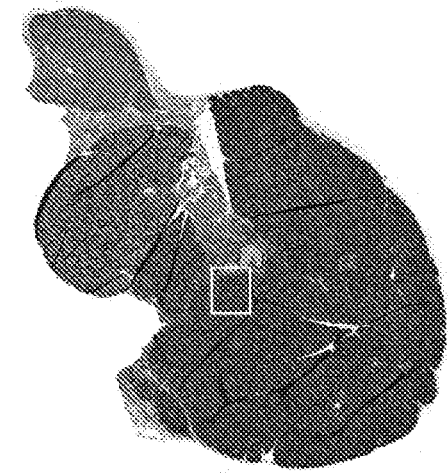
FIG. 19A
FIG. 19B
FIG. 19C

SALIVARY TISSUE REGENERATION USING LAMININ PEPTIDE-MODIFIED HYDROGELS

CROSS-REFERENCE TO RELATED APPLICATION(S)

This application is a U.S. national stage entry of International Patent Application No. PCT/US2017/052174, filed on Sep. 19, 2017, which claims priority to U.S. Provisional Patent Application No. 62/396,470, filed on Sep. 19, 2016, the entire contents of which are fully incorporated herein by reference.

STATEMENT REGARDING FEDERALLY SPONSORED RESEARCH OR DEVELOPMENT

This invention was made with government support under Grant Number DE022971 awarded by National Institute for Dental and Craniofacial Research the National Institutes of Health. The government has certain rights in the invention.

INCORPORATION-BY-REFERENCE OF MATERIAL SUBMITTED ELECTRONICALLY

Incorporated herein by reference in its entirety is a computer-readable nucleotide/amino acid sequence listing submitted concurrently herewith and identified as follows: One 1,828 Byte ASCII (Text) file named "U-6145-026389-9190-US01-SEQ-LIST-07-15-20 ST25.txt," created on Jul. 15, 2020.

BACKGROUND OF THE INVENTION

Proper salivary gland function is critical for oral health. Autoimmune disorders (such as Sjögren's syndrome), genetic diseases (such as ectodermal dysplasia), and γ-irradiation therapies (for head and neck cancers) cause salivary secretory dysfunction and lead to severe dryness of the oral cavity (see, e.g., Almståhl, et al., *Oral Dis* 2008, 14, 541-9; Castro et al., *J. Autoimmun. Rev.* 2013, 12, 567-74; and Callea et al., *Int. J. Pediatr Otorhinolaryngol* 2013, 77, 1801-4). Dry mouth can lead to oral infections, sleep disturbances, oral pain, and difficulty in chewing or swallowing food (see, e.g., Turner, M. D. and Ship, J. A., *J. Am. Dent. Assoc.*, 138: S15-S20 (2007); Kaluzny et al., *Otolaryngol. Pol.*, 68: 1-14 (2014); and Lin et al., *J. Dent. Sci.*, 10: 253-262 (2015)). Current treatments for salivary gland dysfunction, such as hyposalivation, include pharmaceuticals that induce saliva secretion from residual acinar cells (e.g., muscarinic receptor agonists pilocarpine and cevimeline) and saliva substitutes. However, the current treatments for dry mouth only provide temporary relief, and no tissue engineering approaches are currently available for patients suffering from dry mouth (see, e.g., Han et al., *J. Prosthodon. Res.*, 59: 6-19 (2015)).

Alternative therapies for treating hyposalivation have been explored, including stem cells, embryonic organ culture transplantation, scaffolds, and artificial salivary gland transplantation. In this regard, recent studies have shown that c-Kit+ stem cells, which are normally expressed in very low amounts in salivary gland (SG) specimens, can be expanded ex vivo to restore salivary gland function (see, e.g., Nanduri et al., *Radiother. Oncol.*, 99(3): 367-372 (2011); and Nanduri et al., *Radiother. Oncol.*, 108(3): 458-463 (2013)). Potential tumorigenesis and survival rates of stem cells, must be addressed before this technology can be translated to human use. Studies investigating embryonic organ culture transplantation have demonstrated that mouse embryonic salivary cells (i.e., submandibular, sublingual, and parotid gland cells) grown in an organ culture can be transplanted in vivo (see, e.g., Ogawa et al., *Na. Commun.*, 4: 2498 (2013)). Potential application of this technology in humans, however, is limited by diminished gland size and reduced survival times for animal subjects following treatment.

A variety of scaffolds comprised of biomaterials (e.g., poly-L-lactic acid, PLLA, poly-1-lactic-co-glycolic acid, PLGA nanofibers and chitosan) have been shown to allow cells to grow, attach, and organize to acquire features observed in salivary epithelium (see, e.g., Aframian et al., *Tissue Eng.*, 6(3): 209-216 (2000); Cantara et al., *Biomaterials*, 33: 8372-8382 (2012); Soscia et al., *Biomaterials*, 34(28): 6773-6784 (2013); Hsiao, Y. C. and Yang, T. L., *Data Brief* 4: 551-558 (2015); and Pradhan-Bhatt et al., *Laryngoscope*, 124(2): 456-461 (2014)); however further studies are required to demonstrate efficacy in vivo. For example, recent studies have shown that human cells grown on a hydroxyapatite (HA)-based scaffold and transplanted into a wounded mouse parotid gland appeared to allow integration of the scaffold into the wound, with subsequent expression of markers of progenitor cells noted (Pradhan-Bhatt S, et al., *Laryngoscope*, 124(2): 456-61 (2014)). These experiments did not monitor scaffold degradation or evidence of new tissue formation in vivo, raising concerns regarding the stability of the biomaterial and capacity for regeneration. Other studies have demonstrated that rat parotid Par-C10 cells and mouse parotid freshly isolated cells (PG) are capable of forming three dimensional structures with lumens and apical tight junctions when grown on growth factor-reduced-MATRIGEL® (GFR-MG; Corning, Inc., Corning, N.Y.). Conversely, both Par-C10 and PG cells grown on fibrin hydrogel (FH) failed to completely develop, indicating that components present on GFR-MG may induce a degree of differentiation in parotid single cells. Combining GFR-MG with FH, however, did not result in a recovery of acinar formation for either Par-C10 or PG cells, indicating that the acinar inducing components of GFR-MG require a critical concentration to be functional. Incorporating two growth factors that enhance salivary cell survival and differentiation (e.g., EGF and IGF-1) into a fibrin hydrogel was not enough to induce acinar formation, but was enough to induce amylase expression in PG primary cells (see, e.g., McCall et al., *Tissue Eng, Part A*, 19 (19-20): 2215-25 (2013)). Therefore, transplantation of artificial salivary glands is early stages of development, and the growth of viable tissue using a natural scaffold has yet to be demonstrated.

Accordingly, there remains a need for methods and compositions that support the growth of a functional salivary gland structure in vitro and in vivo. The present disclosure provides such methods and compositions.

BRIEF SUMMARY OF THE INVENTION

The disclosure provides a composition comprising a fibrin hydrogel conjugated to one or more peptides of laminin-111 (L1).

The disclosure also provides a method of generating salivary tissue in an animal in need thereof, which method comprises administering a composition comprising a fibrin hydrogel conjugated to one or more peptides of laminin-111 (L1) to an animal in need thereof, whereby salivary cells are generated in the animal.

The disclosure further provides a method of repairing damaged salivary tissue, which method comprises applying a composition comprising a fibrin hydrogel conjugated to one or more peptides of laminin-111 (L1) to damaged salivary tissue, whereby new salivary cells are generated and the damaged salivary tissue is repaired.

BRIEF DESCRIPTION OF THE SEVERAL VIEWS OF THE DRAWING(S)

Figure 4A:
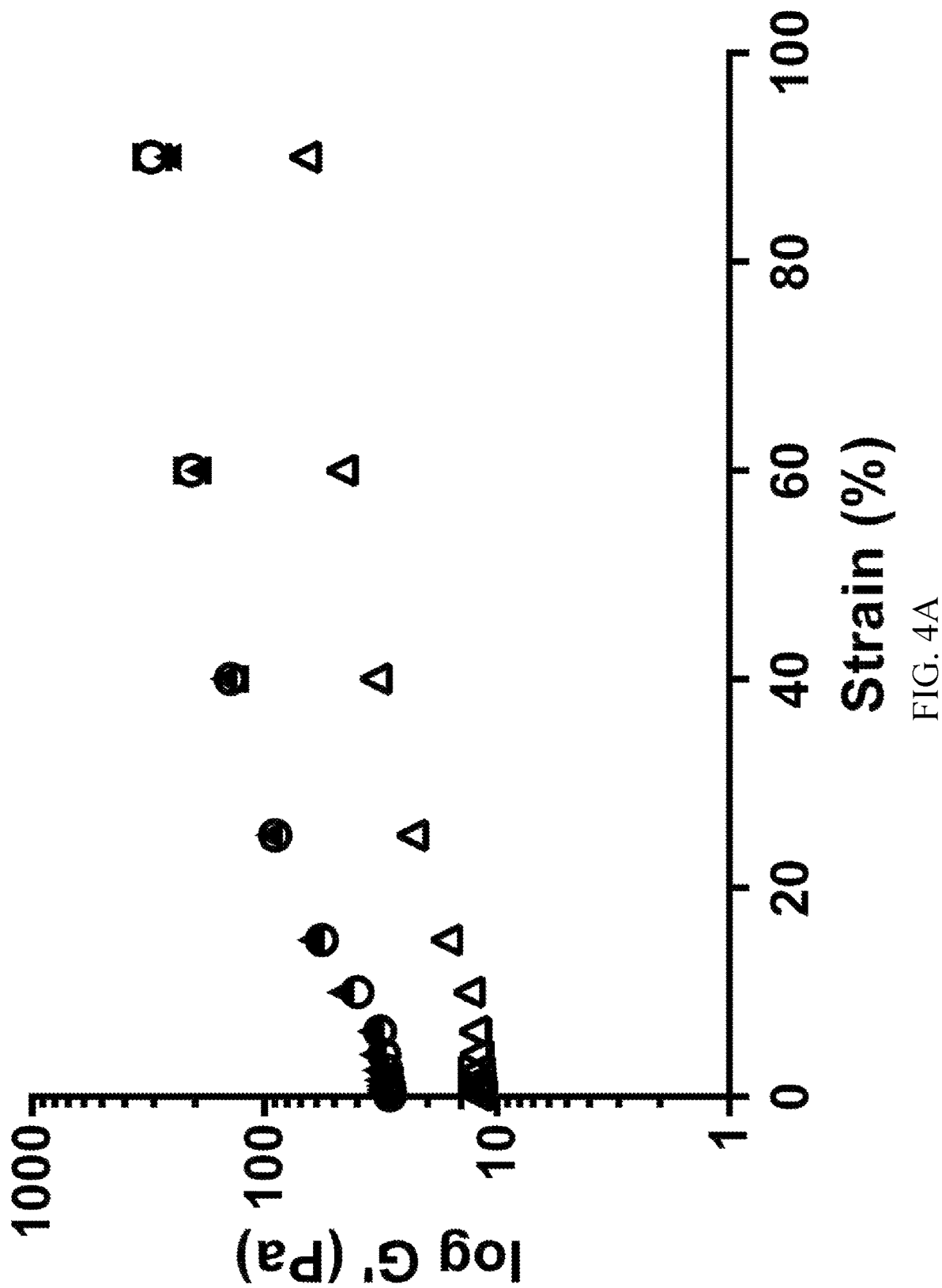

FIG. 4A is a graph illustrating the rheological parameters of the fibrin hydrogel (FH) conjugated to the YIGSR L1 peptide. Data represent the elasticity of unmodified FH (○), YIGSR-conjugated FH (□) and SGIYR-conjugated FH (■). Each data point represents the mean±SD (n=3, $p<0.05$).

Figure 4B:
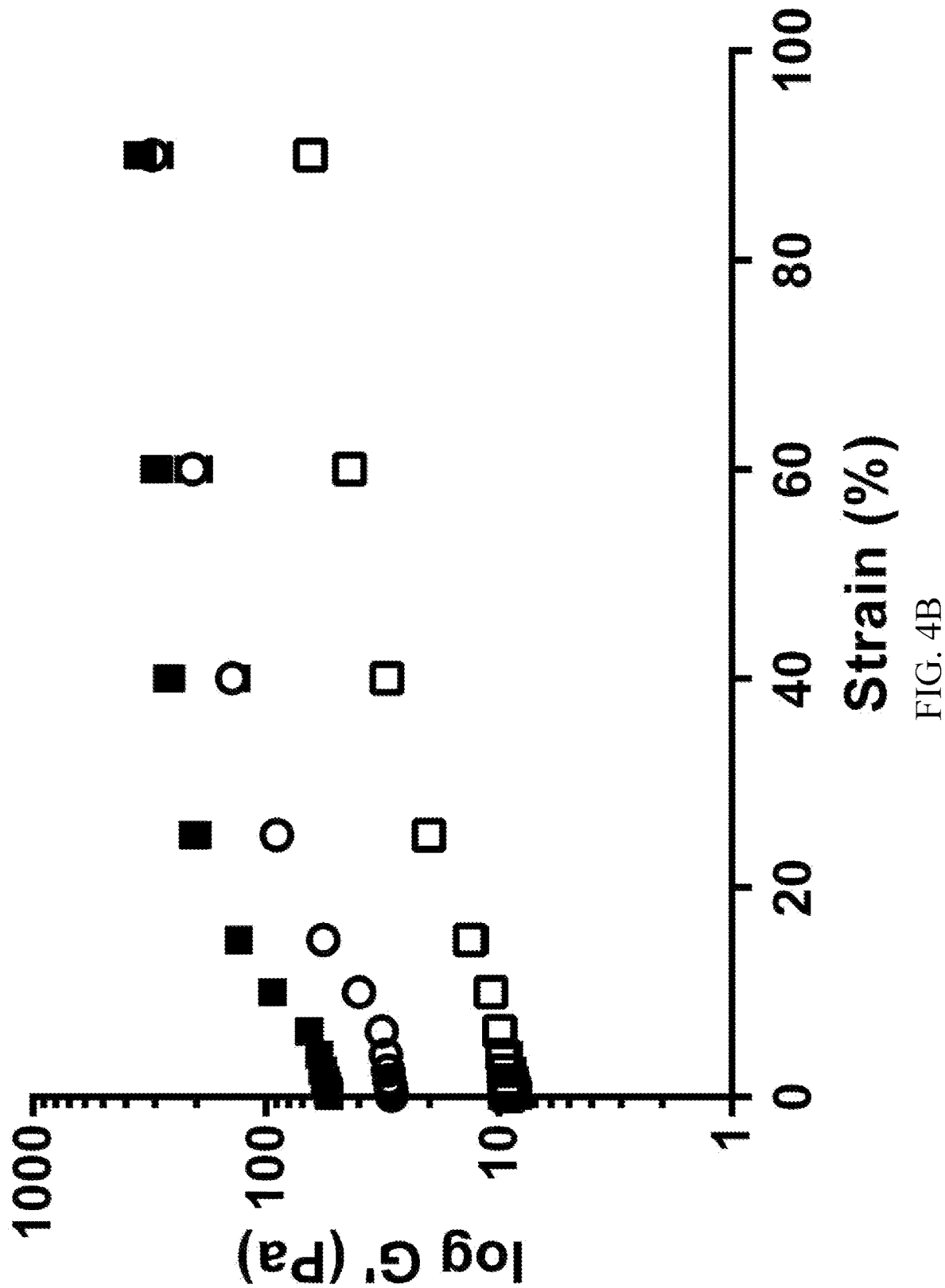

FIG. 4B is a graph illustrating the rheological parameters of the fibrin hydrogel (FH) conjugated to the A99 L1 peptide. Data represent the elasticity of unmodified FH (○), A99-conjugated FH (□), and RAD-conjugated FH (■). Each data point represents the mean±SD (n=3, $p<0.05$).

Figure 5:
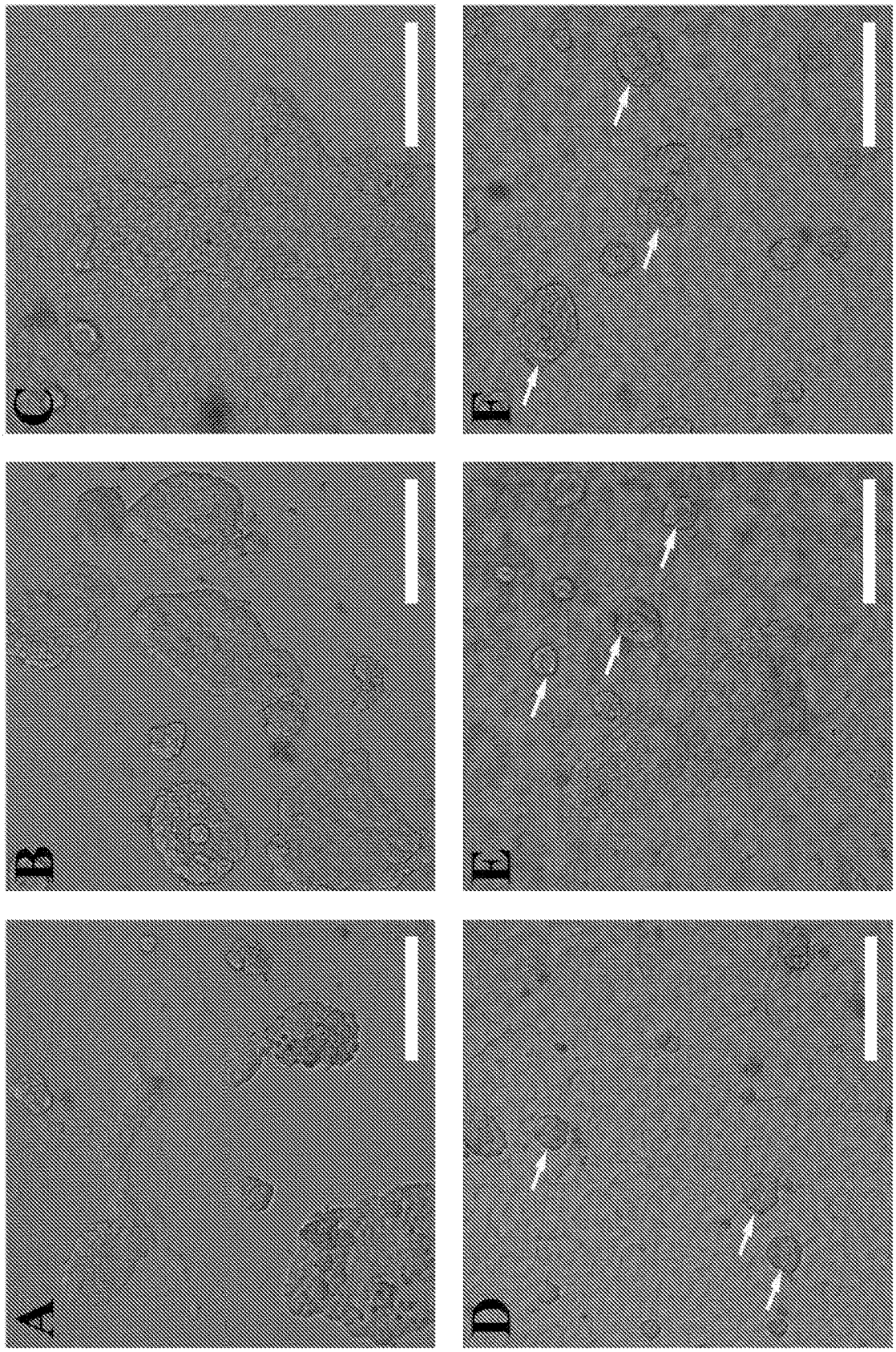

FIG. 5 is a series of images depicting Par-C10 salivary cell cluster formation organization on unmodified FH (A), SGIYR-conjugated FH (B), RAD-conjugated FH (C), YIGSR-conjugated FH (D), A99-conjugated FH (E), and a combination of YIGSR (50%)- and A99 (50%)-conjugated FH (F). Par-C10 cells grown on YIGSR and/or A99 peptide-conjugated FH formed round organized structures (white arrows). Scale bars represent 200 μm.

Figure 6A:
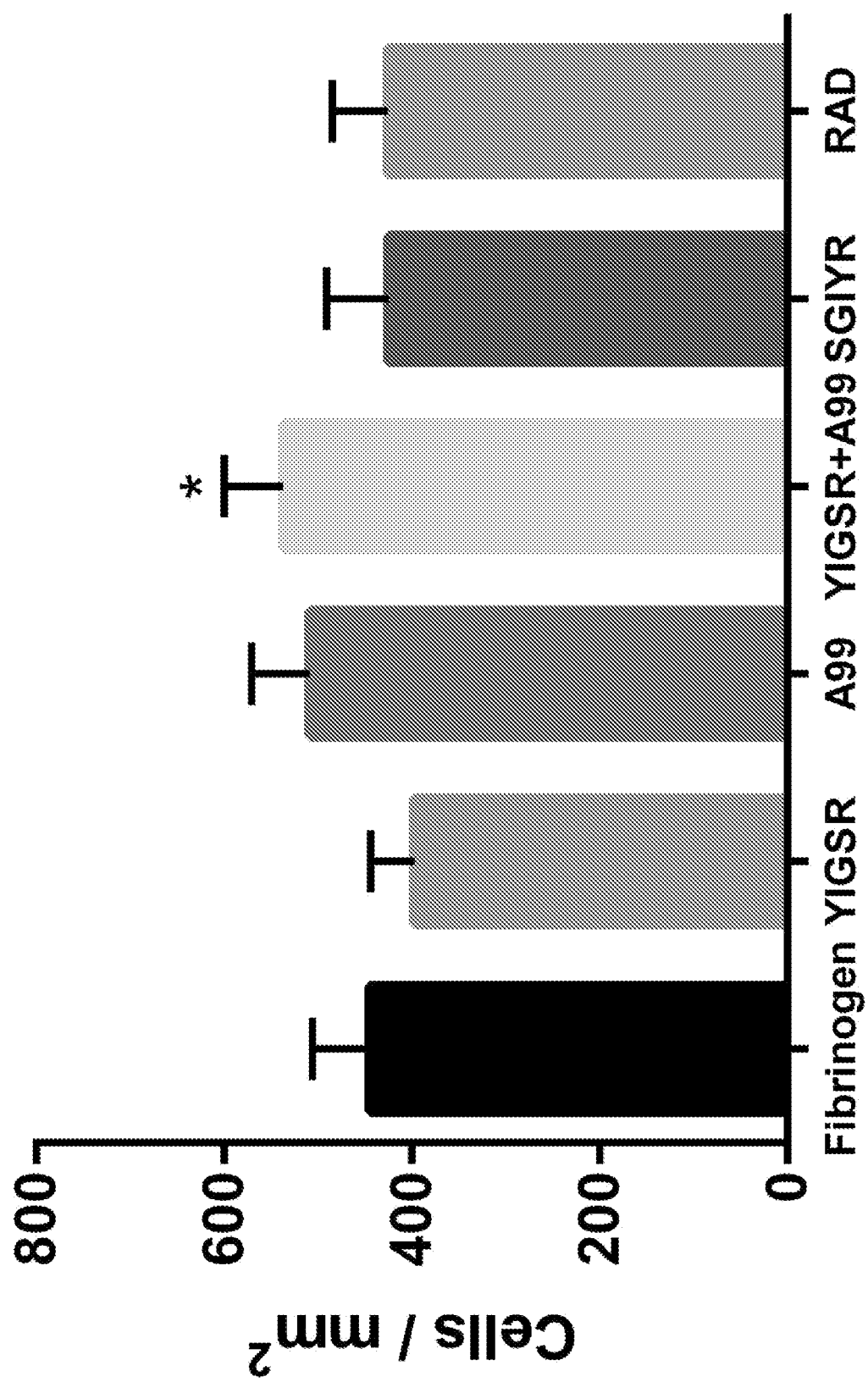
Figure 6B:
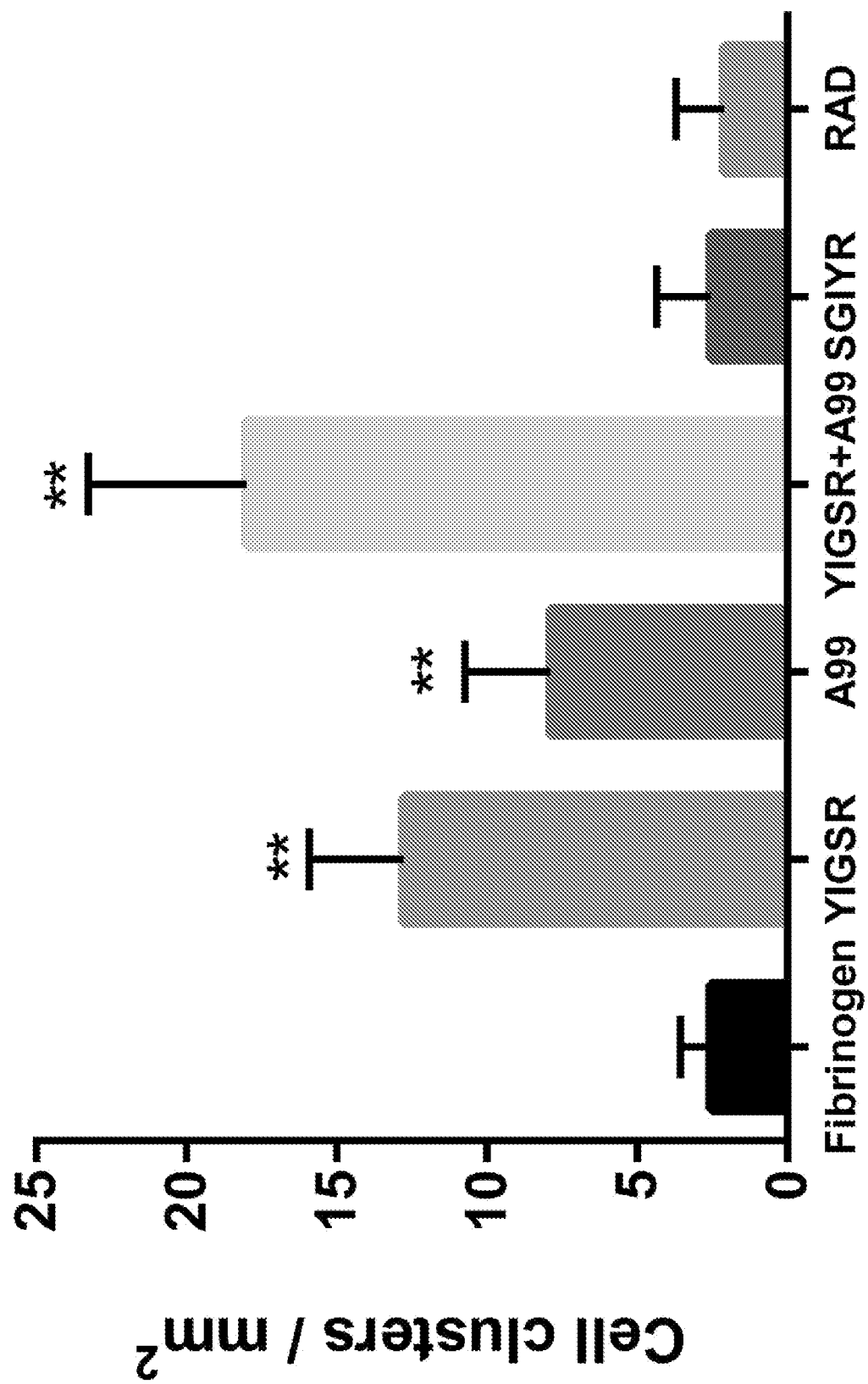

FIG. 6A is a bar chart showing total cell number formed on unmodified FH, YIGSR-conjugated fibrinogen, A99-conjugated FH, a combination of YIGSR (50%)- and A99 (50%)-conjugated FH, SGIYR-conjugated FH and RAD-conjugated FH. FIG. 6B is a bar chart showing the number of Par-C10 salivary cell clusters formed on unmodified FH, YIGSR-conjugated fibrinogen, A99-conjugated FH, a combination of YIGSR (50%)- and A99 (50%)-conjugated FH, SGIYR-conjugated FH and RAD-conjugated FH. A combination of the peptides YIGSR 50% and A99 50% showed an increase in cell attachment and Par-C10 cell cluster formation as compared to the unmodified FH. Each data point represents the mean±SD (n=9, *$p<0.05$, **$p<0.01$).

Figure 7A:
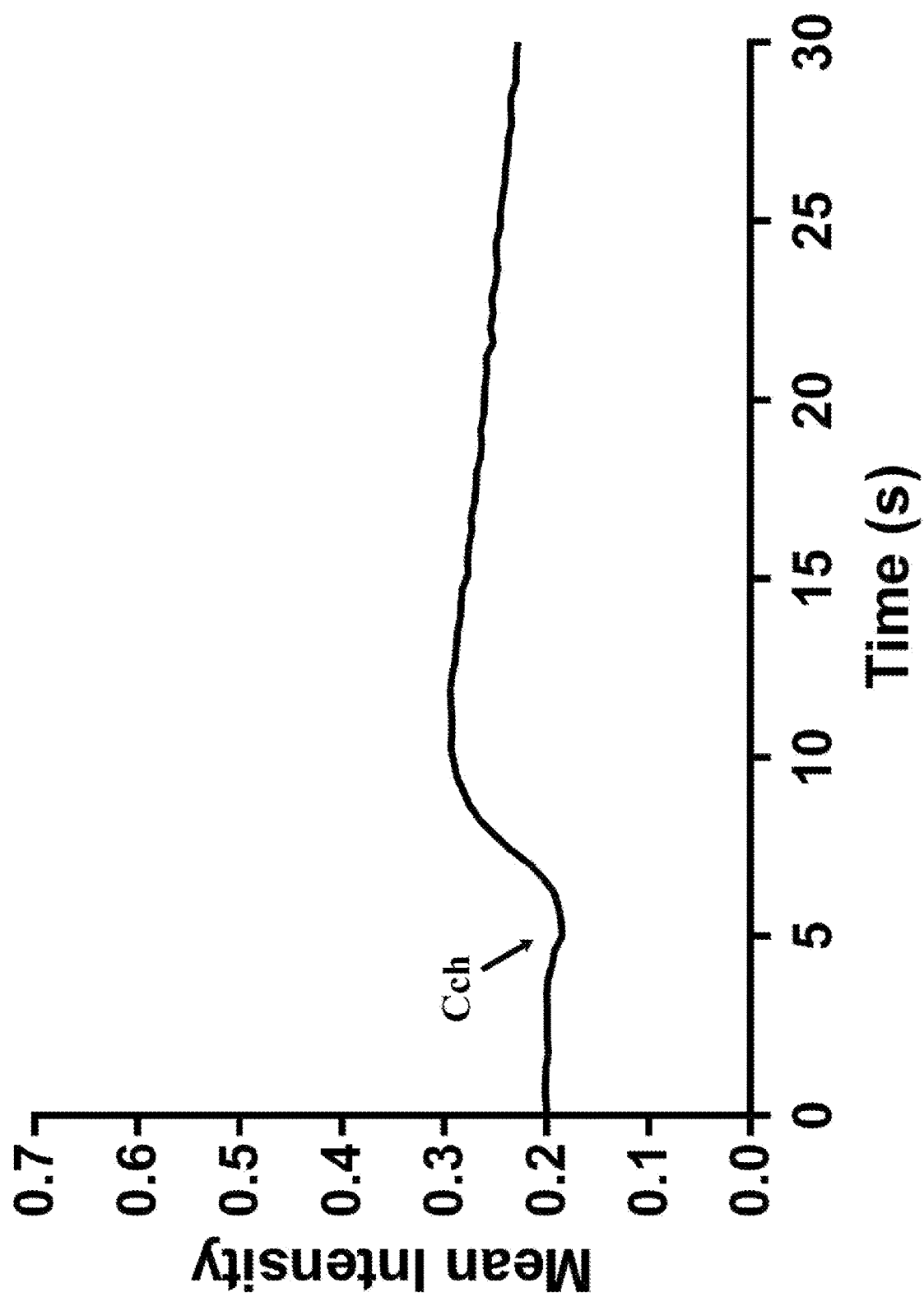
Figure 7B:
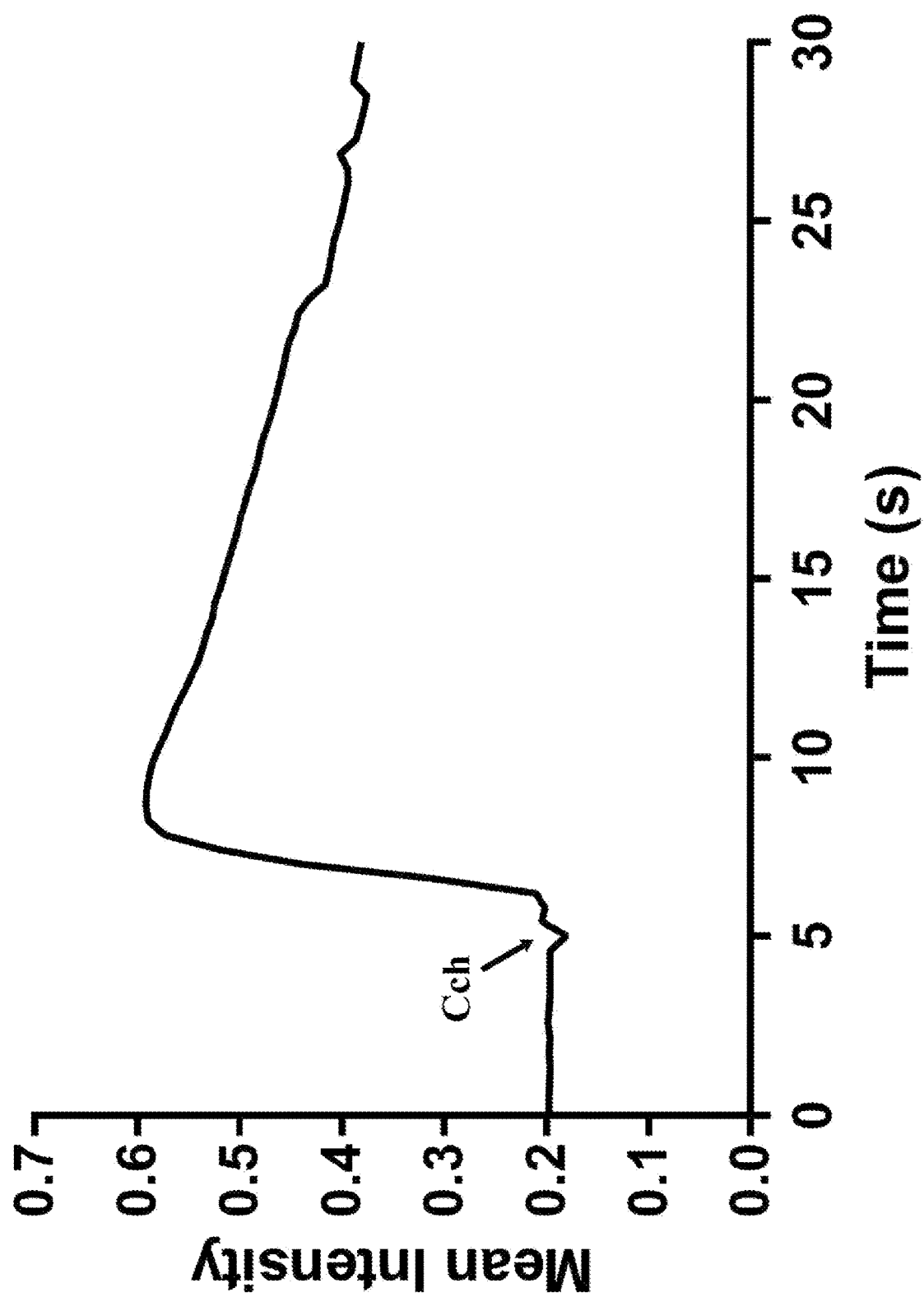
Figure 7C:
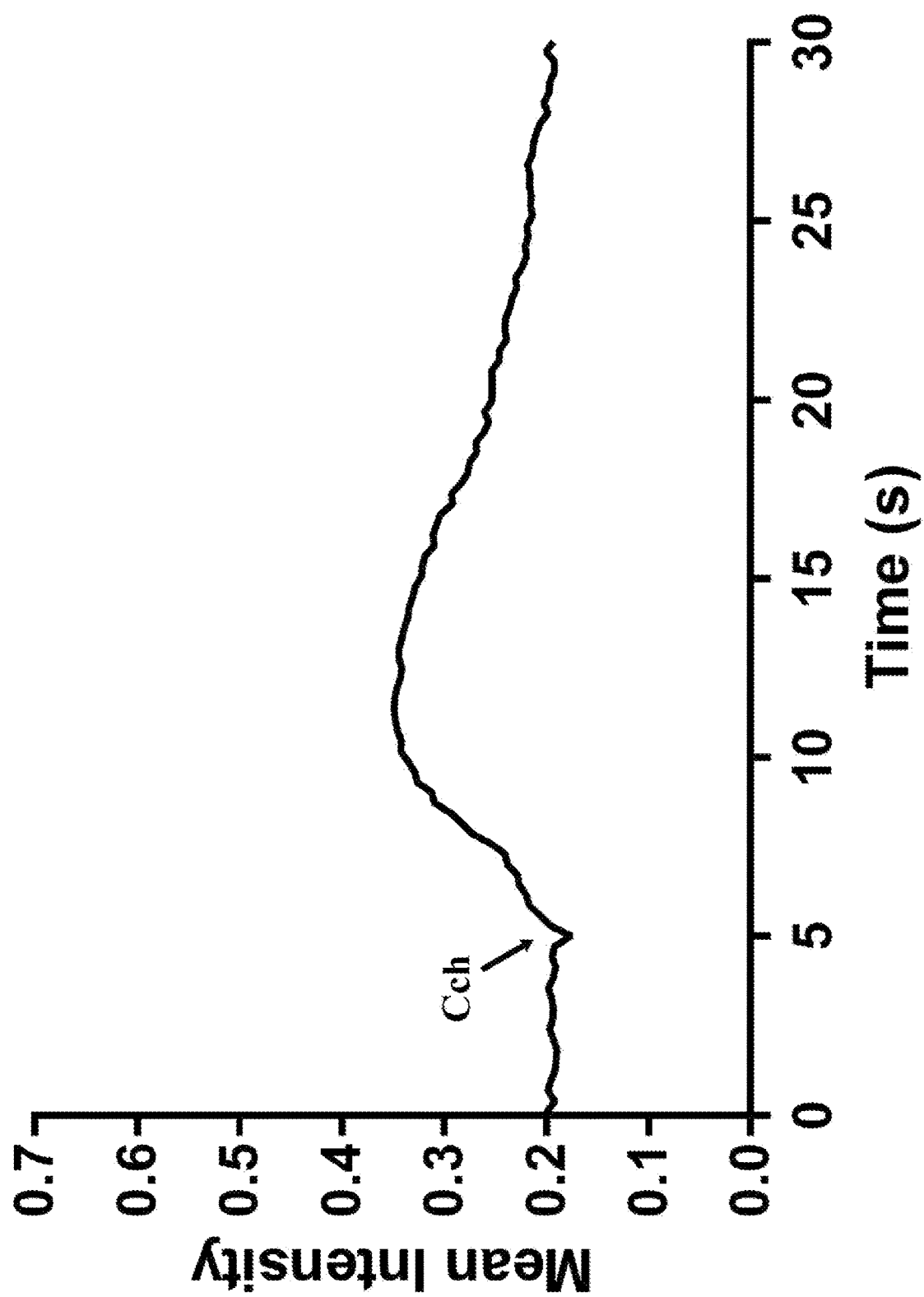
Figure 7D:
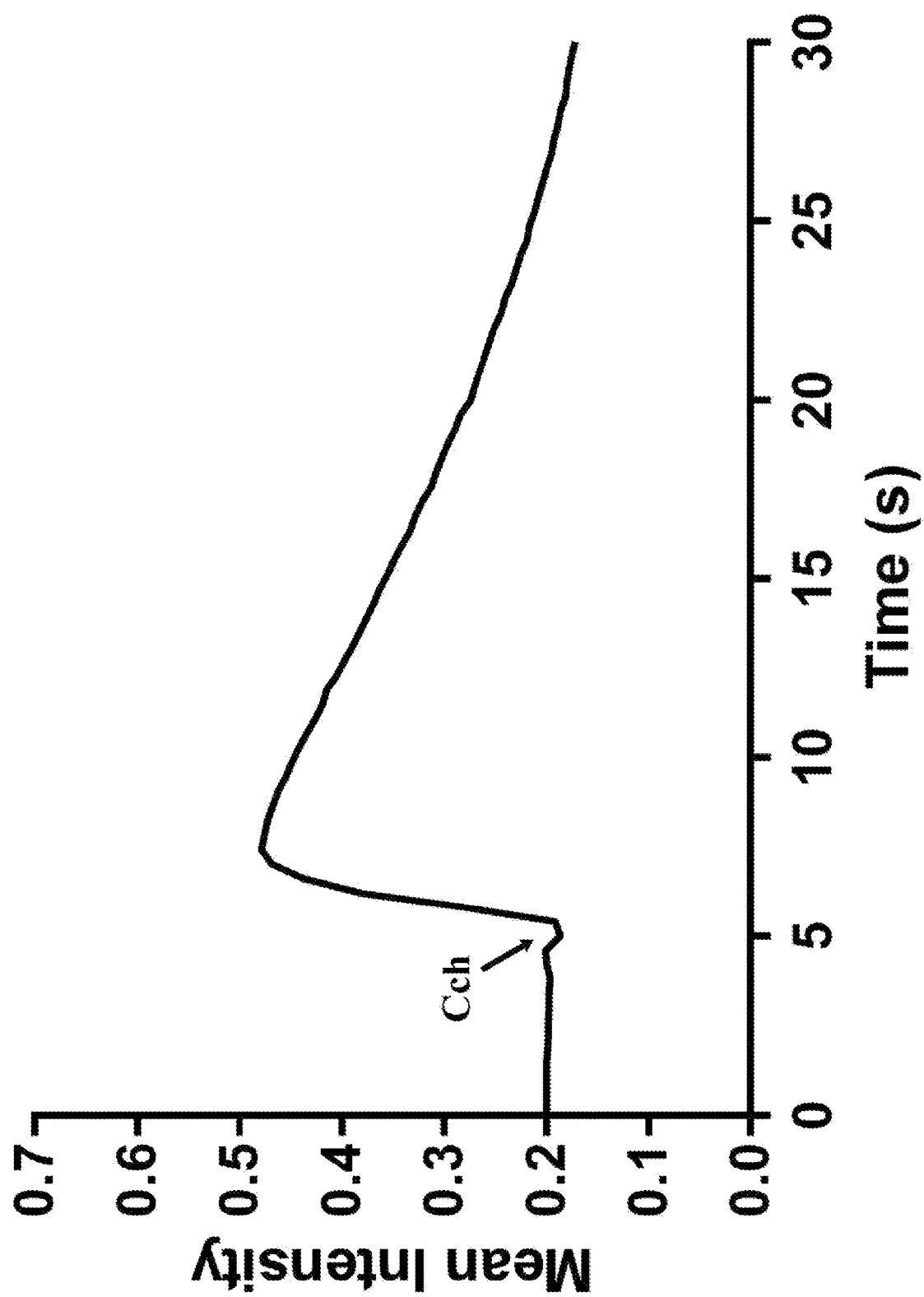
Figure 7E:
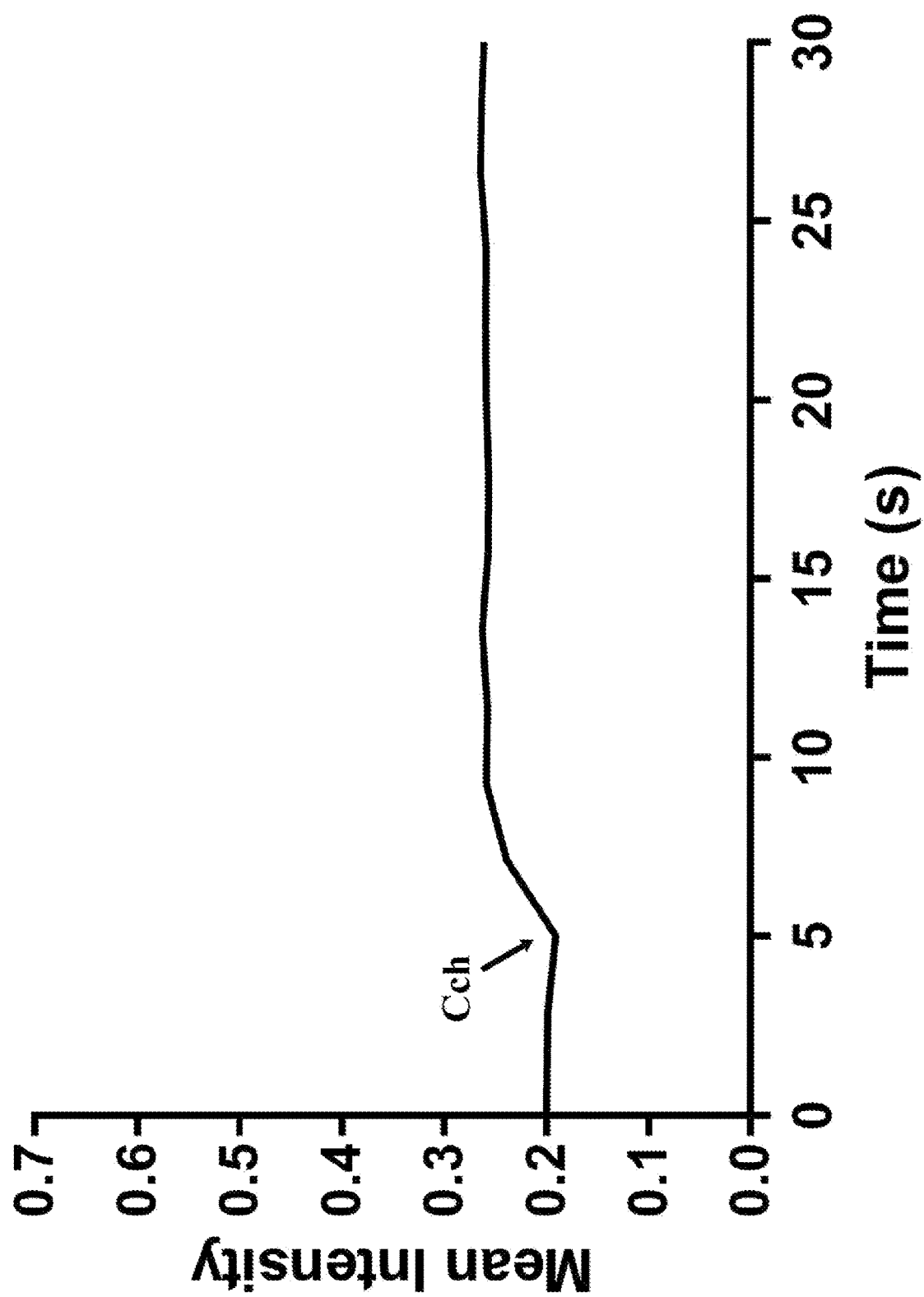
Figure 7F:
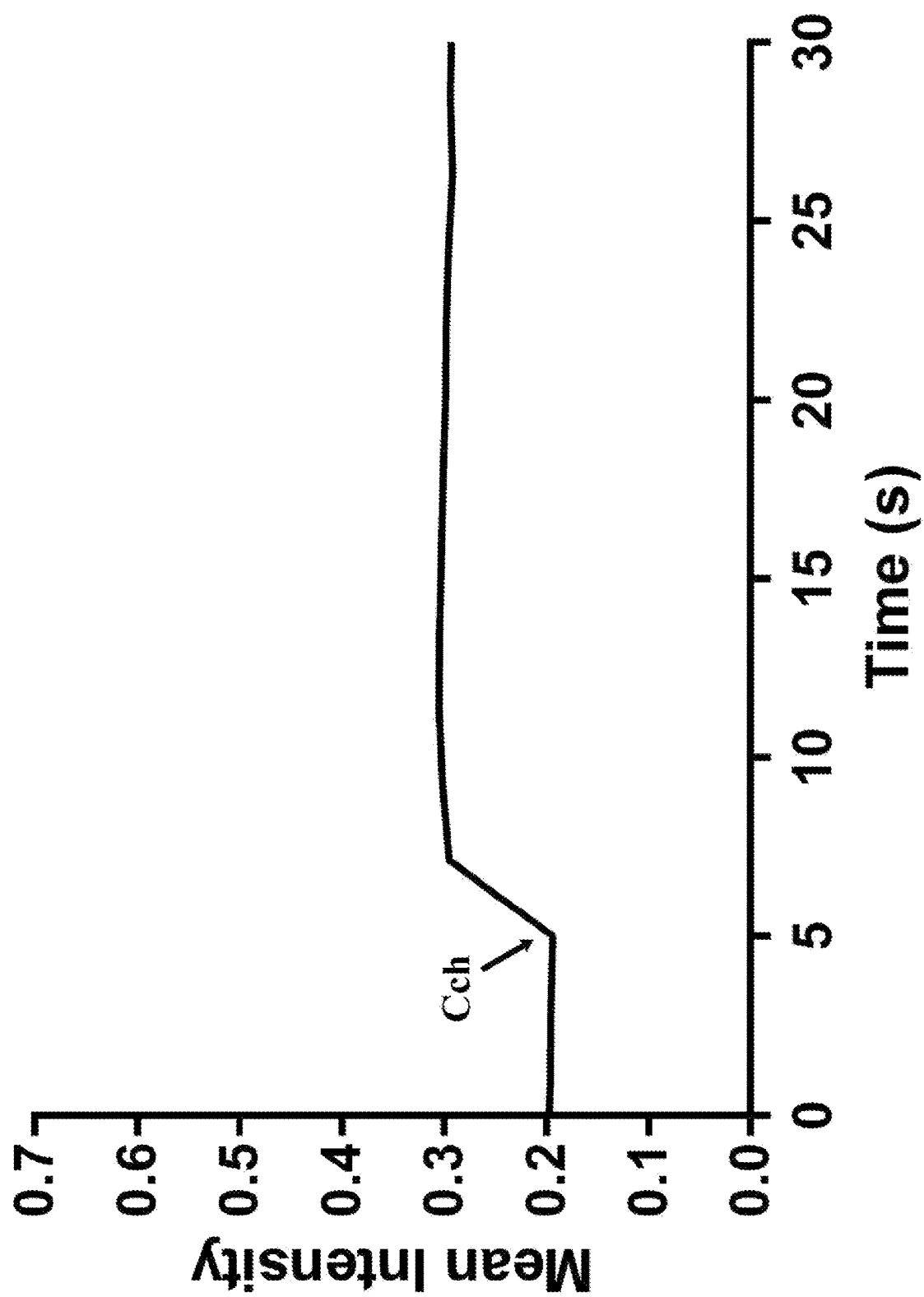
Figure 7G:
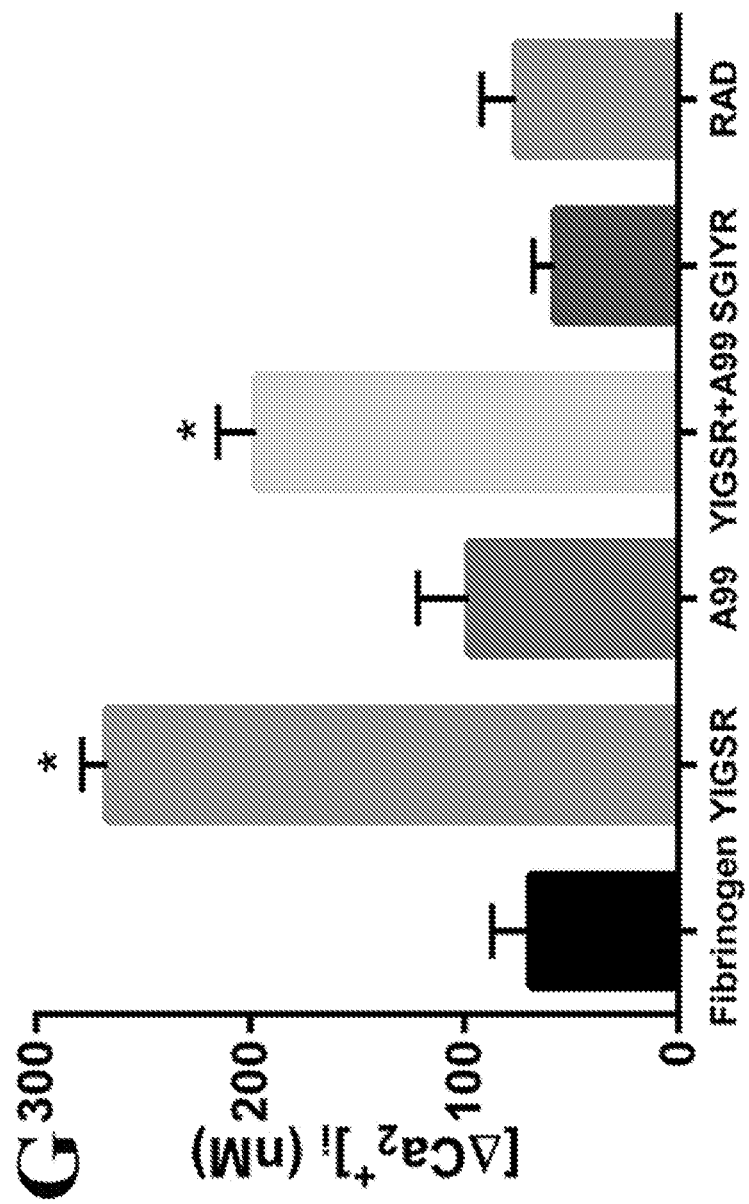

FIGS. 7A-F are a series of graphs depicting intracellular calcium concentration measurements after cells stimulation with 100 μM carbachol (Cch). Images were recorded and analyzed using Leica Application Suite X software. Par-C10 cells were plated on the following: unmodified FH (FIG. 7A), YIGSR-conjugated FH (FIG. 7B), A99-conjugated FH (FIG. 7C), a combination of YIGSR (50%)- and A99 (50%)-conjugated FH (FIG. 7D), SGIYR-conjugated FH (FIG. 7E), and RAD-conjugated FH (FIG. 7F). FIG. 7G is a bar chart showing that Par-C10 cells cultured on YIGSR-modified FH displayed increased $[Ca^{2+}]_i$. Data are expressed as means±SD, where *$p<0.01$ indicates a significant difference from control (unmodified FH).

Figure 8A:
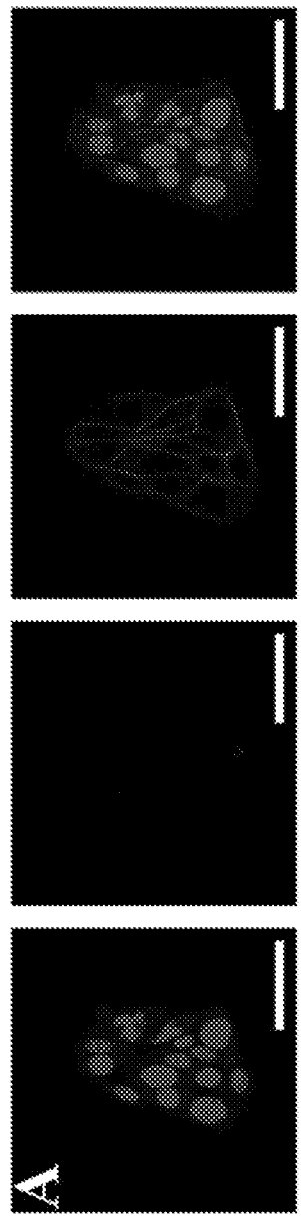
Figure 8B:
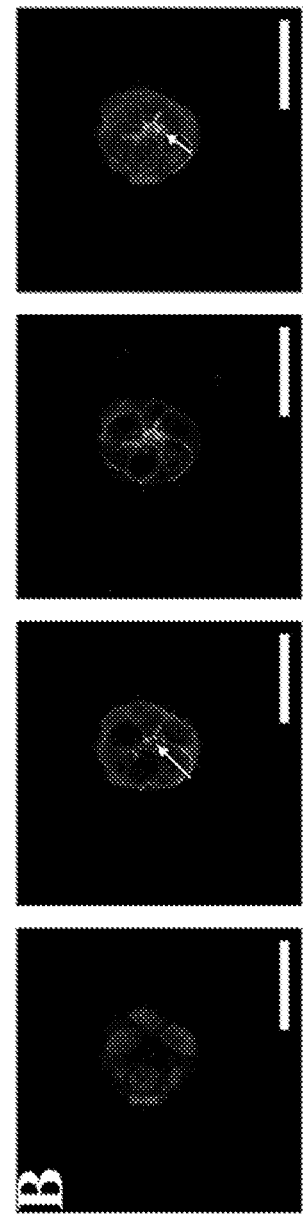
Figure 8C:
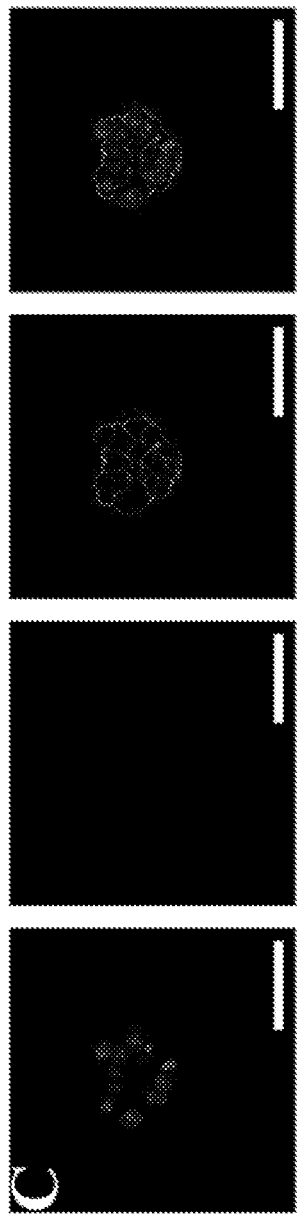
Figure 8D:
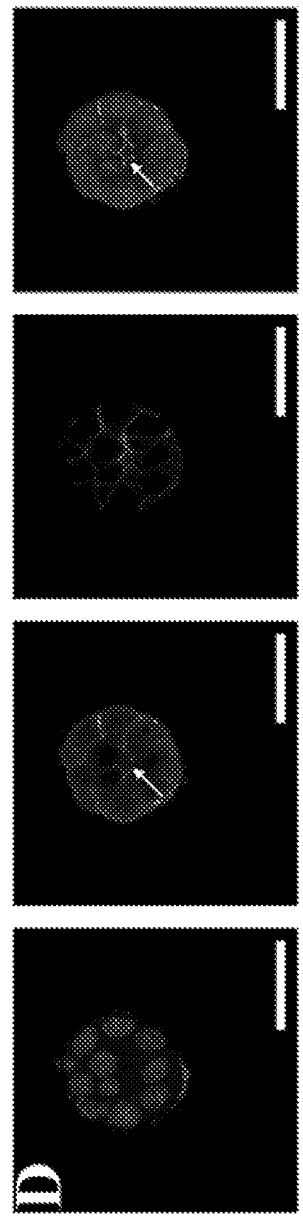
Figure 8E:
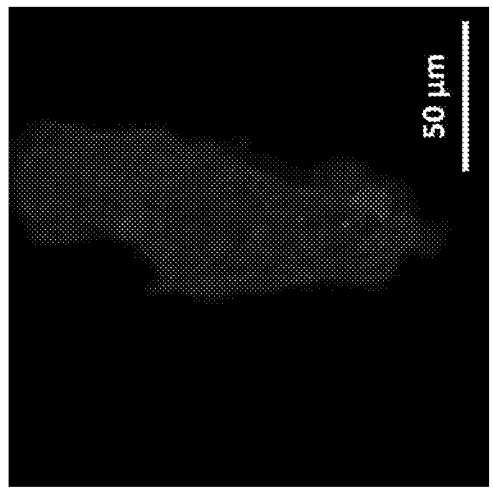
Figure 8E:
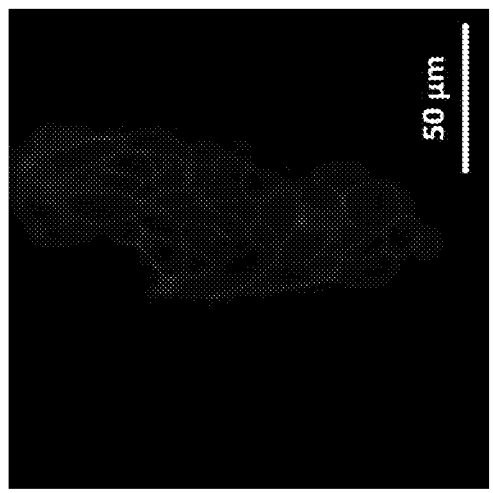
Figure 8E:
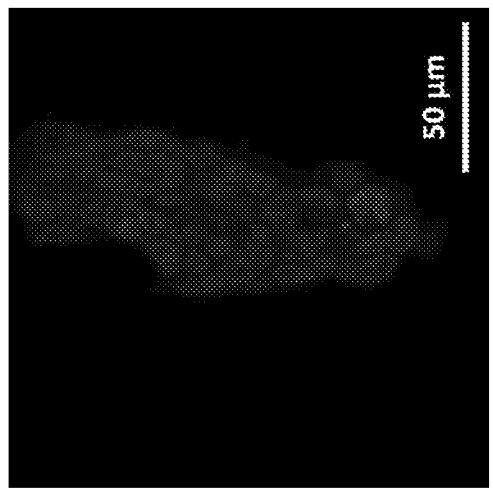

FIGS. 8A-E are a series of confocal microscopy images showing Par-C10 cells plated on unmodified FH (FIG. 8A), YIGSR-conjugated FH (FIG. 8B), A99-conjugated FH (FIG. 8C), a combination of YIGSR (50%)- and A99 (50%)-conjugated FH (FIG. 8D), and L1 peptide AG73 (CG-GRKRLQVQLSIRT-amide; SEQ ID NO: 5) (FIG. 8E). Scale bars represent 50 μm. White arrows indicate lumen formation. The first images of FIGS. 8A-8E (i.e., the leftmost images) show the nuclei as stained by TO-PRO-3 iodide (blue). The second images of FIGS. 8A-8D (i.e., the left-center images) show ZO-1 as stained by Alexa Fluor 488-conjugated goat anti rabbit secondary antibody (green). The third images of FIGS. 8A-D (i.e., the right-center images) and the second image of FIG. 8E (i.e., the center image) show F-actin as stained by Alexa Fluor 568-conjugated phalloidin (red). The fourth images of FIGS. 8A-D (i.e., the rightmost images) and the third image of FIG. 8E (i.e., the rightmost image) are merged images showing all the stained structures (multicolored). All images were obtained and analyzed using a Carl Zeiss 700 LSM confocal microscope.

Figure 9:
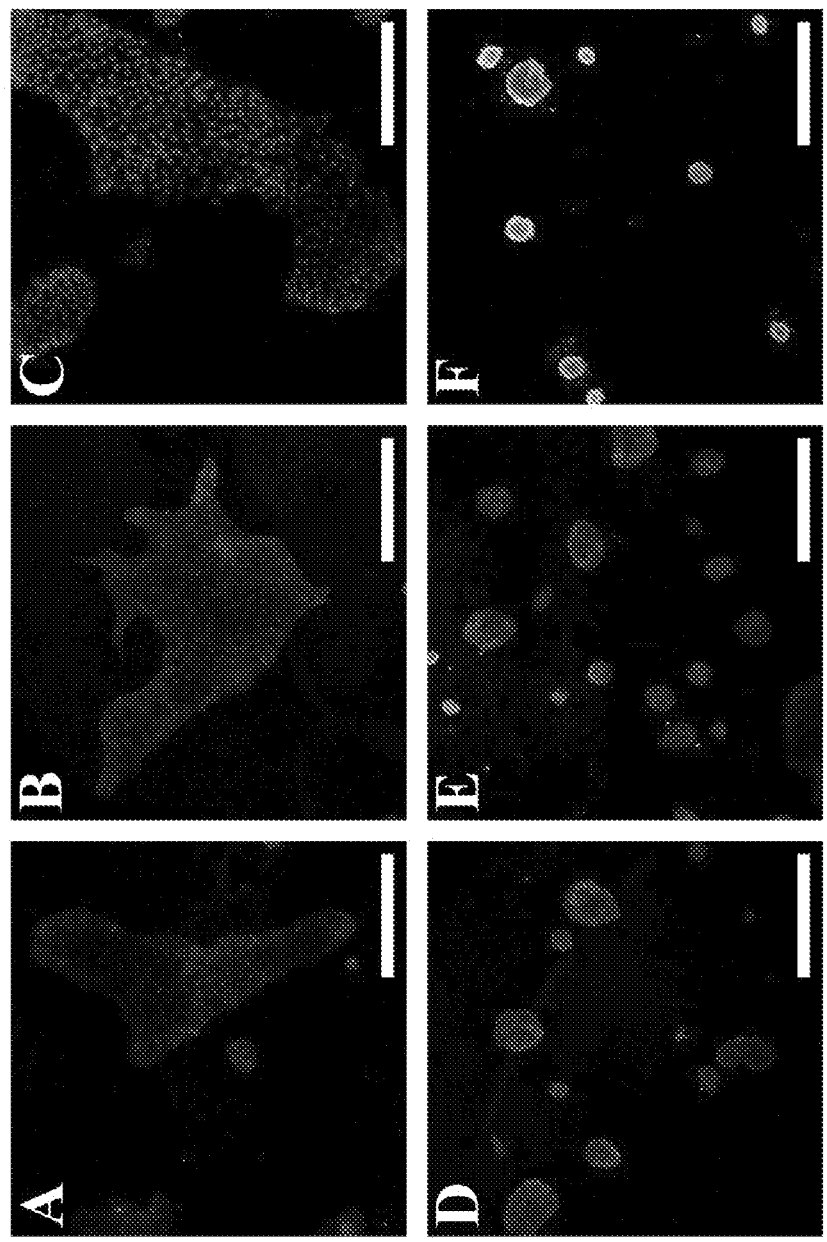

FIG. 9 is a series of confocal microscopy images at low magnification (10×) and maximum intensity projection showing Par-C10 cells plated on the following: unmodified FH (A), SGIYR-conjugated FH (B), RAD-conjugated FH (C), YIGSR-conjugated FH (D), A99-conjugated FH (E), and a combination of YIGSR (50%)- and A99 (50%)-conjugated FH (F). Scale bars represent 200 μm. The images show ZO-1 as stained by Alexa Fluor 488-conjugated goat anti-rabbit secondary antibody (green), F-actin as stained by Alexa Fluor 568-conjugated phalloidin (red), and nuclei as stained by TO-PRO-3 iodide (blue).

Figure 10A:
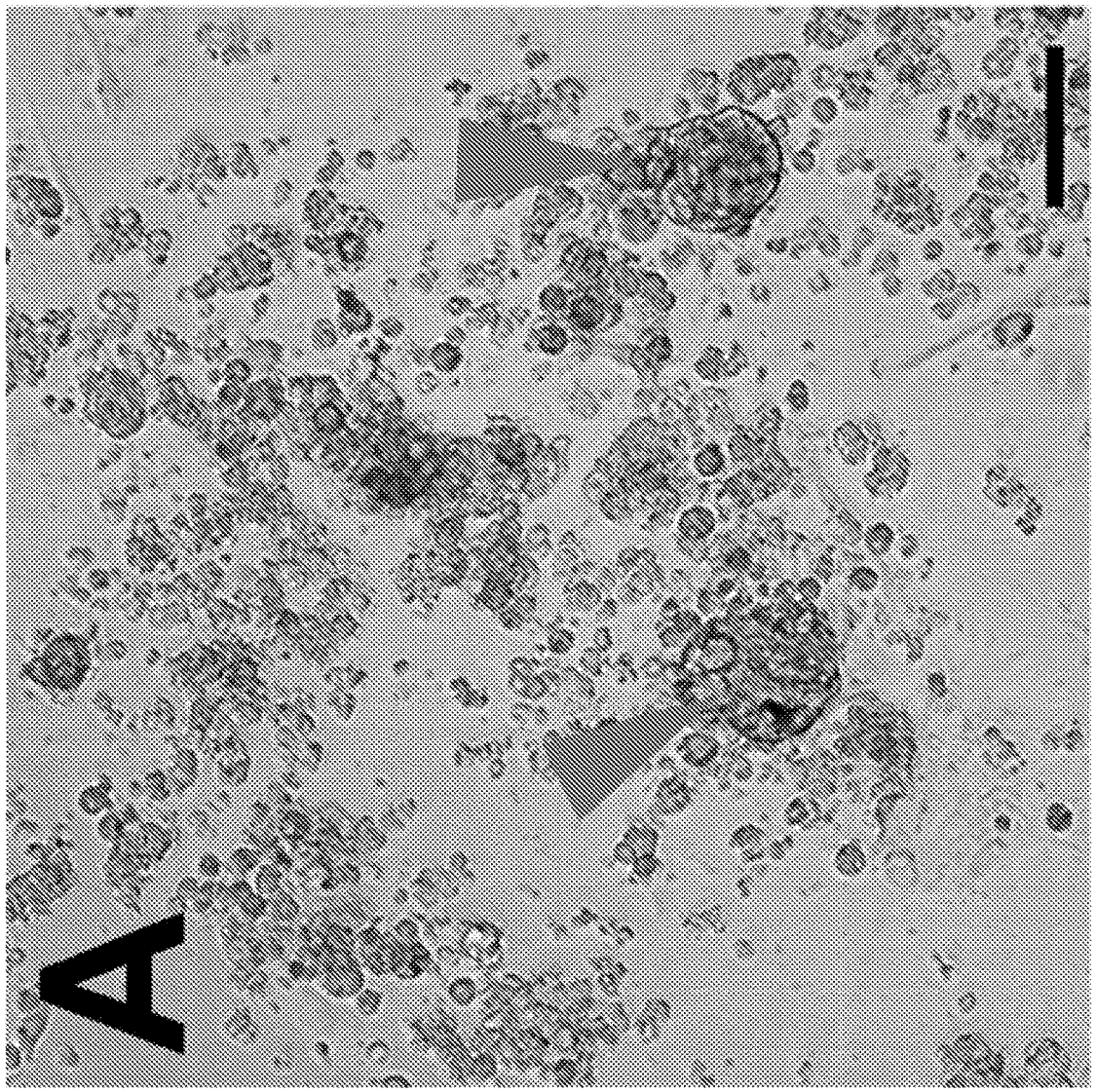
Figure 10B:
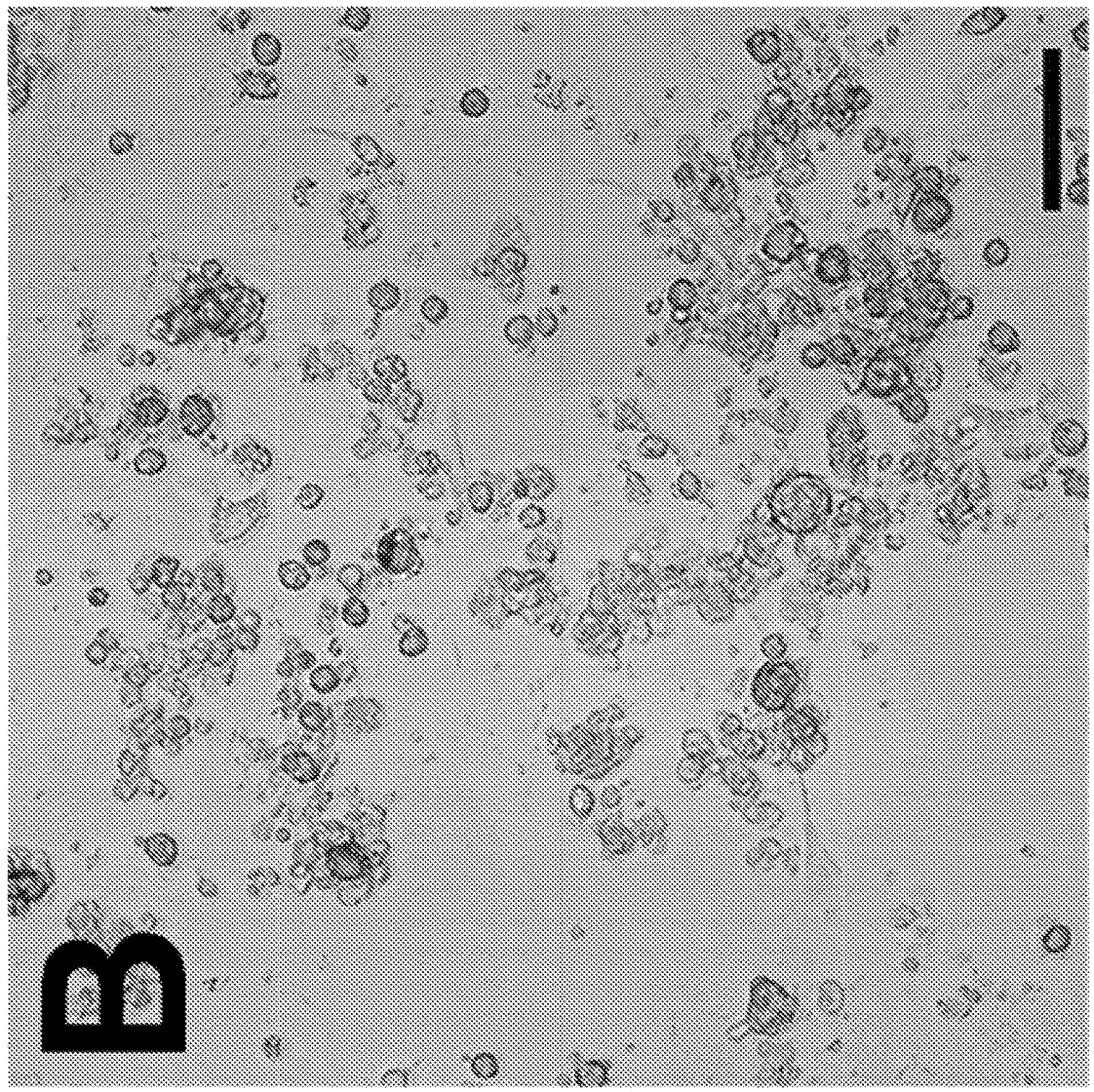
Figure 10C:
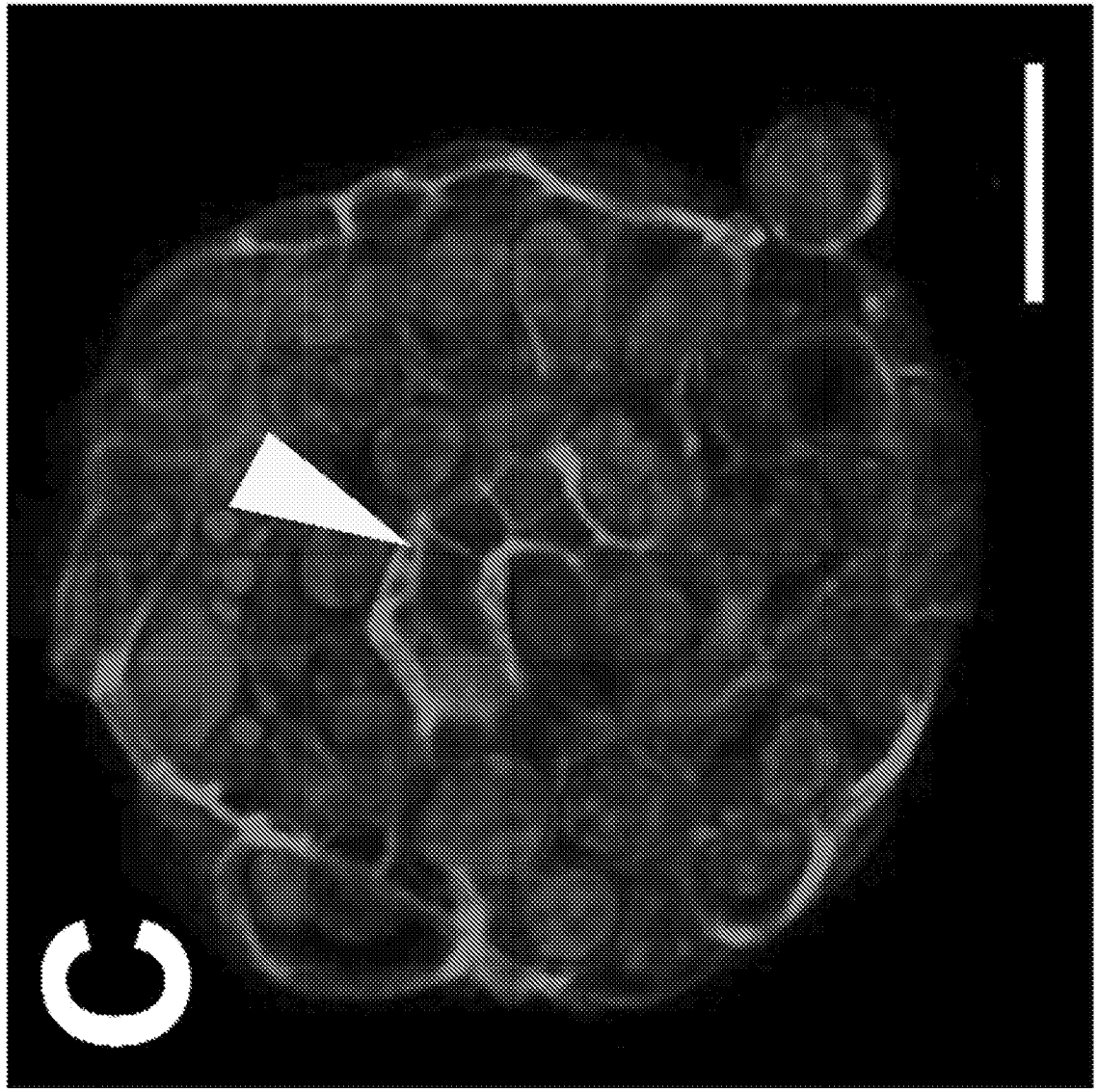
Figure 10D:
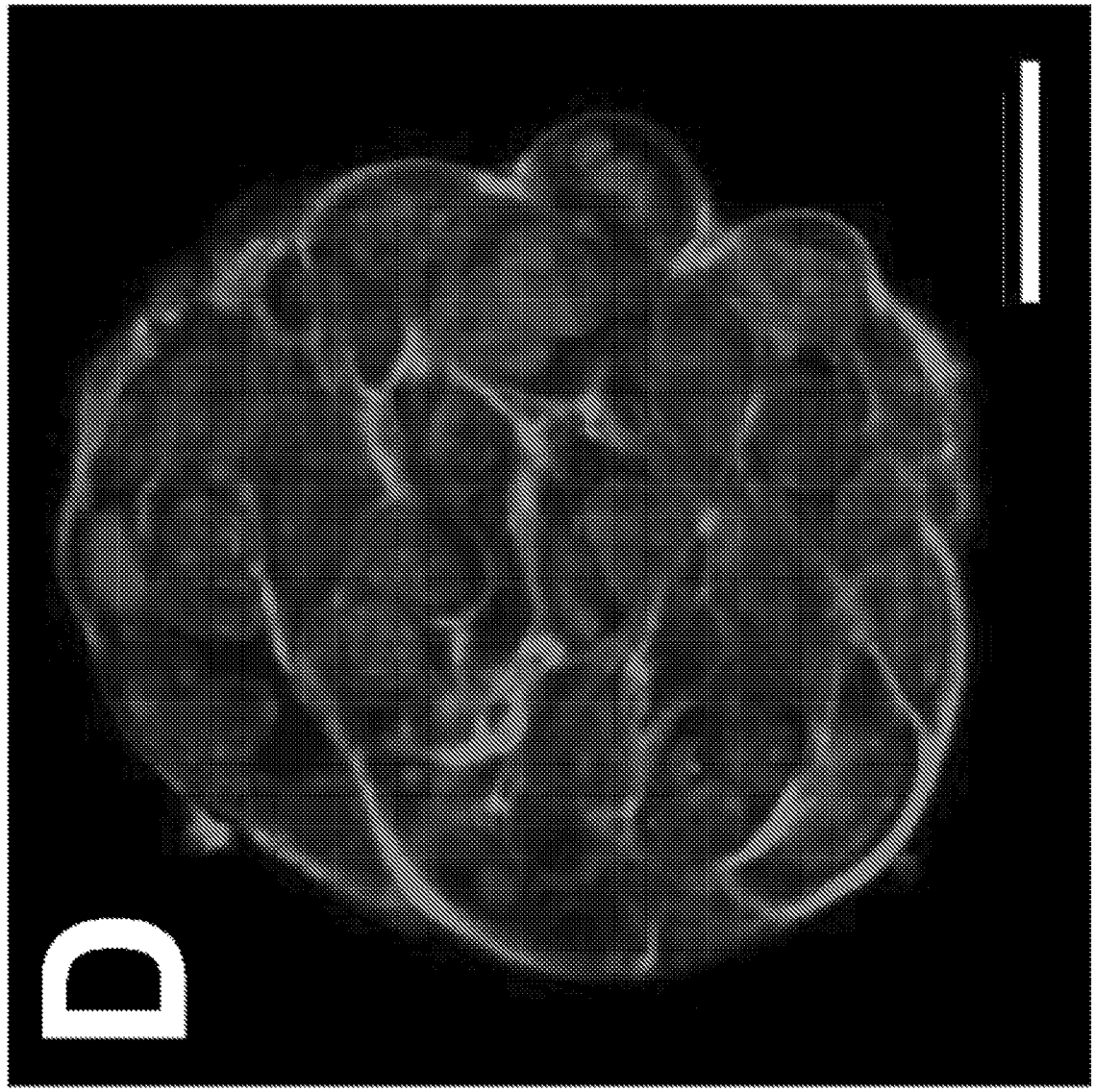
Figure 10E:
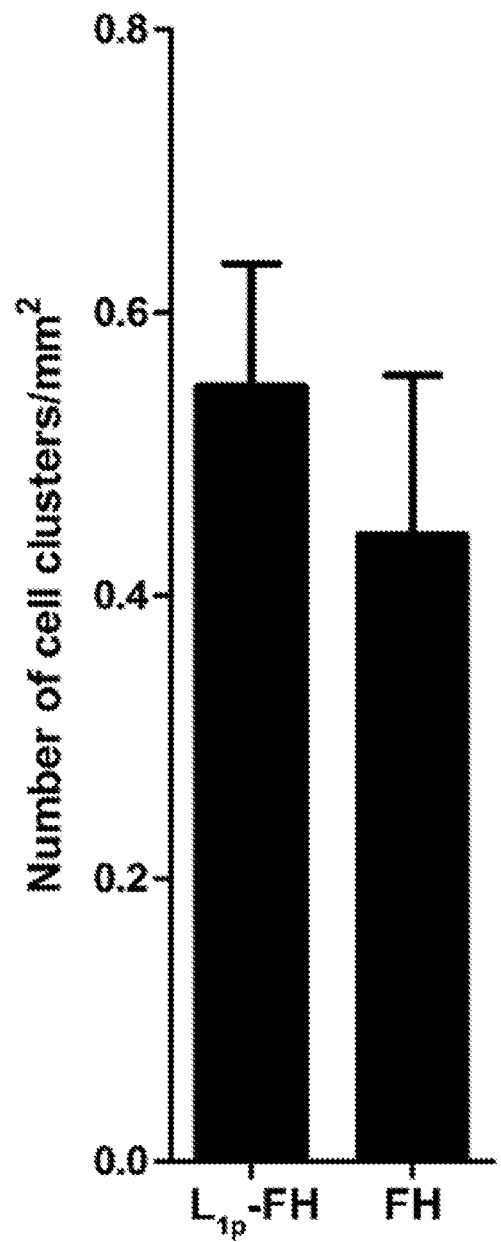

FIGS. 10A-D are a series of images of mSMG cell clusters grown on $L_{1p}$-FH (FIG. 10A and FIG. 10C) or FH (FIG. 10B and FIG. 10D) for six days. Images were taken using an EVOS XL Core with a 4× objective (FIG. 10A and FIG. 10B) or a confocal Zeiss LSM 700 microscope with 20× objective (FIG. 10C and FIG. 10D) to visualize acinar organization (red: F-actin, blue: nucleus). Scale bars represent 100 μm (FIG. 10A and FIG. 10B) or 20 μm (FIG. 10C and FIG. 10D) in length. FIG. 10E is a graph showing mSMG cell cluster formation calculation. Red arrowheads indicate cell clusters, and yellow arrowhead indicates cell cluster lumen.

Figure 11:
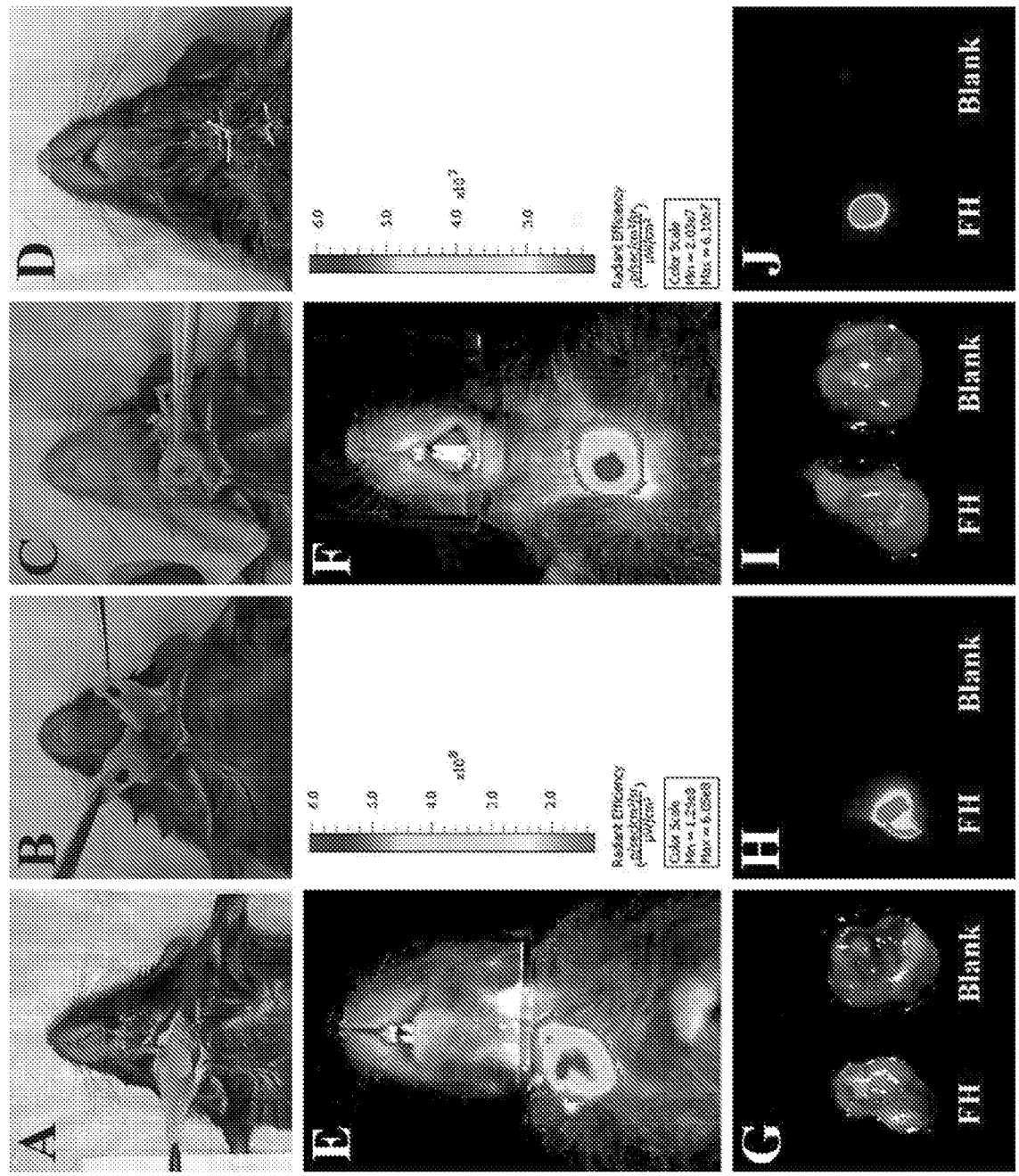

FIG. 11 is a series of images depicting a surgical procedure to create wounded mouse SMG and monitoring of hydrogel stability in vivo. mSMG were exposed and a surgical wound was created on both glands using a 3 mm diameter biopsy punch (A and B). FH scaffolds were injected into the surgical wound where a coverslip was placed underneath to prevent leakage (C). The incision was closed with an interrupted 4-0 suture (D). FH stability was monitored in a Xenogen IVIS 100 Bioluminescent Imager at day 3 (E) and at day 8 (F). Mouse submandibular glands were dissected and the fluorescent intensity was corroborated using a CHEMI-DOC™ System at day 3 (G and H) and at day 8 (I and J). A total of n=5 mice per group were tested.

Figure 12:
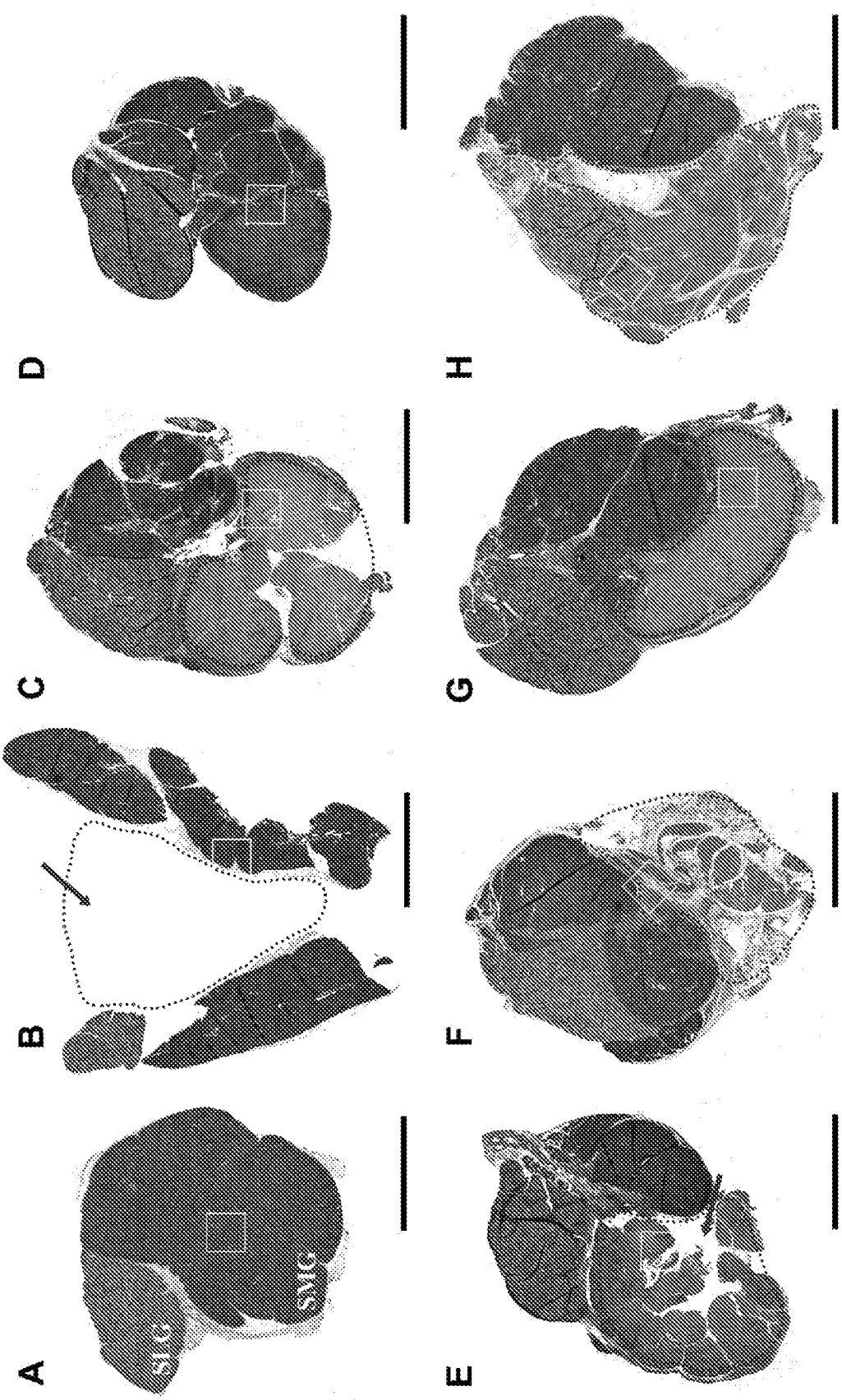

FIG. 12 is a series of images showing hematoxylin and eosin stained histological sections of non-wounded (A: day 0), wounded mSMG without scaffold (B: day 0), wounded mSMG with $L_{1p}$-FH$^{680}$ (C: day 3, and D: day 8), wounded mSMG without scaffold (E: day 3, and F: day 8) and wounded mSMG with FH$^{680}$ (G: day 3, H: day 8). Blue dotted areas are wounded areas. Scale bars represent 2 mm.

SMG means submandibular gland and SLG means sublingual gland. Representative image from a total of n=5 mice per group.

Figure 13:
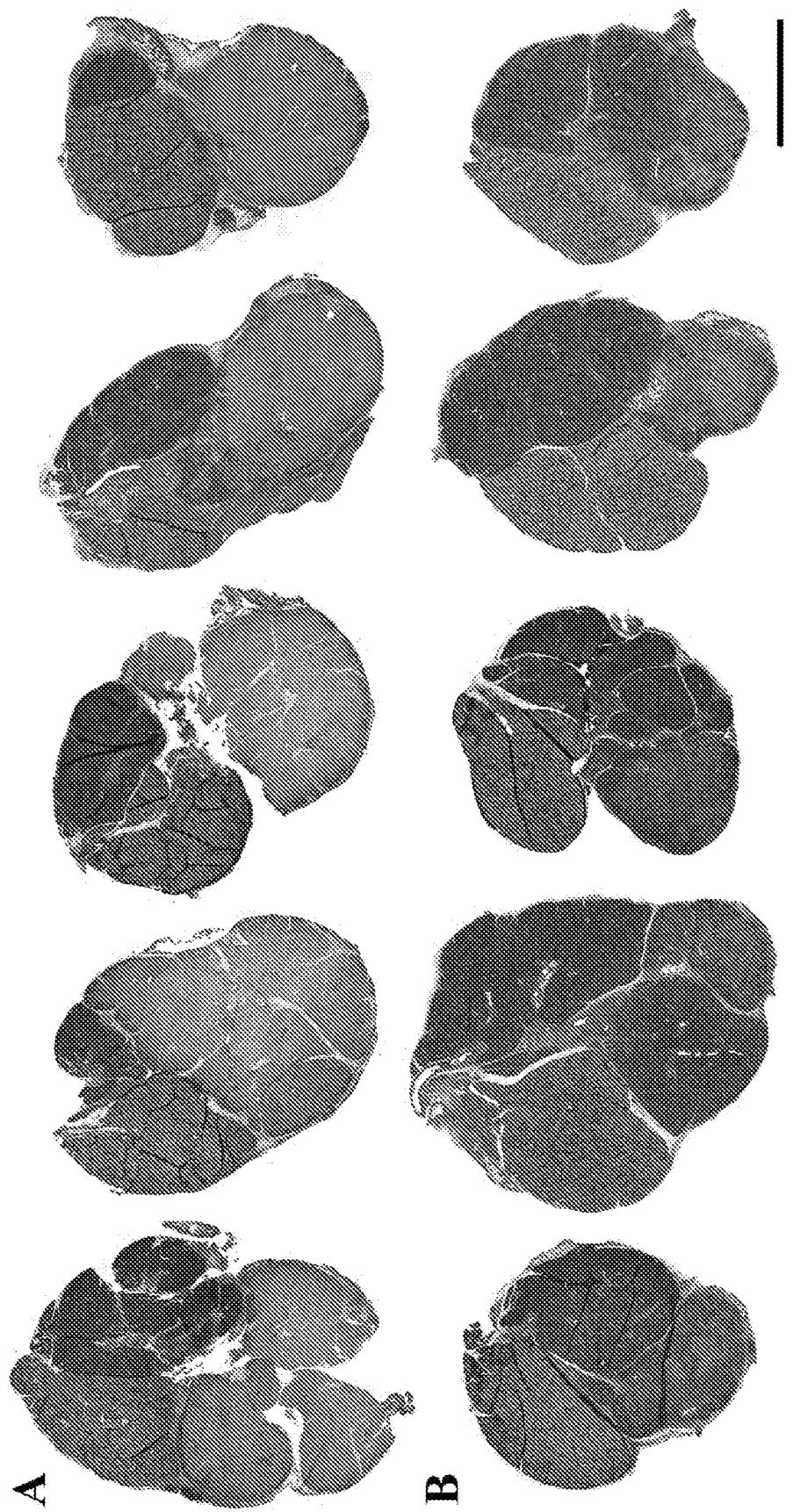

FIG. 13 is a series of images showing hematoxylin and eosin stained histological sections of wounded mSMG with $L_{1p}$-FH$^{680}$ (A: day 3, and B: day 8). Tiled images generated were by Leica DMI6000B system. Magnification 10×, bars=2 mm.

Figure 14:
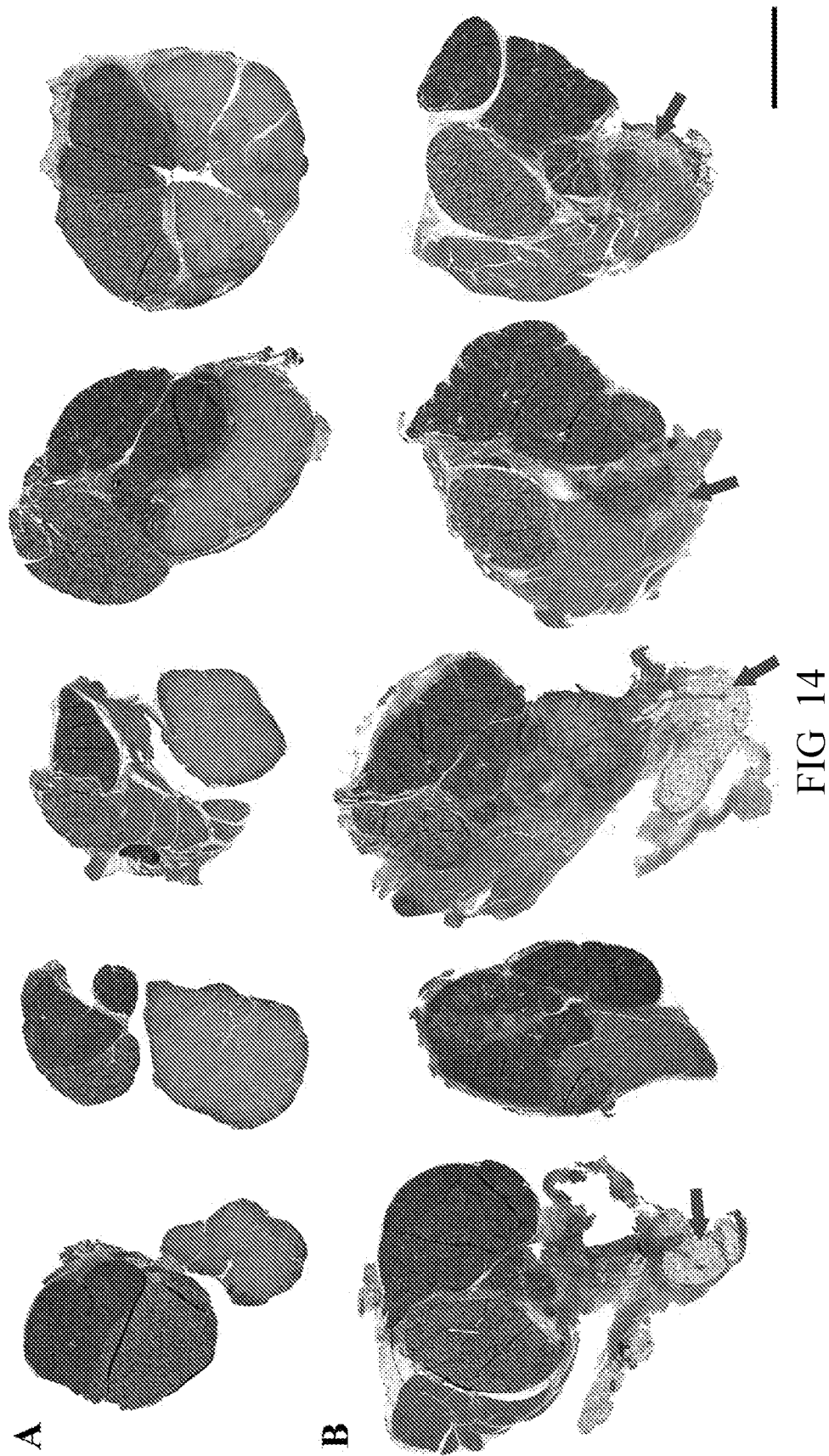

FIG. 14 is a series of images showing hematoxylin and eosin (H&E) stained histological sections of wounded mSMG with FH$^{680}$ (A; day 3, B; day 8). Tiled images were generated by Leica DMI6000B system. Magnification 10×, bars=2 mm.

Figure 15A:
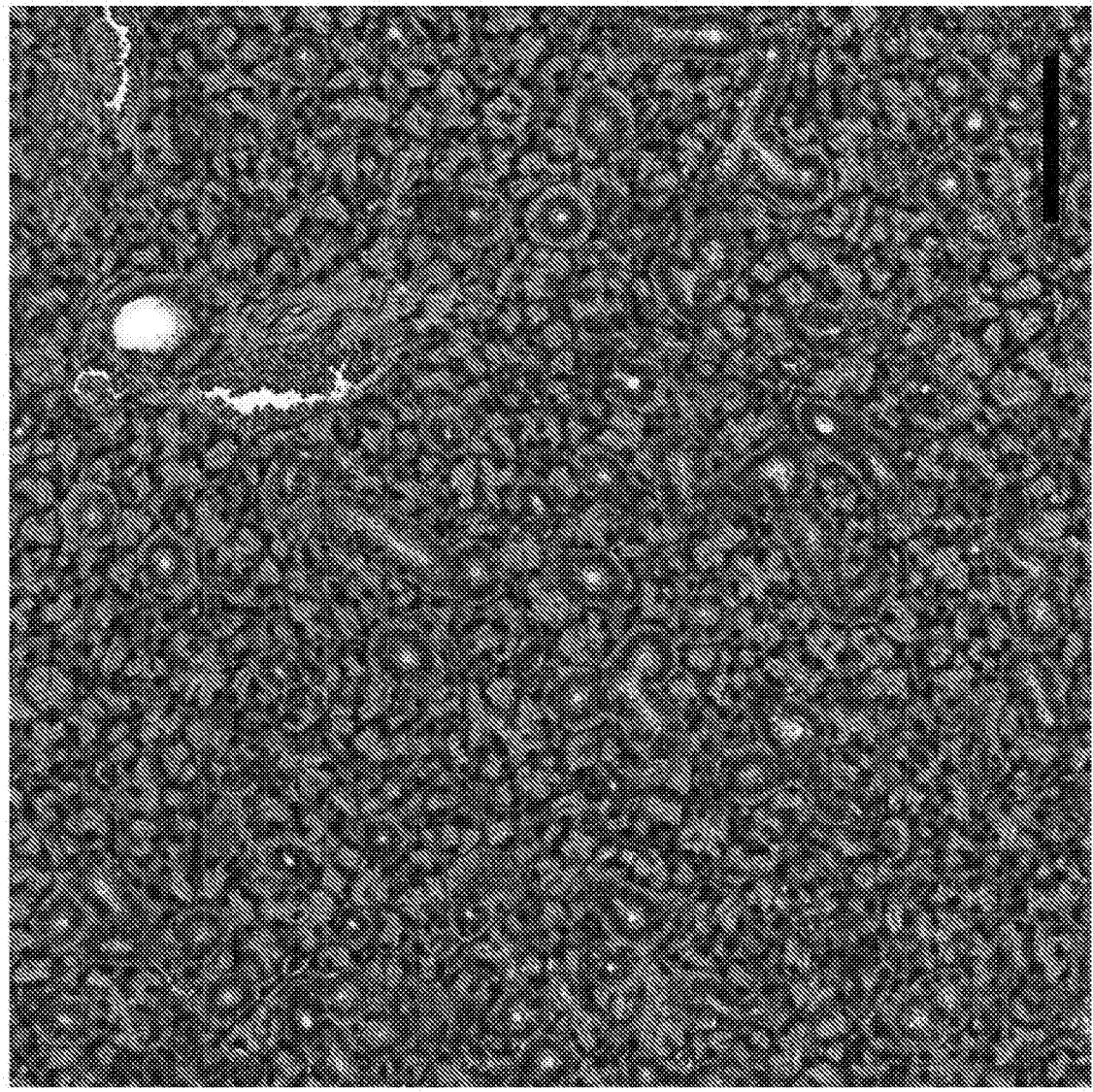
Figure 15B:
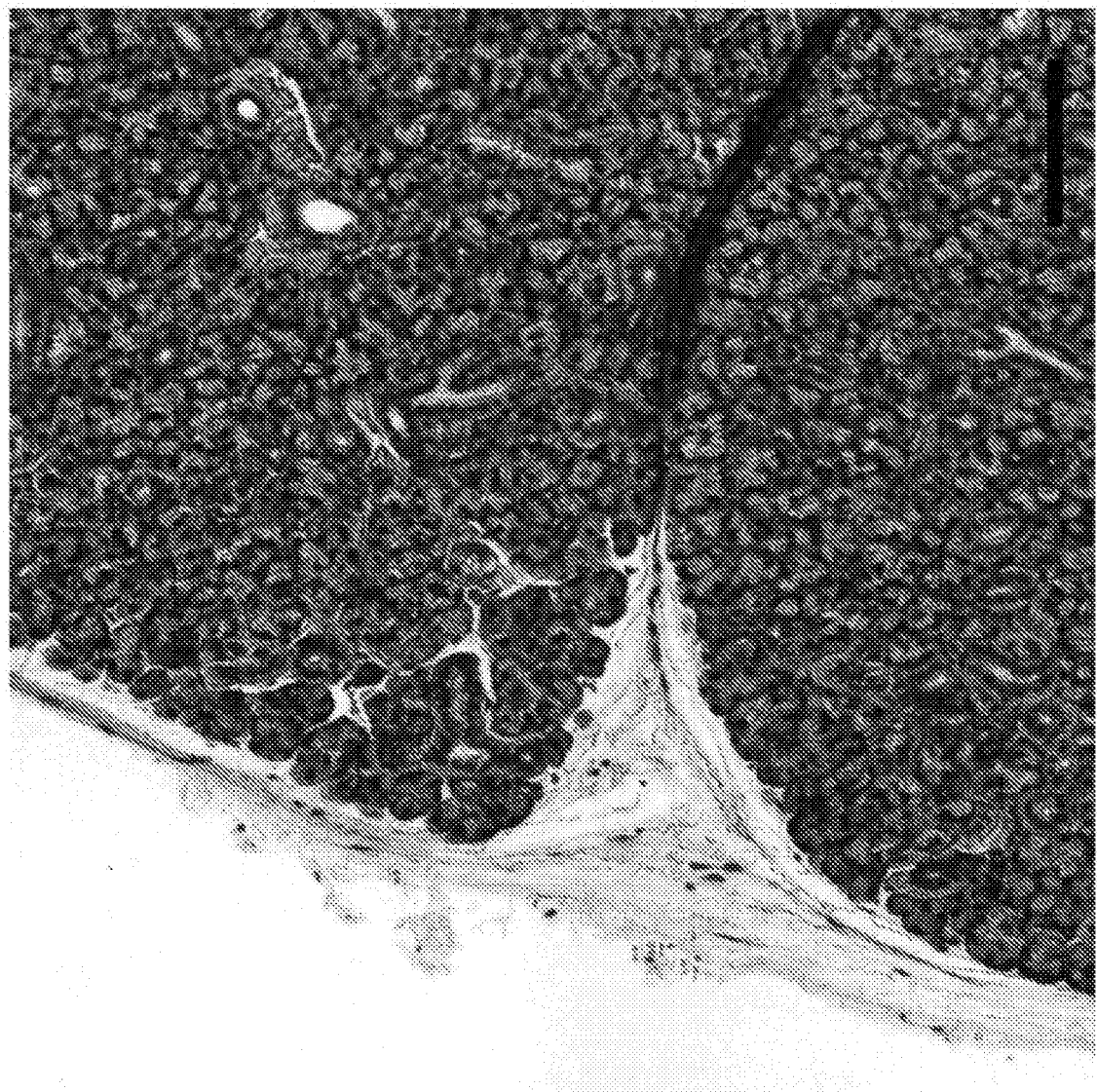
Figure 15C:
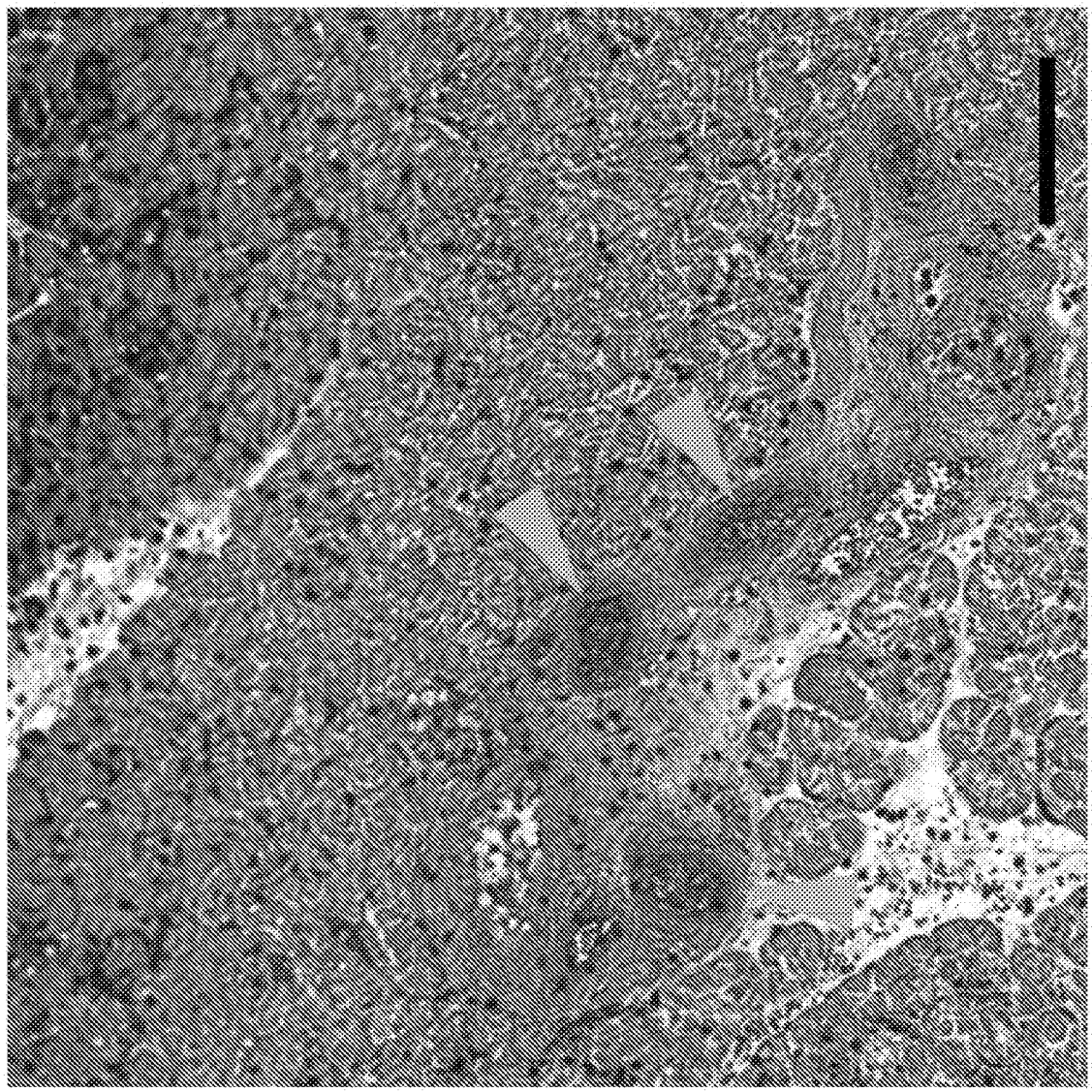
Figure 15D:
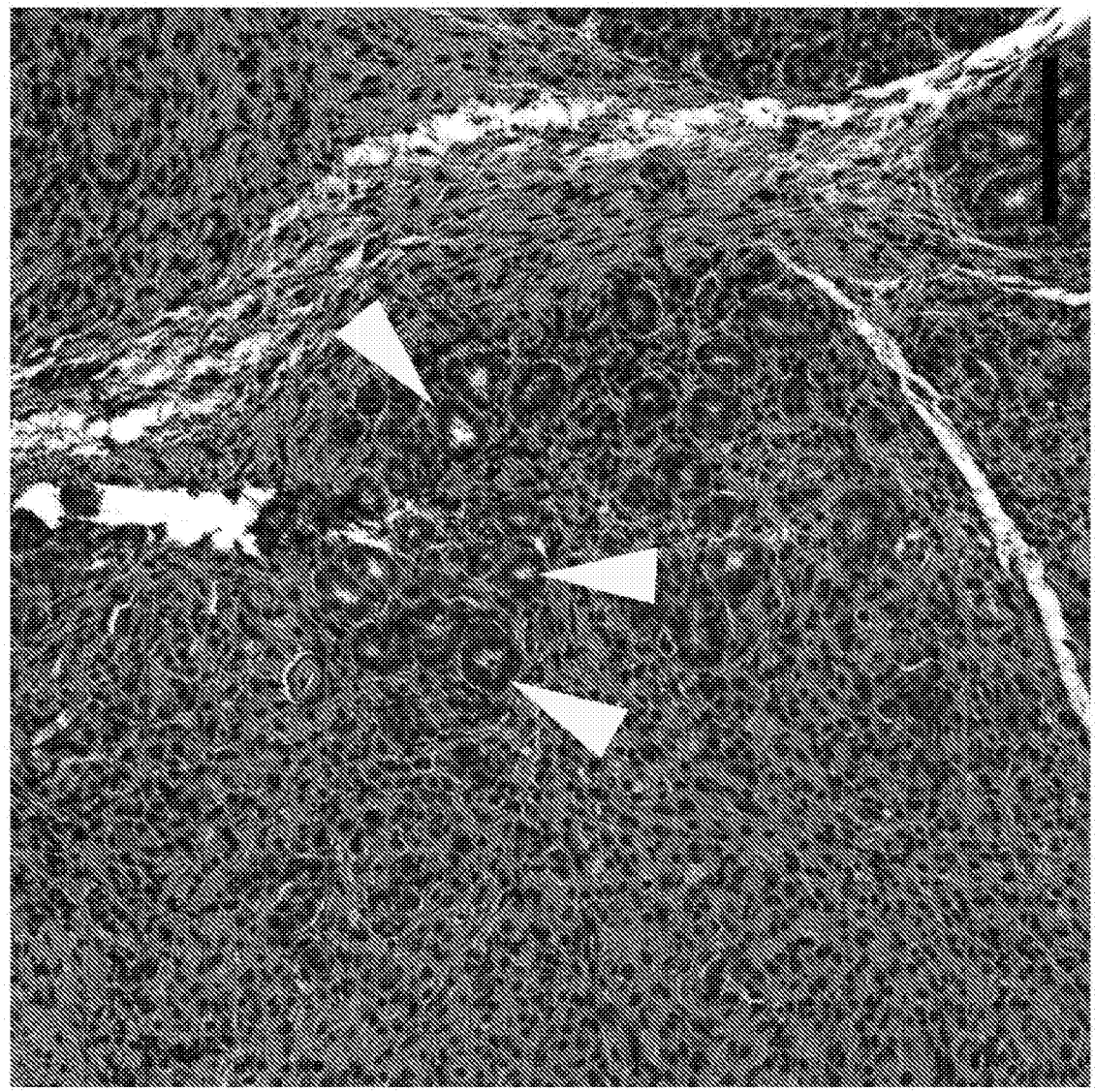
Figure 15E:
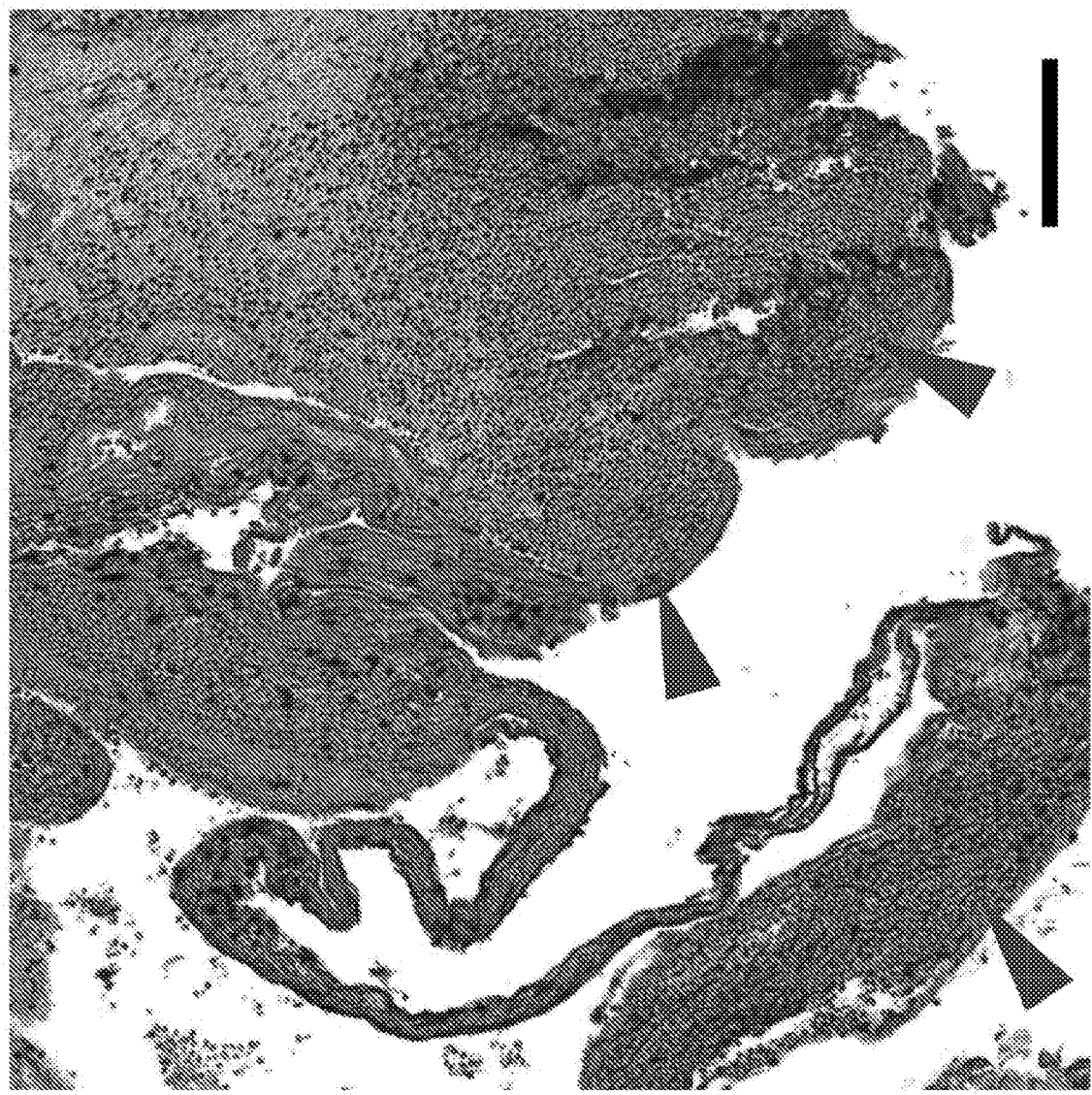
Figure 15F:
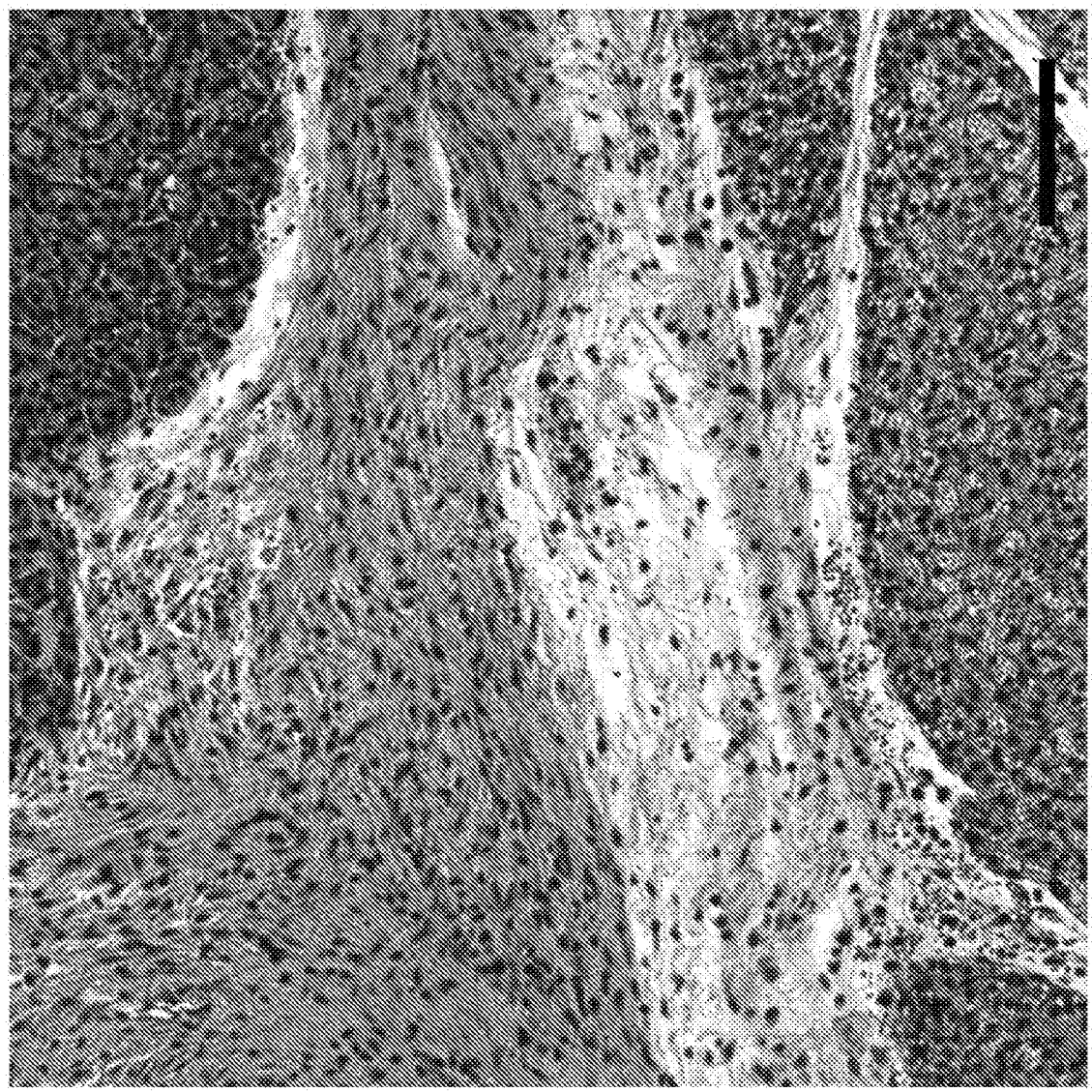
Figure 15G:
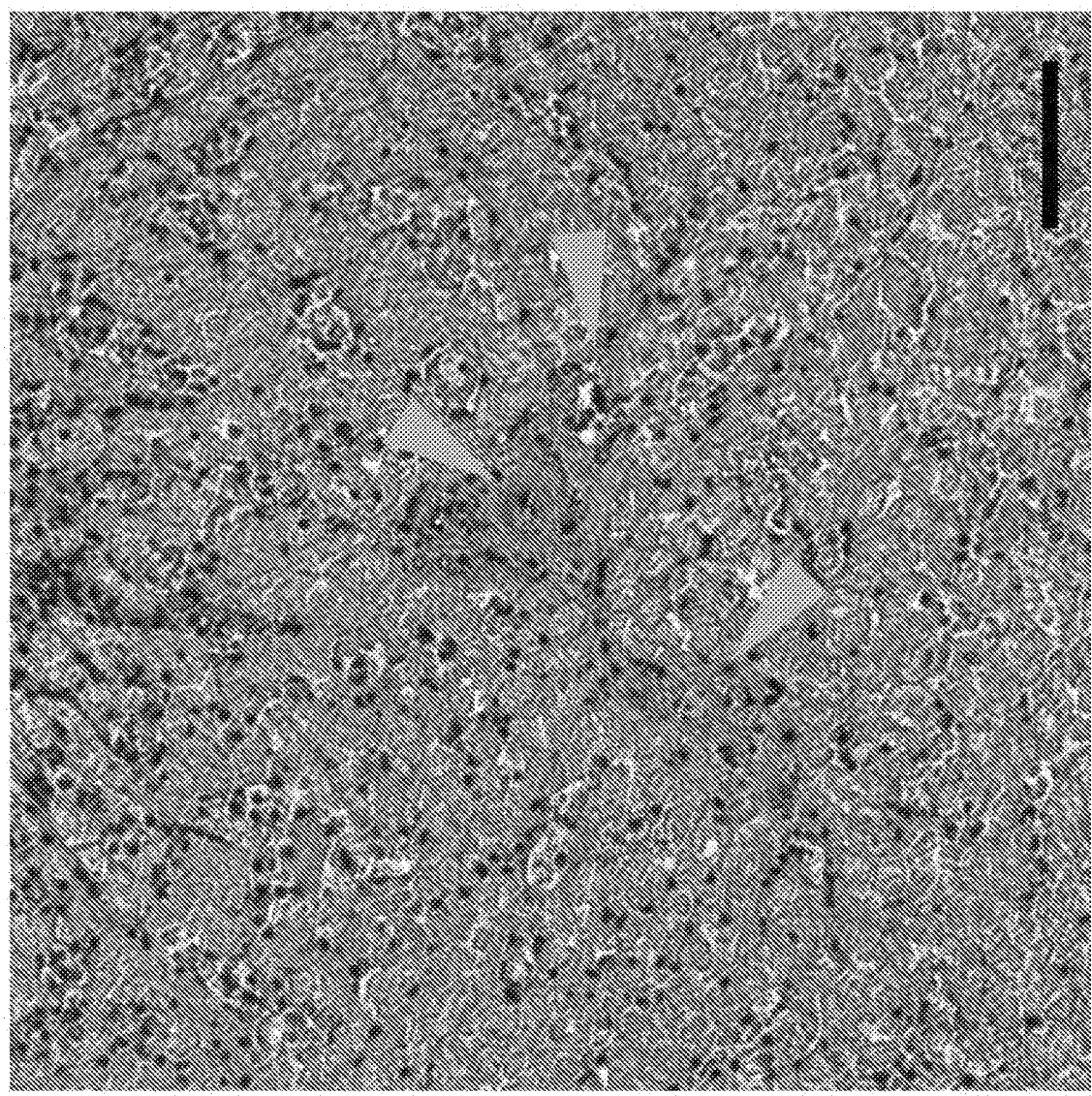
Figure 15H:
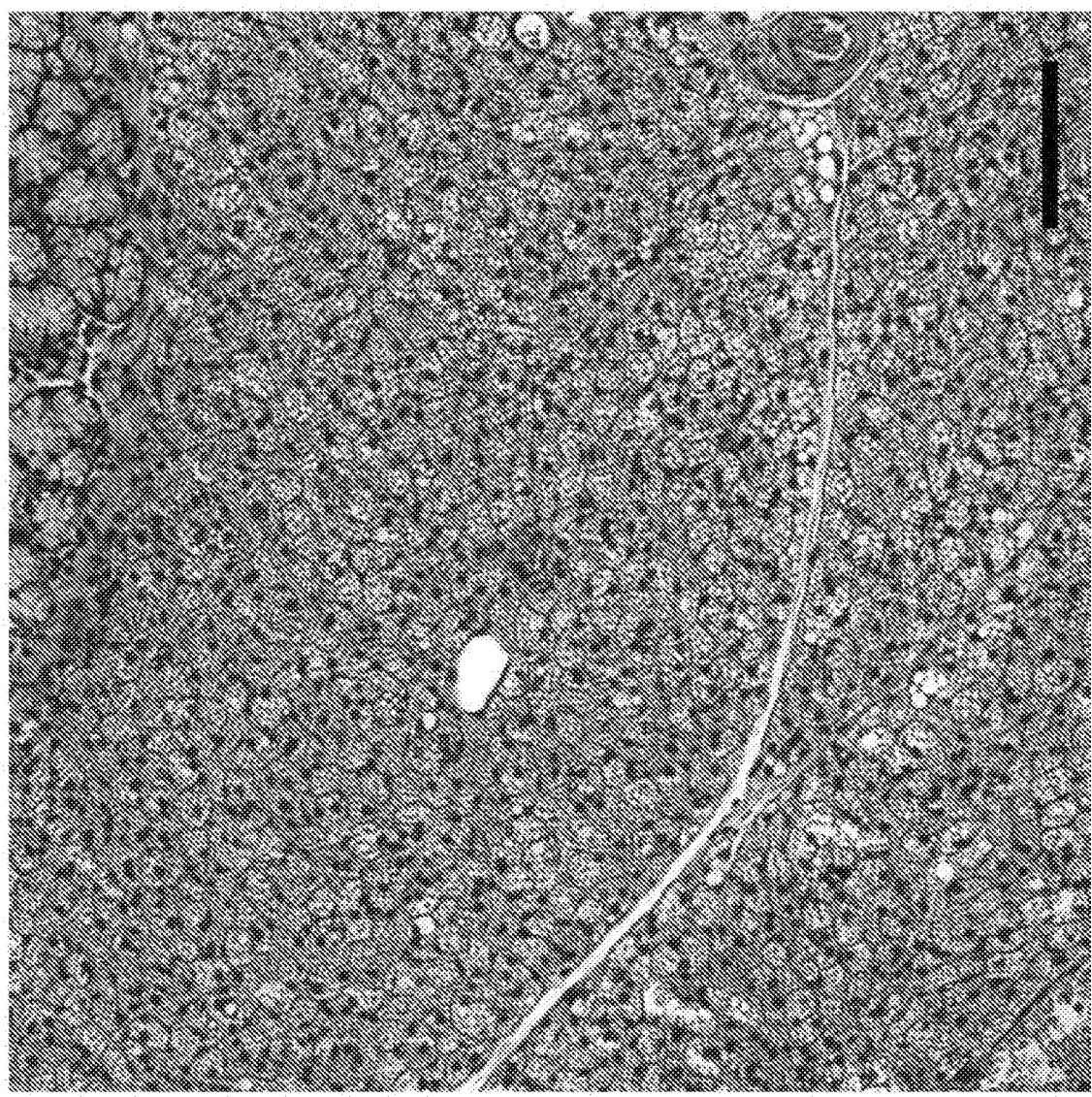

FIGS. 15A-H are a series of images showing hematoxylin and eosin (H&E) stained sections of mSMG treated with and without FH scaffolds (magnification 10× from FIG. 12 yellow boxes). Shown are native mSMG (FIG. 15A: day 0), wounded mSMG without scaffold (FIG. 15B: day 0), wounded mSMG with $L_{1p}$-FH$^{680}$ (FIG. 15C: day 3, FIG. 15D: day 8), wounded mSMG without scaffold (FIG. 15E: day 3, FIG. 15F: day 8) and wounded mSMG with FH$^{680}$ (FIG. 15G: day 3, FIG. 15H: day 8). Scale bars represent 100 μm. Representative image from a total of n=5 mice per group.

Figure 16:
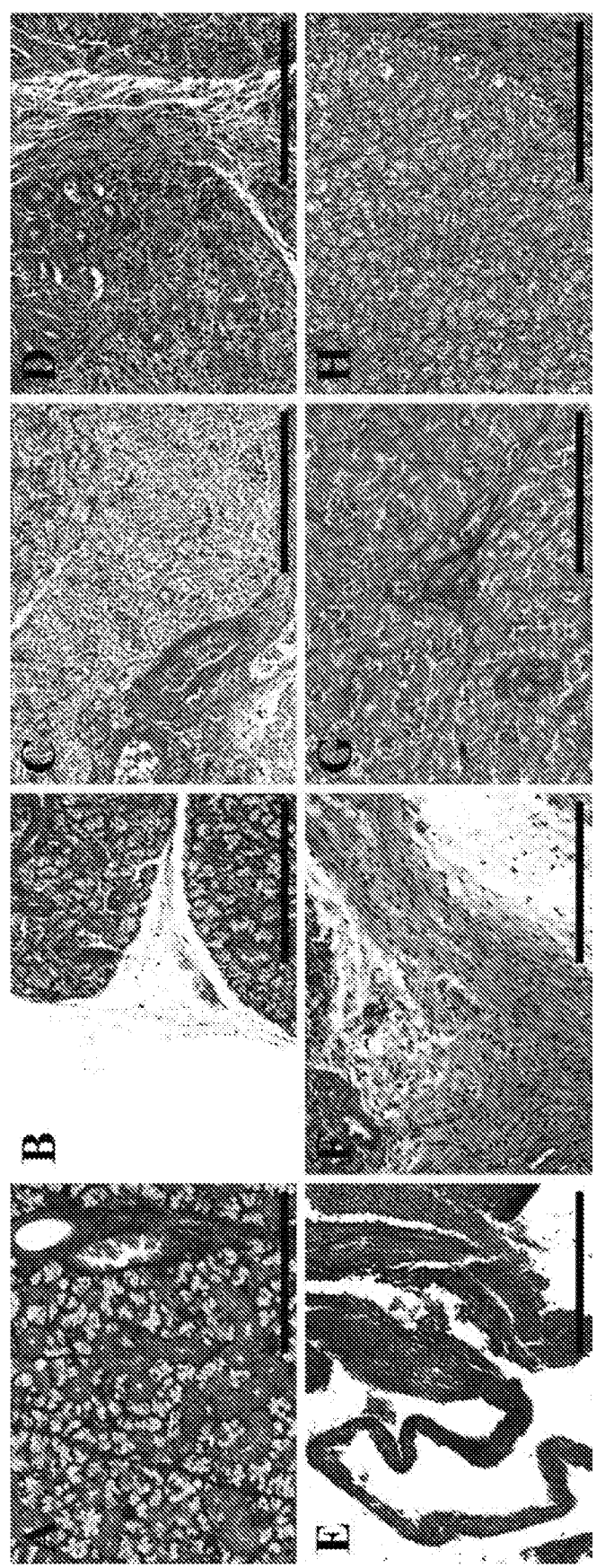

FIG. 16 is a series of Masson's trichrome stain images of mSMG treated with and without scaffolds. Shown are native mSMG (A: day 0), wounded mSMG without scaffold (B: day 0), wounded mSMG with $L_{1p}$-FH$^{680}$ (C: day 3, D: day 8), wounded mSMG without scaffold (E: day 3, F: day 8) and wounded mSMG with FH$^{680}$ (G: day 3, H: day 8). Scale bars represent 200 μm.

Figure 17:
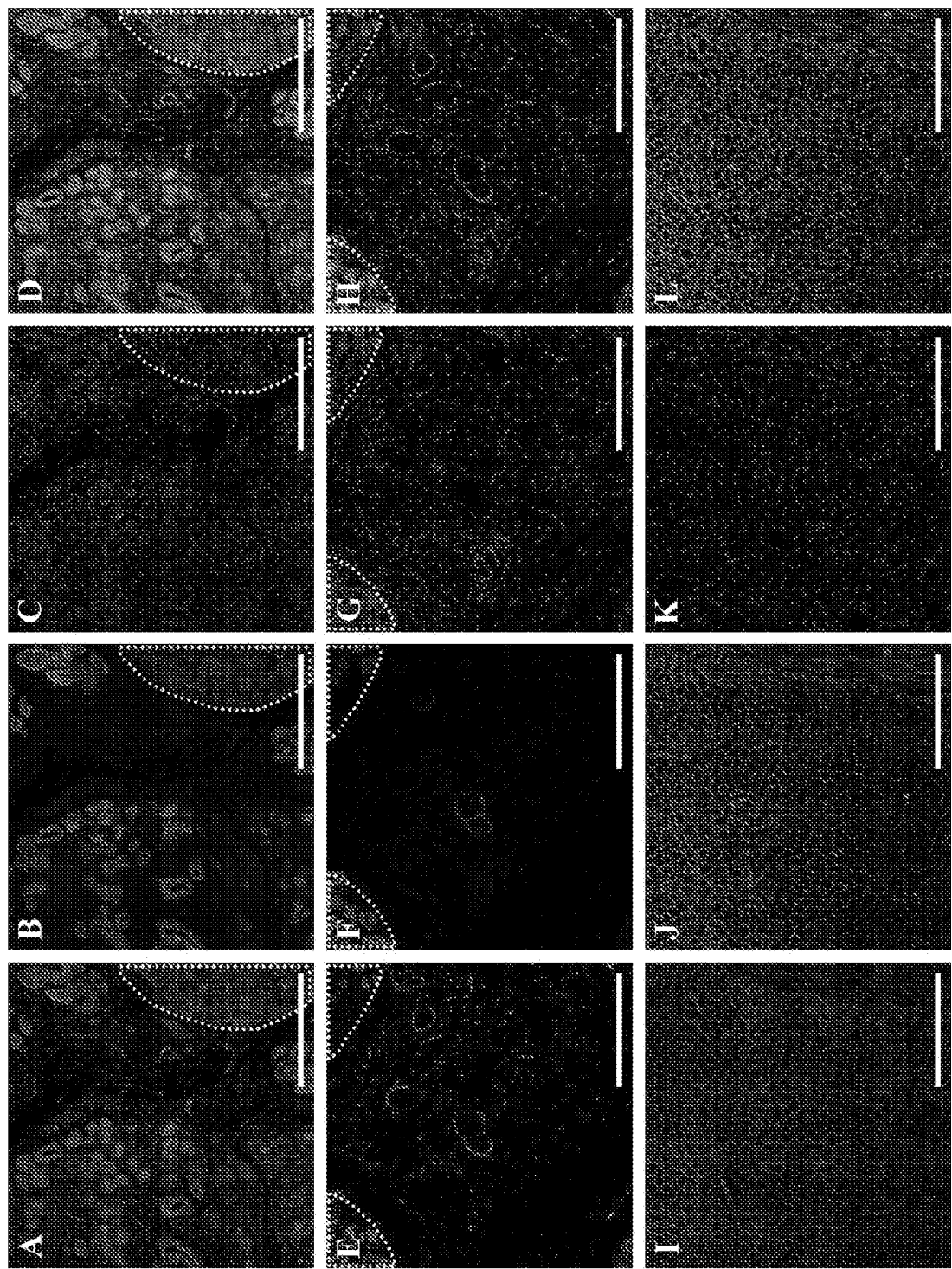

FIG. 17 is a series of images showing Zonula occludens-1 (green; panels A, E, I) and E-cadherin (red; panels B, F, J) organization, Nuclei stained with TO-PRO-3 iodide (blue; panels C, G, K) and composite images (multicolored; panels D, H, L) in wounded mSMG with $L_{1p}$-FH$^{680}$ (A-D), wounded mSMG without scaffold (E-H) and wounded mSMG with FH$^{680}$ (I-L) at post-surgery day 8. Yellow dotted areas are unwounded areas. Scale bars represent 200 μm. Representative image from a total of n=5 mice per group.

Figure 18:
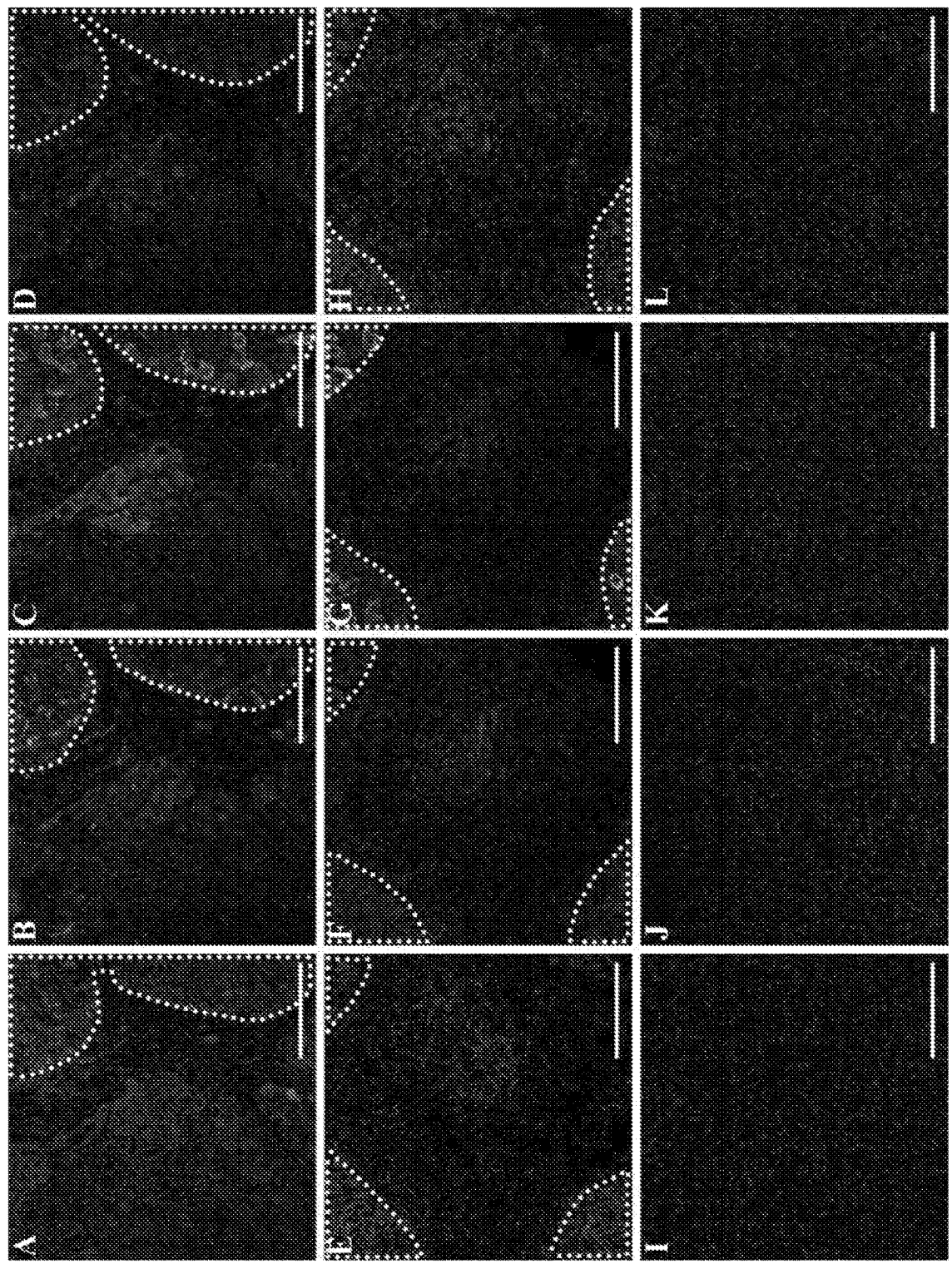

FIG. 18 is a series of images showing salivary functional marker organization in wounded mSMG with $L_{1p}$-FH$^{680}$ (panels A-D), wounded mSMG without scaffold (panels E-H) and wounded mSMG with FH$^{680}$ (panels I-L) determined using confocal microscopy as follows: rabbit anti-AQP5 (green; panels A, E, I), rabbit anti-TMEM16A (green; panels B, F, J), Rabbit Na$^+$/K$^+$-ATPase α antibody (green; panels C, G, K), anti-Von Willebrand factor (vWF, green; panels D, H, L), and TO-PRO-3 (blue; everywhere). Yellow dotted areas are unwounded areas. Scale bars represent 200 μm. Representative image from a total of n=5 mice per group.

FIGS. 19A-C are a series of images showing hematoxylin and eosin stained histological sections of wounded mSMG without hydrogel (FIG. 19A) with FH$^{680}$ (FIG. 19B) or with $L_{1p}$-FH$^{680}$ (FIG. 19C) at post-surgery day 20. Tiled images were generated using a Leica DMI6000B system.

Figure 20A:
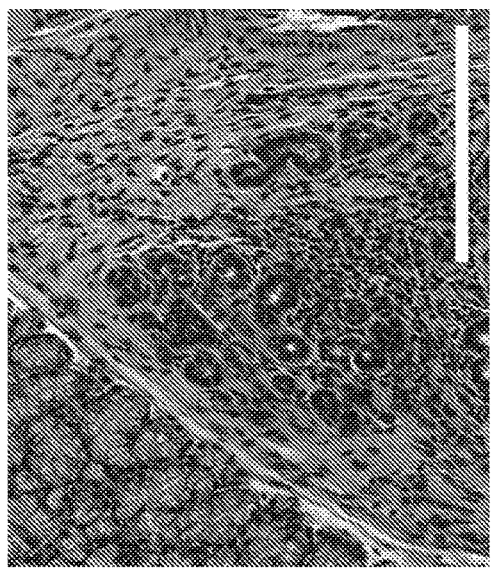
Figure 20B:
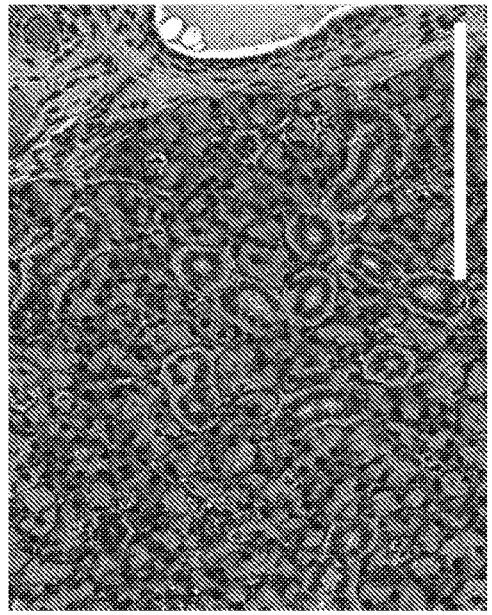
Figure 20C:
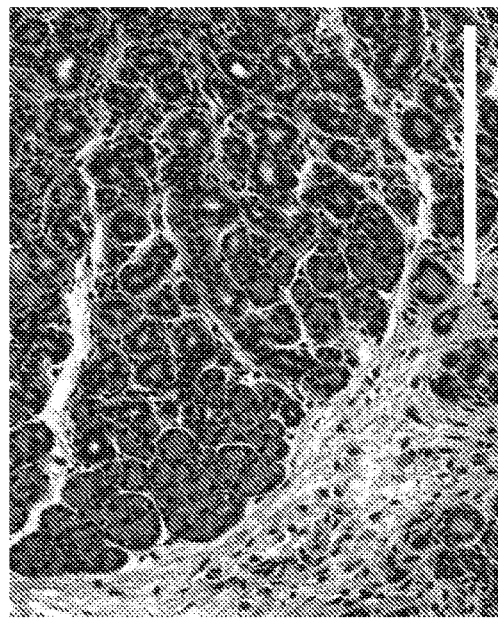

FIGS. 20A-C are a series of images showing hematoxylin and eosin stained histological sections of mSMG treated with and without FH scaffolds (magnification 20× from FIG. 19; yellow boxes). Shown are wounded mSMG without scaffold (FIG. 20A), wounded mSMG with FH$^{680}$ (FIG. 20B) and wounded mSMG with $L_{1p}$-FH$^{680}$ (FIG. 20C). Scale bars represent 200 μm.

Figure 21A:
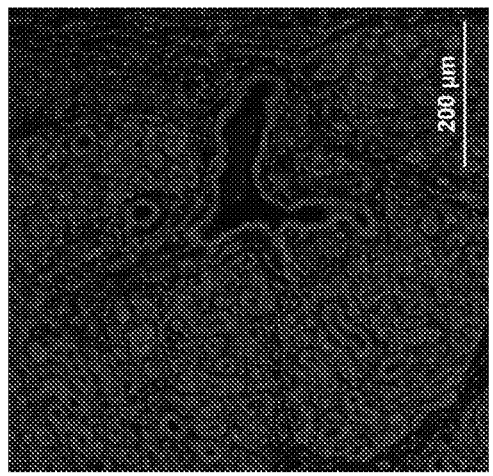
Figure 21B:
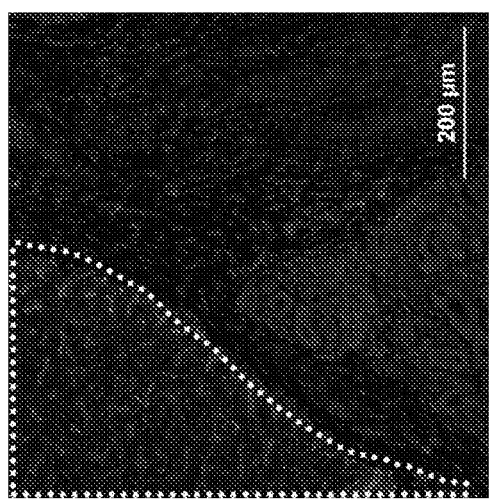
Figure 21C:
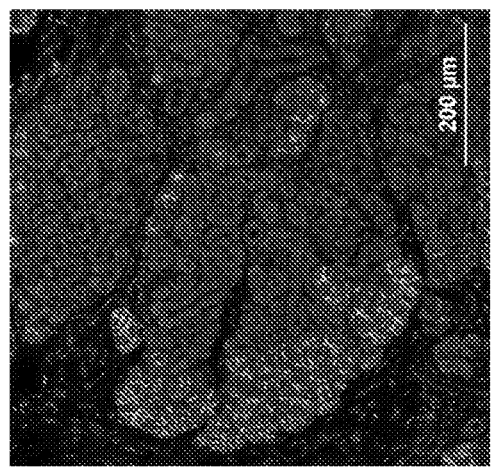

FIGS. 21A-C are a series of images showing AQP5 organization in wounded mSMG without scaffold (FIG.

21A), wounded mSMG with FH$^{680}$ (FIG. 21B) and wounded mSMG with $L_{1p}$-FH$^{680}$ (FIG. 21C) at post-surgery day 20. Yellow dotted areas are unwounded areas. Scale bars represent 200 μm.

Figure 22:
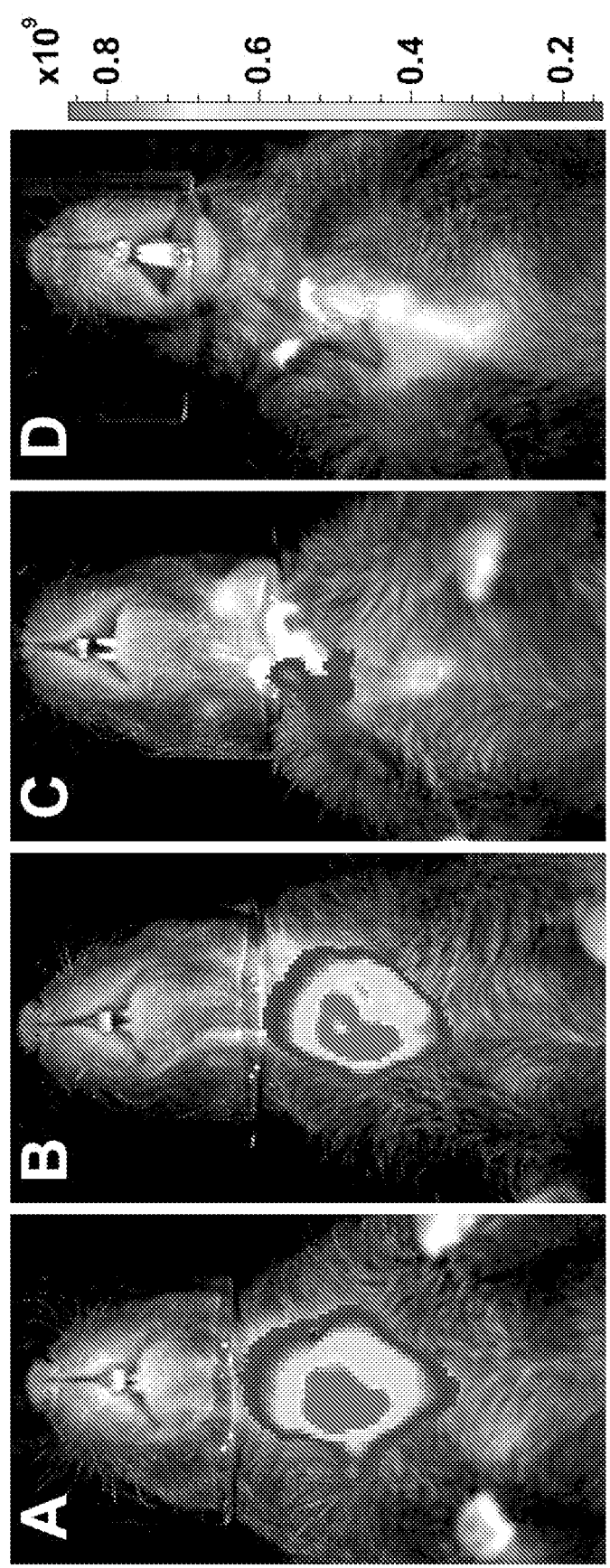

FIG. 22 is a series of images which illustrate that $L_{1p}$-FH successfully attach to mSMG and are degraded over time in vivo. The stability of $L_{1p}$-FH was monitored using a Xenogen IVIS 100 Bioluminescent Imager at day 1 (A), day 3 (B), day 8 (C), and day 20 (D). Radiant Efficiency: (p/sec/cm$^2$/sr)/(μW/cm$^2$).

Figure 23:
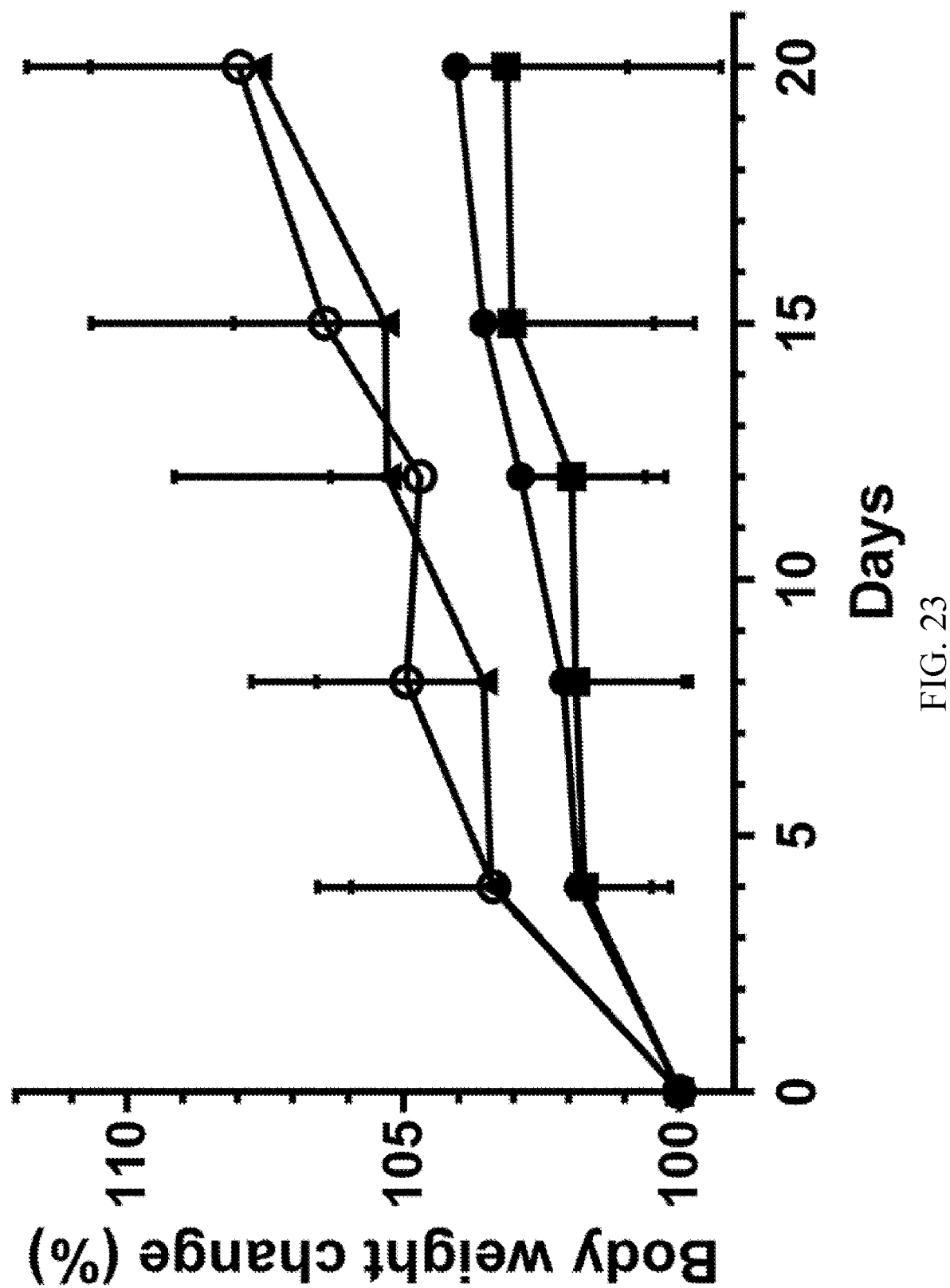

FIG. 23 is a graph illustrating changes in body weight (%) of FH alone (■) or $L_{1p}$-FH (▲) treated mice groups as compared to untreated mice group (●) and sham control group (○) over a 20-day period. Data represent the mean±SD of n=7 mice per condition, and statistical significance was assessed by two-way ANOVA (p<0.01) and Dunnett's post-hoc test for multiple comparisons to the untreated group.

Figure 24:
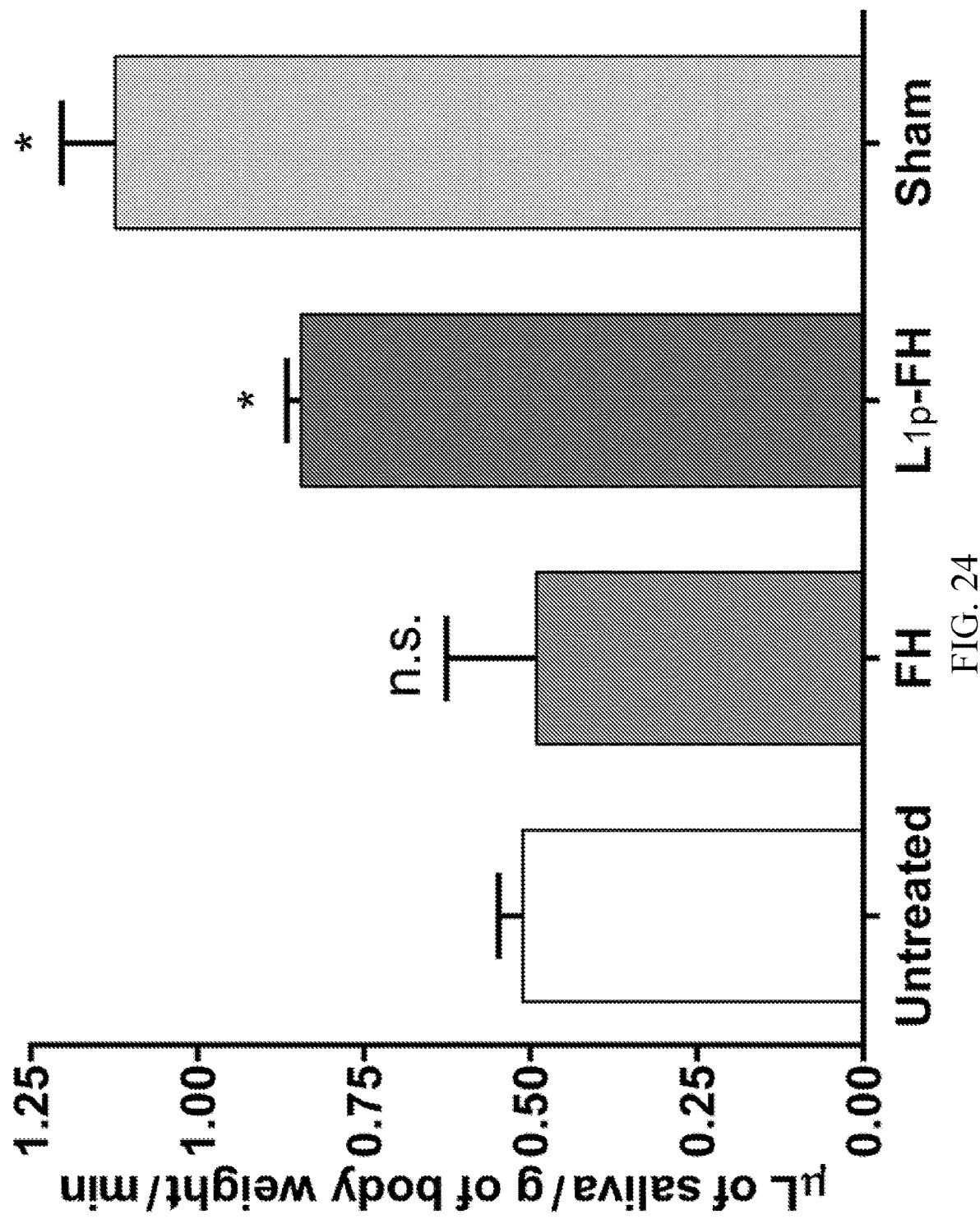

FIG. 24 is a graph illustrating that $L_{1p}$-FH applied to mSMG improved saliva secretion as compared to untreated and FH alone-treated mice. Mice were anesthetized and stimulated with pilocarpine at day 20 and saliva was collected for 5 minutes. Data represent the mean±SD of n=5 mice per condition, and statistical significance was assessed by one-way ANOVA (p<522 0.01) and Dunnett's post-hoc test for multiple comparisons to the untreated group.

Figure 25A:
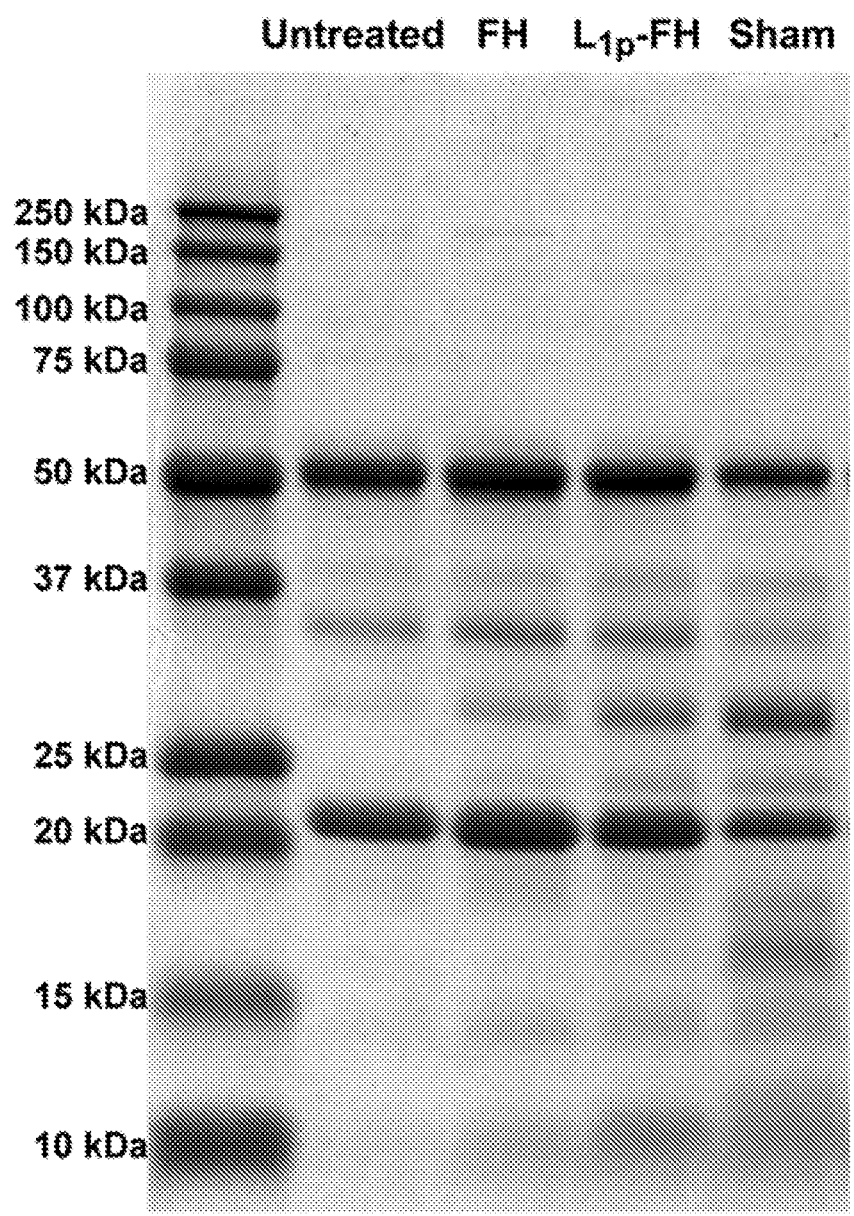
Figure 25B:
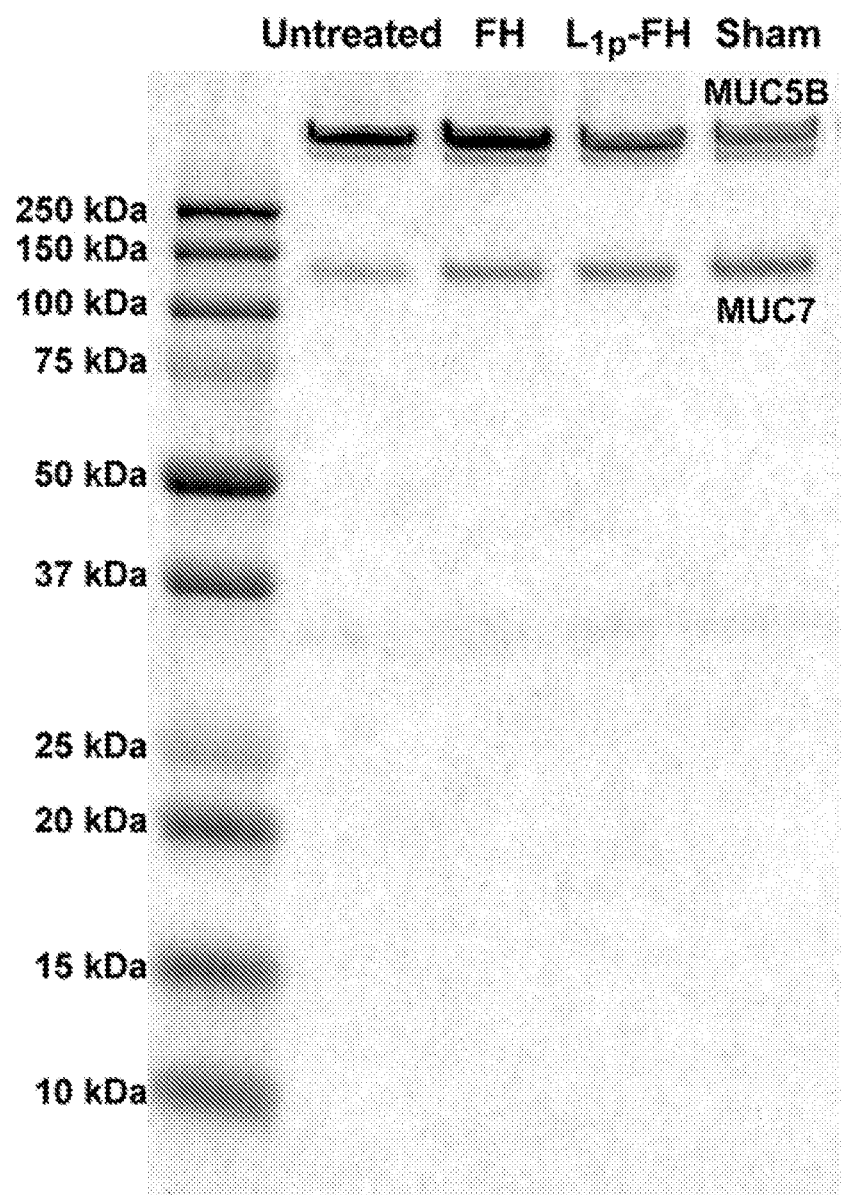
Figure 25C:
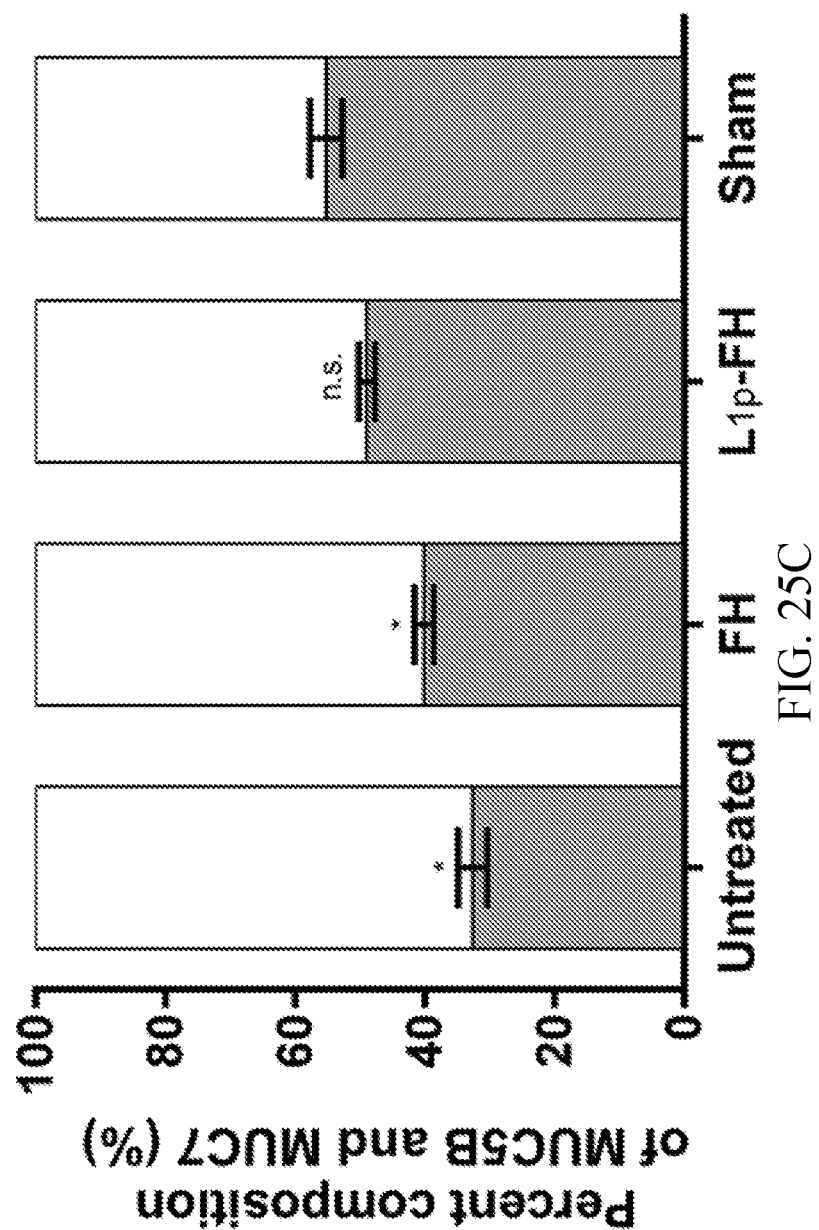

FIG. 25A and FIG. 25B are images of SDS-PAGE gels stained with Comassie Brilliant Blue R-250 (FIG. 25A) and 0.5% Alcian Blue 8GX (FIG. 25B) which illustrate that $L_{1p}$-FH applied to mSMG restored saliva composition. FIG. 25C is a graph illustrating the mucin composition of saliva from various treatment groups. The white bar indicates MUC5B and the gray bar indicates MUC7. Statistical significance was assessed by one-way ANOVA (p<0.01) and Dunnett's post-hoc test for multiple comparisons to the sham group.

Figure 26:
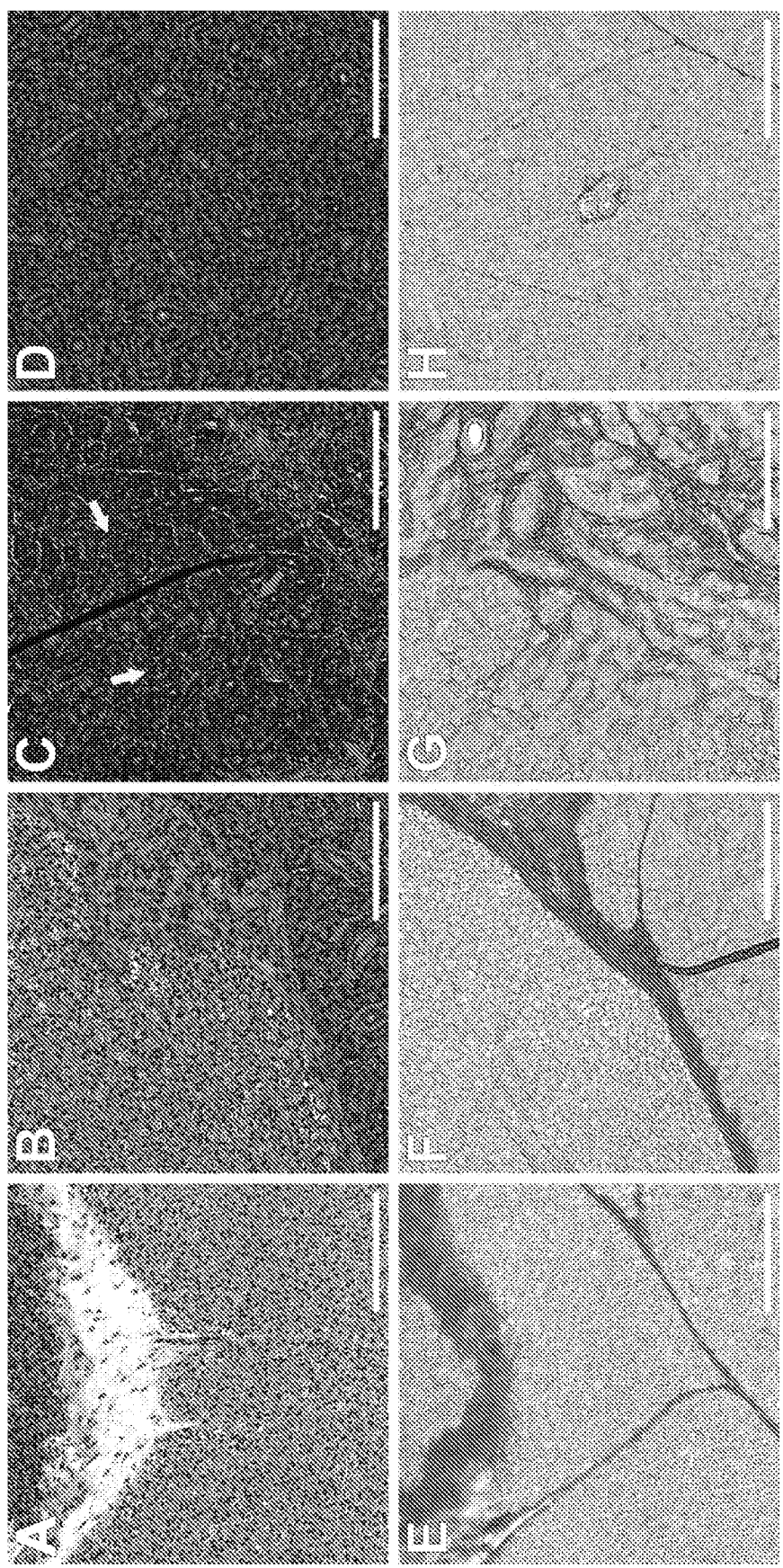

FIG. 26 is a series of images illustrating that surgical wounds treated with $L_{1p}$-FH displayed organized mSMG. Rehydrated sections were stained with hematoxylin-eosin (A-D) or picrosirius red (E-H) and analyzed using a Leica DMI6000B at 10× magnification. Shown are wounded mSMG without scaffold (A, E), wounded mSMG with FH alone (B, F), wounded mSMG with $L_{1p}$-FH (C, G), and sham control (D, H). Red arrows indicate structures and yellow arrows indicate ductal structures. Scale bars=200 μm.

Figure 27:
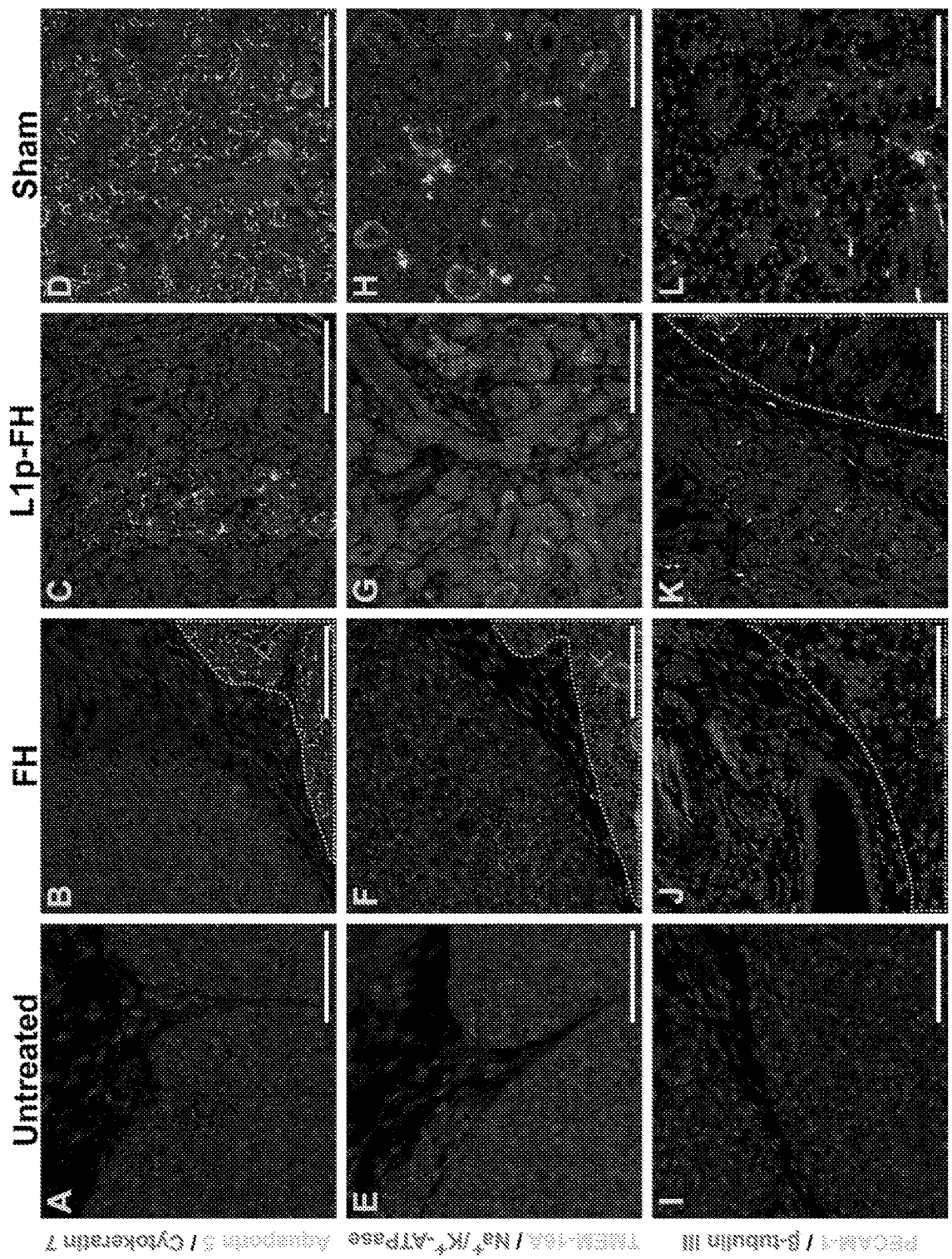

FIG. 27 is a series of images showing that acinar and ductal markers were expressed in the regenerating mSMG. Salivary structural and functional marker organization in wounded mSMG without scaffold (A, E, I), wounded mSMG with FH alone (B, F, J), wounded mSMG with $L_{1p}$-FH (C, G, K), and sham control (D, H, L) was determined using confocal microscopy as follows: rabbit anti-aquaporin 5 (A-D; green), mouse anti-cytokeratin 7 (A-D; red), rabbit anti-TMEM-16A (E-H; green), mouse anti-Na$^+$/K$^+$-ATPase (E-H; red), rabbit anti-PECAM-1 (I-L; green), and mouse anti-β-tubulin III (I-L; red). Yellow dotted lines indicate unwounded areas. Scale bars=100 μm.

DETAILED DESCRIPTION OF THE INVENTION

The disclosure provides compositions and methods for generating salivary tissue in an animal in need thereof. The compositions and methods can be used to repair damaged salivary tissue in the animal (e.g., a human).

In some embodiments, the disclosure provides a composition comprising a fibrin hydrogel conjugated to one or more peptides of laminin-111 (L1). The term "hydrogel," as used herein, refers to a three-dimensional network composed of hydrophilic polymers crosslinked either through covalent bonds or via physical intramolecular or intermolecular interactions. Hydrogels can absorb large amounts of water or biological fluids (up to several thousand percent), and swell readily without dissolving. The high hydrophilicity of hydrogels is primarily due to the presence of hydrophilic moieties such as carboxyl, amide, amino, and hydroxyl groups distributed along the backbone of polymeric chains. In the swollen state, hydrogels are soft and rubbery, closely resembling living tissues. Many hydrogels, such as chitosan and alginate-based hydrogels, exhibit desirable biocompatibility (see, e.g., El-Sherbiny, I. M., and Yacoub, M. H. *Global Cardiology Science & Practice*, 2013(3): 316-342 (2013); and Kyung et al., *J. Appl. Polym. Sci.*, 83: 128-136 (2002)). Since their discovery more than 50 years ago, hydrogels have been employed in a variety of applications including, for example, drug delivery, wound healing, ophthalmic materials, and tissue engineering (see, e.g., El-Serbiny and Yacoub, supra; Hoffman, A. S., *Ann. NY Acad. Sci.*, 944: 62-73 (2001); and Peppas et al., *Eur. J. Pharm. Biopharm.*, 50: 27-46 (2000)).

Hydrogels typically reach their equilibrium swelling when a balance occurs between osmotic driving forces, which encourage the entrance of water or biological fluids into the hydrophilic hydrogel matrix, and the cohesive forces exerted by the polymer strands within the hydrogel. These cohesive forces resist the hydrogel expansion and the extent of these forces depends particularly on the hydrogel crosslinking density. Generally, the more hydrophilic the polymer forming the hydrogel, the higher the total water amount absorbed by the hydrogel. Likewise, the higher the crosslinking extent of a particular hydrogel, the lower the extent of the gel swelling. Hydrogels in their dried forms are referred to in the art as "xerogels," while dry porous hydrogels resulting from the use of drying techniques (e.g., freeze-drying or solvent extraction) are referred to in the art as "aerogels" (see, e.g., Guenet, J. M., *Thermoreversible gelation of polymers and biopolymers*; Academic Press, New York (1992), p. 89).

Hydrogels can be classified based on a variety of characteristics, such as, for example origin, durability, response to stimuli, charge, structure, and composition. With respect to origin, hydrogels can be classified as natural, synthetic or semi-synthetic. Most synthetic hydrogels are synthesized by traditional polymerization of vinyl or vinyl-activated monomers. The equilibrium swelling values of these synthetic hydrogels vary widely according to the hydrophilicity of the monomers and the crosslinking density. Natural hydrogels typically are made of natural polymers including, for example, polynucleotides, polypeptides, and polysaccharides that can be obtained from a variety of sources (e.g., collagen from mammals and chitosan from shellfish exoskeletons). With respect to durability, hydrogels can be classified as durable (such as most polyacrylate-based hydrogels) or biodegradable (such as polysaccharide-based hydrogels), depending on their stability characteristics in a physiological environment. Biodegradable hydrogels have recently been developed in which degradable polymers inside the hydrogel matrices undergo chain scission to form oligomers of low molecular weight. The resulting oligomers are either eliminated by the organism or undergo further degradation. Such biodegradable hydrogels can be used in both biomedical and non-biomedical applications (see e.g., Zhu, W. and Ding, J., *J Appl Polym Sci.*, 99: 2375 (2006)). With respect to response to environmental stimuli, "smart" hydrogels have been developed that exhibit changes in swelling behavior, network structure, and/or mechanical characteristics in response to various environmental stimuli such as pH, temperature, light, ionic strength or electric field (see, e.g., Gutowska et al., *J Control Release*, 22: 95-104 (1992); Ferreira et al., *Int J Pharm.*, 194:169-180 (2000); and D' Emanuele, A. and Staniforth, J. N., *I. Pharm Res.*, 8: 913-918 (1991)). These changes typically disappear upon removal of the stimulus and the hydrogels are restored to their original state in a reversible manner.

Hydrogels can be used in a variety of tissue engineering applications, such as, for example, carriers for cell transplantations, scaffolds, barriers against restenosis, and drug depots. In one embodiment, the hydrogel can form a scaffold. The term "scaffold" refers to a structure that provides a platform for cell function, adhesion, and transplantation. Hydrogel scaffolds typically are used to provide bulk and mechanical structures to a tissue construct, whether cells are suspended within or adhered to a three-dimensional hydrogel framework. When a cellular-hydrogel adhesion is preferred over a suspension within the scaffold, inclusion of appropriate peptide moieties on the surface or throughout the bulk of the hydrogel scaffold can significantly improve cellular attachment. For instance, in one embodiment, an RGD (arginine-glycine-aspartic acid) adhesion peptide sequence can be incorporated into the hydrogel described herein to facilitate cellular attachment. Inclusion of RGD domains in hydrogels can improve cellular migration, proliferation, growth, and organization in tissue regeneration applications (see, e.g., Shin, H. and Mikos, A. G., *Biomaterials*, 24: 4353-4364 (2003) and Hersel et al., *Biomaterials*, 24: 4385-4415 (2003)). In addition, a variety of cells have been shown to favorably bind to the RGD-modified hydrogel scaffolds, including, for example, endothelial cells (ECs), fibroblasts, smooth muscle cells (SMCs), chondrocytes, and osteoblasts (see, e.g., Langer, R. and Tirrell, D. A., *Nature*, 428:487-492 (2004); and El-Serbiny and Yacoub, supra)

For tissue engineering, a hydrogel may be selected to meet a number of design criteria to effectively mimic the extracellular matrix (ECM) and thereby promote new tissue formation. Such design criteria may include, but are not limited to, the ability to provide a 3D architecture for cell growth, biodegradability, porosity, proper surface chemistry, biocompatibility, cell adhesion, and enhanced vascularization (see, e.g., El-Serbiny and Yacoub, supra). "Extracellular matrix (ECM)" is well known in the art as the non-cellular component present within all tissues and organs that provides structural support to cells and performs other important functions. ECM is composed of an interlocking meshwork of fibrous proteins, including collagen, elastin, fibronectin, and laminin as well as polysaccharide such as glycosaminoglycans (GAGs), which typically form proteoglycans upon covalent linkage to proteins (see, e.g., Alberts et al., *Molecular Biology of the Cell*, Garland Science, London (2007)).

As described herein, the hydrogel may be generated using any material suitable for tissue engineering applications, particularly salivary tissue engineering. For example, the hydrogel described herein may be generated using natural polymers, such as polynucleotides, polypeptides, and polysaccharides. Such natural polymers may be obtained or derived from any natural source, including, for example, a living organism (a mammal, a fish, an insect, or a plant). For example, chitosan is a natural polymer obtained from shellfish exoskeletons, while collagen is a natural polymer obtained from mammals. Other natural polymers that may be used in hydrogels include, but are not limited to, hyaluronic acid (HA), an amphiphilic peptide, alginate, collagen, fibrin, gelatin, chondroitin sulfate, carboxymethylcellulose, dextran, agarose carbomer, and derivatives thereof. It will be appreciated that hydrogels based on natural polymers are particularly suited for tissue engineering applications due to their intrinsic characteristics of biological recognition (e.g., presentation of receptor-binding ligands and susceptibility to cell-triggered proteolytic remodeling and degradation).

In some embodiments, the hydrogels of the present disclosure may be generated using a synthetic polymer. Examples of suitable synthetic polymers include, but are not limited to, poly(ethylene glycol) (PEG), poly(ethylene glycol) diacrylate (PEGDA), poly(lactic acid) (PLA), poly (ethylene oxide) (PEO), poly(vinyl alcohol) (PVA), poly (hydroxyl-ethyl methacrylate) (PHEMA), methacrylated dextran-graft-lysine (Dex-MA-LA), methacrylamide-modified gelatin (Gel-MA), and derivatives thereof. Hydrogels based on synthetic polymers may exhibit less immunogenicity then natural polymer-based hydrogels, and may provide greater control over material characteristics and tissue responses.

Some hydrogels described herein may be generated using self-assembled peptides (SAPs), which are polypeptides that undergo self-assembly under specific conditions (e.g., a hydrophilic environment) to form fibers or other nanostructures (see, e.g., El-Serbiny and Yacoub, supra, Adams et al., *Langmuir*, 23: 12729-12736 (2007); Guler, M. O. and Stupp, S. I., *J Am. Chem. Soc.*, 129: 12082-12083 (2007); and Williams et al., *Angew Chem Int Ed.*, 46: 3051-3054 (2007)). SAPs typically are amphiphilic molecules which may comprise a polypeptide linked to a long chain alkyl tail and functionalized with an RGD cell adhesion ligand (RGD) (described above). A variety of amphiphilic SAPs-based hydrogels have been used in tissue engineering applications (see, e.g., Adams et al., supra, Hartgerink et al., *Science*, 294: 1684-1688 (2001); and Hwang et al., *Proc. Natl. Acad. Sci. USA*, 99: 9662-9667 (2002)). SAPs-based hydrogels also can be used to incorporate bioactive molecules and allow for their controlled release. SAPs-based hydrogels can be chemically conjugated to different moieties (e.g., fibronectin or laminin peptide domains) to allow signaling to cell surface receptors and to enhance cellular adhesion (see, e.g., Hwang et al., supra).

The hydrogel described herein may comprise fibrin (referred to as a "fibrin hydrogel" or "FH"). Fibrin is a fibrous, non-globular protein involved in blood clotting that is formed by thrombin-mediated cleavage of fibrinogen. Polymerized fibrin combines with platelets to form a hemostatic plug or clot over wound site. Fibrin hydrogels are water-swollen, cross-linked polymeric structures that form scaffolds and allow for 3D cell assembly. Fibrin forms a hydrogel at physiological temperatures and contains native arginine-glycine-aspartic acid (RGD) sites that promote cell attachment (see, e.g., Janmey et al., *J. R. Soc. Interface*, 6: 1-10 (2009)). In addition, several studies demonstrate engineering of FH with conjugated growth factors, genes, or recombinant viruses for multiple applications ranging from wound healing, vascular tissue engineering, and lentiviral arrays. For example fibrin hydrogels have been used to deliver keratinocyte growth factor (KGF) to promote wound healing (see, e.g., Geer et al., *Am. J. Pathol.*, 167: 1575-1586 (2005)), a peptide-TGF-$\beta$1 fusion protein to improve the contractile function, extracellular matrix synthesis and mechanical properties of vascular grafts (see, e.g., Liang, M. S. and Andreadis, S. T., *Biomaterials*, 32: 8684-8693 (2011); and Liang et al., *Biomaterials*, 34: 7281-7291 (2003), and plasmid DNA and recombinant lentivirus for engineering gene delivery microarray platforms (see, e.g., Yao et al., *Tissue Eng.*, 11 (7-8): 991-1003 (2005)); Yao et al., *Pharm Res*, 25 (5): 1212-21 (2008); and Slaughter et al., *Adv Mater,* 21 (32-33): 3307-29 (2009)). In addition, fibrin hydrogels can support cell viability and differentiation for long periods of time by interaction of cells with fibrin (possibly through integrin $\alpha_v\beta_3$), which may suppress capsize activation and reactive oxygen species generation. In addition to drug delivery as described above, fibrin hydrogels are used in a variety of other bioengineering applications, such as, for example, as a hemostatic glue for wound repair, cell delivery, cell differentiation and tissue engineering, and patterning. The structural and functional features of fibrin hydrogels are further characterized in, e.g., Janmey et al., *J R. Soc. Interface*, 6: 1-10 (2009)).

Fibrin hydrogels described herein can be prepared using any suitable method known in the art. Such methods may include, for example, emulsification, lyophilization, emulsification-lyophilization, solvent casting-leaching, gas foaming-leaching, photolithography, electrospinning, microfluidics, micromolding, and 3D-organ/tissue printing (see, e.g., El-Serbiny and Yacoub, supra).

The present disclosure provides compositions comprising a fibrin hydrogel conjugated to one or more peptides of laminin-111 (also referred to as "L1"). Laminins are biologically active extracellular matrix (ECM) proteins composed of heterotrimers formed by one heavy chain ($\alpha$) and two light chains ($\beta$ and $\gamma$) that combine to form fourteen unique isoforms (see, e.g., Aumailley M., *Cell Adhesion & Migration*, 7(1): 48-55 (2013)). Laminins can self-assemble, bind to other matrix macromolecules, and have unique and shared cell interactions mediated by integrins, dystroglycan, and other receptors. Through these interactions, laminins contribute to cell differentiation, cell shape and movement, maintenance of tissue phenotypes, and promotion of tissue survival (see, e.g., Colognato, H. and Yurchenco, P. D., *Dev. Dyn.*, 218: 213-234 (2000); and Beck et al., *The FASEB Journal*, 4(2): 148-160 (1990)).

Laminin-111 ($\alpha$1, $\beta$1, $\gamma$1; LM-111), which is also referred to in the art as "laminin-1" or "L1," is the predominant laminin isoform expressed during embryonic development and plays an important role in myoblast proliferation, mobility, and myofiber formation (see, e.g., Goudenege et al., *Mol. Ther.*, 18: 2188-2163 (2010); and Silva-Barbosa et al., *Transplantation*, 85: 566-575 (2008)). Laminin-111 consists of three chains, $\alpha$1 (400 kDa), $\beta$1 (210 kDa) and $\gamma$1 (200 kDa), that associate to form a cruciform structure. Laminin-111 binds to the other abundant basement membrane components, which include collagen IV, perlecan, entactin/nidogen, as well as laminin-111 itself. Such interactions are specific and important in the assembly of the basement membrane matrix. Laminin-111 also interacts with cells and has multiple biological activities, including promoting cell adhesion, migration, neurite outgrowth and tumor growth and metastasis. Proteolytic fragments as well as synthetic peptides have been used to localize and study these activities, indicating that L1 is a multifunctional protein with the potential for many active sites (Kikkawa et al., *Cell Adhesion & Migration*, 7(1): 150-159 (2013)).

In mouse models of muscular dystrophy, L1 has been shown to effectively inhibit muscle damage and enhance muscle regeneration via increased satellite cell expansion and new fiber synthesis (see, e.g., Goudenege et al., supra; Rooney et al., *Proc. Natl. Acad. Sci. USA*, 106: 7991-7996 (2009); Rooney et al., *Am. J. Pathol.*, 174: 256-264 (2009);

Rooney et al., *Am. J. Pathol.*, 180: 1593-1602 (2012); and Van Ry et al., *Hum. Mol. Genet.*, 23: 383-396 (2014). Laminin-111 also has been shown to play a critical role in salivary cell cluster formation and organization. The full L1 polypeptide sequence, however, may not be suitable for clinical applications, as some L1 protein domains are known to promote tumorigenesis or immunogenic responses that may outweigh the potential benefits provided by the whole protein (see, e.g., Topley et al., R. J. *Cancer*, 67: 953-958 (1993); and Beliveau et al., *J. Genes. Dev.*, 24: 2800-2811 (2010)). The use of synthetic L1 peptides may be a less expensive and less immunogenic alternative to full-length L1 protein (see, e.g., Bellis, S. L., *Biomaterials*, 32: 4205-4210 (2011). Thus, in one embodiment, the composition described herein comprises one or more peptides of L1 conjugated to the fibrin hydrogel. The term "peptide," as used herein, refers to a compound comprising two or more amino acids linked via a peptide bond. A "peptide bond" is well-known in the art as a covalent bond between two amino acids formed when the amino group of one amino acid is bonded to the carboxyl group of the other amino acid.

Any suitable L1 peptide that can be conjugated to a fibrin hydrogel and promote salivary tissue formation or organization may be used in the composition described herein. Examples of L1 peptides include, for example, IKVAV (SEQ ID NO: 6), AG73, YIGSR (SEQ ID NO: 7), CI 6, and A99. The composition described herein may comprise one or more L1 peptides conjugated to the fibrin hydrogel, such as two or more (e.g., 2, 3, 4, 5, or more) L1 peptides conjugated to the fibrin hydrogel. In some embodiments, the fibrin hydrogel has the following structure:

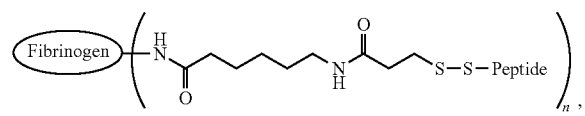

wherein n is 2 to 6 (i.e., 2, 3, 4, 5, or 6). In some embodiments, the composition may comprise two L1 peptides conjugated to the fibrin hydrogel, with one L1 peptide comprising the amino acid sequence of CGGALRGDN-amide (SEQ ID NO: 1) (referred to as the "A99" or "RGD" peptide of L1) and the other L1 peptide comprising the amino acid sequence of CGGADPGYIGSRGAA-amide (SEQ ID NO: 2) (referred to as the "YIGSR" peptide of L1). The YIGSR L1 peptide corresponds to the β1 chain from L1 and has been shown to exhibit tumor-growth inhibiting and antiproliferative effects (see, Yoshida et al., *Br. J. Cancer*, 80: 1898-1904 (1999); Frith et al., *J. Stem Cells Dev.*, 21: 2442-2456 (2012); and Hosokawa et al., *Dev. Growth Differ.*, 41: 207-216 (1999)). The A99 (RGD) peptide corresponds to the al chain from L1 and has been shown to improve cell attachment and proliferation of mouse fibroblasts on RGD-modified films (see, e.g., Wohlrab et al., *Biomaterials*, 33: 6650-6559 (2012); Frith et al., supra; and Yamada et al., *Biomaterials*, 34: 6539-6547 (2013)). The one or more L1 peptides can be synthetically generated using suitable methods known in the art, such as those described in, e.g., Nam et al., *Biomacromolecules*, 17: 2293-2301 (2016), Sambrook et al., *Molecular Cloning: A Laboratory Manual*, 4th ed., Cold Spring Harbor Press, Cold Spring Harbor, N.Y. (2012); and Ausubel et al., *Current Protocols in Molecular Biology*, John Wiley & Sons, N.Y. (2016).

In some embodiments, the one or more L1 peptides may be conjugated to the fibrin hydrogel via a linker molecule. For example, the one or more L1 peptides may be linked to the fibrin hydrogel with a linker molecule comprising a disulfide bond. The linker molecule may be cleavable and may comprise a reactive chemical group that can react with the fibrin hydrogel and a reactive chemical group that can react with the one or more L1 peptides, such as, for example, N-succinimidyl esters and N-sulfosuccinimidyl esters. Examples of cleavable linker molecules that can be used to make the composition described herein may include, but are not limited to, sulfosuccinimidyl 6-(3'-(2-pyridyldithio)propionamido)hexanoate, N-succinimidyl 3-(2-pyridyldithio) propionate (SPDP) (see, e.g., Carlsson et al., *Biochem. J.*, 173, 723-737 (1978)), N-succinimidyl 4-(2-pyridyldithio) butanoate (SPDB) (see, e.g., U.S. Pat. No. 4,563,304), and N-succinimidyl 4-(2-pyridyldithio)pentanoate (SPP) (see, e.g., CAS Registry number 341498-08-6). Preferably, the cleavable linker is sulfosuccinimidyl 6-(3'-(2-pyridyldithio) propionamido)hexanoate (Sulfo-LC-SPDP).

While cleavable linkers may be used in the composition described herein, a non-cleavable linker also may be used. A non-cleavable linker may comprise any chemical moiety that is capable of linking the one or more L1 peptides to a fibrin hydrogel in a stable, covalent manner. Thus, non-cleavable linkers may be substantially resistant to acid-induced cleavage, light-induced cleavage, peptidase-induced cleavage, esterase-induced cleavage, and disulfide bond cleavage, at conditions under which the one or more L1 peptides remain active. Many suitable crosslinking reagents that form non-cleavable linkers between biomolecules are well known in the art and include, for example, linkers having an N-succinimidyl ester or N-sulfosuccinimidyl ester moiety, or linkers having a maleimido- or halo-acetyl-based moiety. Crosslinking reagents comprising a maleimido-based moiety include, for example, N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propanoate (SBAP).

To monitor hydrogel stability in vitro and in vivo, the fibrin hydrogel may also comprise a detectable label. The terms "label" and "detectable label," as used herein, refer to a moiety attached, directly or indirectly, to the fibrin hydrogel or one or more L1 peptides to render the fibrin hydrogel or the conjugation between the one or more L1 peptides and hydrogel detectable, and the fibrin hydrogel or L1 peptide so labeled is referred to as "detectably-labeled." A label may be selected so as to produce a signal that is detectable (e.g., by visual or instrumental means). In this aspect, the label may be any signal-generating moiety that produces a measurable signal which is detectable by external means (e.g., by the measurement of electromagnetic radiation or fluorescence). The detectable label may be any signal-producing substance known in the art, including, for example, an enzyme (e.g., horseradish peroxidase, alkaline phosphatase, alkaline peroxidase, glucose 6-phosphate dehydrogenase, and the like), a chromophore or chromogen (e.g., dyes that absorb light in the ultraviolet or visible region), a phosphor, a fluorescer, a fluorophor (e.g., fluorescent proteins such as green fluorescent protein, yellow fluorescent protein, red fluorescent protein, cyan fluorescent protein); a fluorescent label (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, quantum dots (e.g., zinc sulfide-capped cadmium selenide), a thermometric label, an immuno-polymerase chain reaction label; a phycobilin (e.g., phycoerythrin, R-Phycoerythrin, B-Phycoerythrin); biotin/avidin; a Xanthene derivative (e.g., fluorescein, rhodamine, Oregon green, eosin, Texas red); a cyanine derivative (e.g., cyanine, Cy dyes, indocarbocyanine, oxacarbocyanine, thiacarbocyanine, merocyanine); a naphthalene derivative (e.g., dansyl and prodan derivatives); a coumarin derivative; a oxadiazole derivative e.g., (pyridyloxazole, nitrobenzoxadiazole, benzoxadiazole); a Pyrene derivative (e.g., cascade blue); an oxazine derivative (e.g., Nile red, Nile blue, cresyl violet, oxazine 170); an acridine derivative (e.g., proflavin, acridine orange, acridine yellow); an arylmethine derivative (e.g., auramine, crystal violet, malachite green); a tetrapyrrole derivative (e.g., porphin, phtalocyanine, bilirubin)); a luminophore; a chemiluminescent compound (e.g., acridinium esters, thioesters, or sulfonamides; luminol, isoluminol, phenanthridinium esters, and the like); a radioactive compound (e.g., such as $^3H$, $^{125}I$, $^{35}S$, $^{14}C$, $^{32}P$, and $^{33}P$), and the like. In one embodiment, the fibrin hydrogel comprises a fluorescent label. A "fluorophore" or "fluorescent label" refers to compounds with a fluorescent emission maximum between about 350 and 900 nm.

The present disclosure also provides methods of generating salivary tissue in an animal in need thereof, comprising administering a composition comprising a fibrin hydrogel conjugated to one or more peptides of laminin-111 (L1) to an animal in need thereof, whereby salivary cells are generated in the animal. The present disclosure also provides methods of repairing damaged salivary tissue, comprising applying a composition comprising a fibrin hydrogel conjugated to one or more peptides of laminin-111 (L1) to damaged salivary tissue, whereby new salivary cells are generated and the damaged salivary tissue is repaired. Descriptions of the composition, fibrin hydrogel, peptides of laminin-111 and conjugation thereof to the fibrin hydrogel, and components thereof, set forth above in connection with the composition also are applicable to the aforementioned method of generating salivary tissue in an animal.

In accordance with the above methods, damaged salivary tissue may be in vitro (e.g., in a cell culture system) or in vivo (e.g., within an organism). Any suitable animal can be the source of the damaged salivary tissue. Examples of suitable animals include, but are not limited to, a bird (for example, a duck or a goose), a fish (e.g., a shark), an insect, or a mammal. Preferably, the animal is a mammal, such as a non-primate mammal (e.g., a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.). More preferably, the animal is a human or a mouse.

The damaged salivary tissue may be the result of a disease or disorder that affects salivary tissues. Such diseases and disorders may include, but are not limited to, benign tumors (e.g., pleomorphic adenomas and Warthin's tumor), cancerous tumors, genetic diseases (e.g., ectodermal dysplasia), sialolithiasis (a calcified mass or sialolith forms within a salivary gland, usually in the duct of the submandibular gland), sialadenitis (infection of the salivary gland), Sjögren's syndrome, ectodermal dysplasia, viral infections (e.g., flu, mumps, Coxsackie virus, echovirus, and cytomegalovirus), and salivary gland cysts. In some embodiments, the damaged salivary tissue may be the result of γ-irradiation therapies (e.g., for head and neck cancers). In addition, or alternatively, the animal may also suffer from hyposalivation (i.e., reduced saliva production or saliva flow).

The damaged salivary tissues may be obtained from, or located in, any salivary gland. Most animals have three major pairs of salivary glands: parotid glands, submaxillary (mandibular) glands, and sublingual glands. The methods described herein may generate salivary tissue in any salivary gland of an animal. The parotid glands are the largest of the salivary glands, which secrete saliva to facilitate mastication and swallowing and amylase to begin starch digestion. The submandibular glands are located beneath the lower jaws and produce a secretion comprised of both serous fluid and mucus. Sublingual glands are located inferior to the tongue and anterior to the submandibular glands and produce secretion that is primarily mucus in nature. Thus, the damaged salivary tissue can be parotid gland tissue, submandibular gland tissue, and/or sublingual gland tissue.

For in vivo applications, any route of administration may be used to deliver the composition to the animal. Indeed, although more than one route may be used to administer the composition, a particular route may provide a more immediate and more effective reaction than another route. In some cases, the compositions disclosed herein may be applied or instilled into body cavities via surgical procedures. The compositions also may be administered orally, topically, or via intramuscular injection. For example, the composition may be administered on a device that is suitable for tissue engineering applications. In other embodiments, the composition may be administered via retroductal delivery using cannulation of the main salivary excretory ducts (which are clearly visible in the oral cavity).

Damaged salivary tissue is "repaired" if new salivary tissue is generated in place of, or in addition to, the damaged salivary tissue. In some embodiments, the repair of damaged salivary tissue may affect the treatment of a disease or disorder that impacts salivary tissues, such as those described herein. As used herein, the terms "treatment," "treating," and the like refer to obtaining a desired pharmacologic and/or physiologic effect. Preferably, the effect is therapeutic (i.e., the effect partially or completely cures a disease and/or adverse symptom attributable to the disease). To this end, the inventive method comprises administering a "therapeutically effective amount" of the composition. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the composition to elicit a desired response in the individual.

The following examples further illustrate the invention but, of course, should not be construed as in any way limiting its scope.

Example 1

This example describes the production of a fibrin hydrogel comprising two peptides of laminin-111 (L1) conjugated thereto.

Two biologically active peptides derived from L1 were synthesized on an ABI431 or ABI433 peptide synthesizer using a standard Fmoc solid-phase peptide synthesis as follows: amino acids were protected at their amino terminus by the Fmoc (9-fluorenylmethoxycarbonyl) group and coupled to the growing chain after activation of the carboxylic acid terminus. The Fmoc group was then removed by piperidine treatment and the process was repeated. After the peptide was assembled, it was removed from the resin by treatment with trifluoroacetic acid (TFA). At the same time, protecting groups on amino acid side chains were removed yielding the crude linear peptide. Finally, one-step purification by reverse-phase HPLC yielded peptides with >95% purity. Two scrambled peptides were synthesized as controls using the same method as described above. All peptides were synthesized with a cysteine and two glycine residues (Cys-Gly-Gly, CGG) at the N-terminus. A cysteine free thiol group was used for coupling with thiol reactive fibrinogen and the two glycine residues were used as a spacer. A list of these peptides is shown in Table 1.

TABLE 1

| Peptide | Sequence | Molecular Mass | L1 Sequence |
| --- | --- | --- | --- |
| A99 (RGD) | CGGALRGDN-amide (SEQ ID NO: 1) | 860.9 | laminin α1 chain (1145-1150) |
| YIGSR | CGGADPGYIGSRGAA-amide (SEQ ID NO: 2) | 1350.5 | laminin β1 chain (925-936) |
| RAD | CGGALRADN-amide (SEQ ID NO: 3) | 875.0 | scrambled peptide for A99 |
| SGIYR | CGGADPGSGIYRGAA-amide (SEQ ID NO: 4) | 1350.5 | scrambled peptide for YIGSR |

Lyophilized fibrinogen was dissolved in 0.1 M phosphate-buffered saline (PBS, pH 7.2, 0.15 M NaCl, 1 mM EDTA) and dialyzed using a disposable cellulose membrane (MWCO=3.5 kDa) overnight. The fibrinogen solution was then purified using a 0.8 μm filter. In order to produce a thiolreactive fibrinogen, 7.2 equivalent of Sulfo-LC-SPDP was added to the purified fibrinogen solution and incubated for 1 hour at room temperature. The cross-linker is able to react with both the side chain of lysine (ε-amino group) and the α-amine at the N-terminus. However, the coupling efficiency of the α-amine and the ε-amine is highly dependent on pH. At a neutral pH, ε-amino of lysine is rapidly protonated. Therefore, coupling of the cross-linker through the α-amine of N-terminus is more efficient than the ε-amino of lysine (see, e.g., Kinstler et al., *Adv. Drug Delivery Rev.*, 54: 477-85 (2002); and Gauthier, M. A. and Klok, H.-A. *Chem. Commun.*, 2591-2611 (2008)).

Subsequently, the excess Sulfo-LC-SPDP and its hydrolysis products (N-hydroxysulfosuccinimide, Sulfo-NHS) were removed by dialysis. The level of LC-SPDP-modification was determined by measuring the absorbance of pyridine-2-thione at 343 nm. Briefly, 10 μL of DTT (15 mg/mL) was added to 1 mL of modified fibrinogen. After 15 minutes of incubation, absorbance at 343 nm was measured, and the change in absorbance was calculated using the following equation: $\Delta A343 = (A343$ after DTT$) - (A343$ before DTT$)$. The reaction was monitored by thin layer chromatography (TLC) and Ultraviolet-visible (UV) spectroscopy. The level of SPDP modification was calculated using the following equation:

$$\text{moles of SPDP per mole of fibrinogen} = \frac{\Delta A_{343}}{8080} \times \frac{341 kDa}{\frac{mg}{mL} \text{of fibrinogen}}$$

where 341 kDa reflects the molecular weight of fibrinogen, and the value 8080 reflects the extinction coefficient for pyridine-2-thione at 343 nm: $8.08 \times 10^3$ M$^{-1}$ cm$^{-1}$ (see, e.g., Stuchbury et al., *Biochem. J.*, 151: 417-32 (1975); and Carlsson et al., *Biochem. J.*, 173: 723-37 (1978)).

Figure 1A:
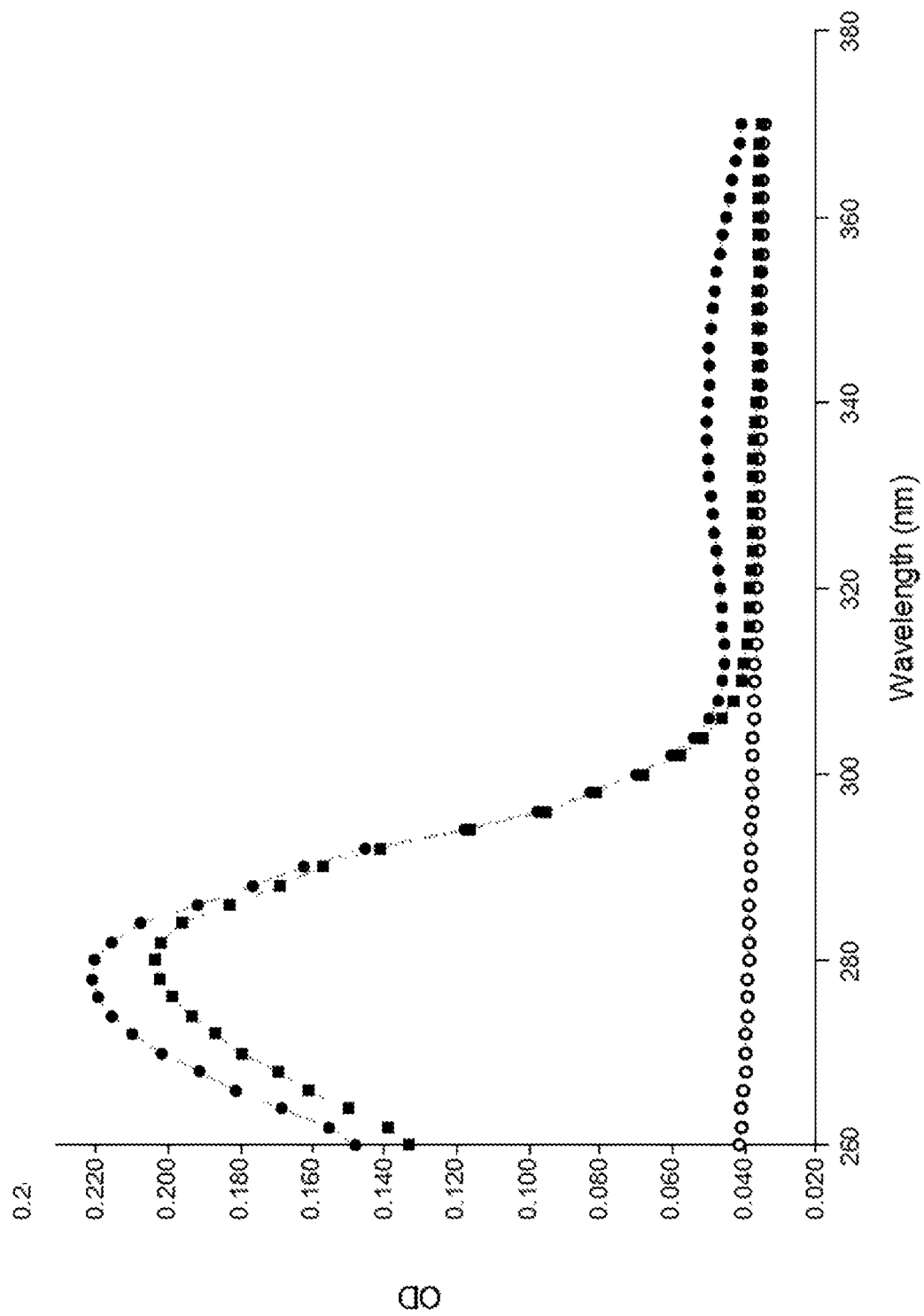
FIG. 1A is a graph illustrating the UV-Vis absorption spectra of LC-SPDP activated fibrinogen after incubation in the presence (●) or absence (■) of DTT for 15 minutes, where (○) represents the blank signal.
Figure 1B:
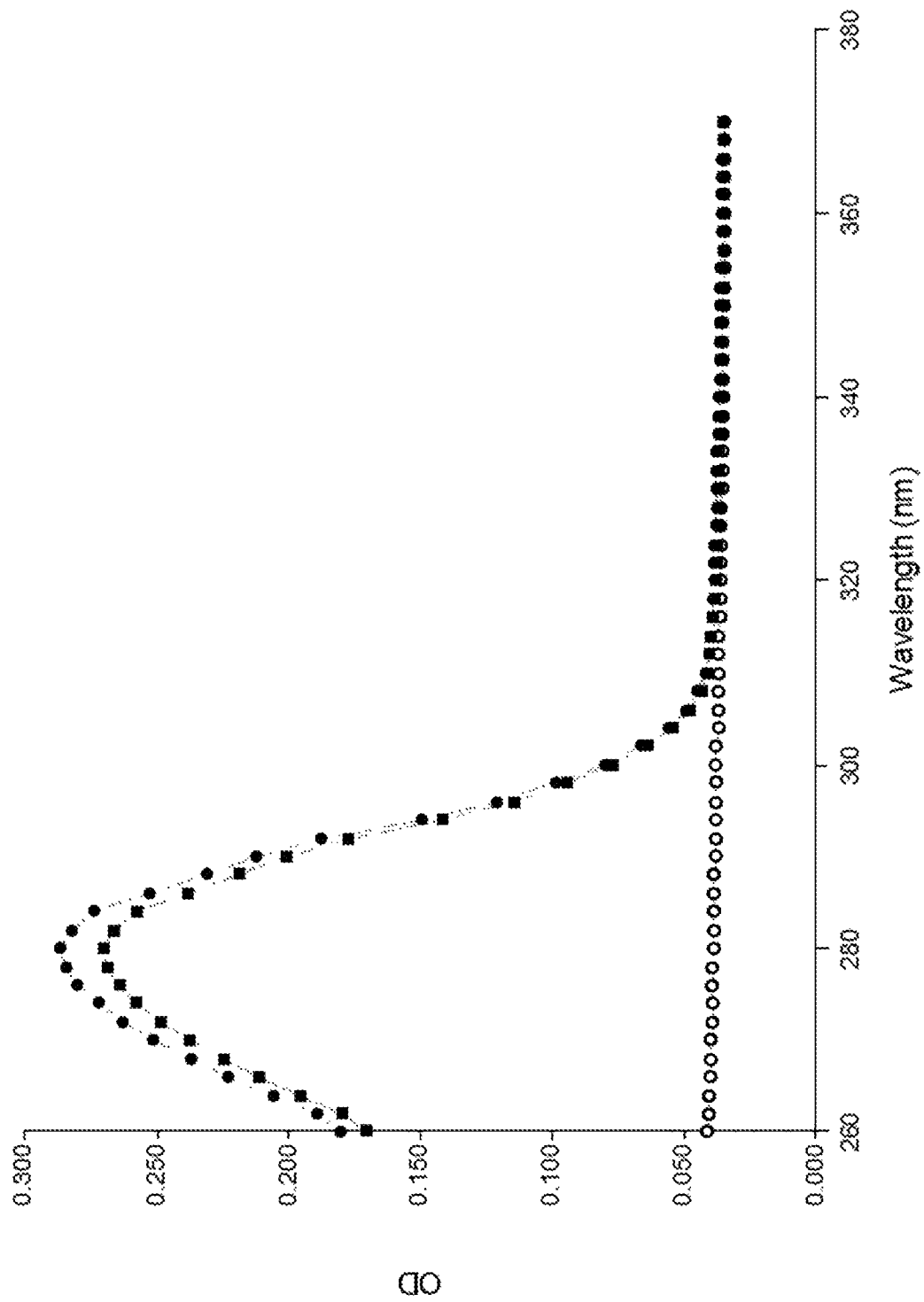
FIG. 1B is a graph illustrating the UV-Vis absorption spectra of YIGSR-conjugated fibrinogen after incubation in the presence (●) or absence (■) of DTT for 15 minutes, where (○) represents the blank signal.

Based on the result of the UV measurements (see FIGS. 1A and 1B), six cross-linkers were conjugated to fibrinogen. For peptide conjugation, LC-SPDP activated fibrinogen was dissolved in 50 mM PBS (pH 7.2, 0.15 M NaCl, 10 mM EDTA). Two equivalents of peptide per 2-pyridyldithiol groups of LC-SPDP fibrinogen were added to the solution, and the mixture was reacted for 18 hours at room temperature. The reaction was monitored by thin-layer chromatography (TLC). Finally, the product was dialyzed against ultrapure water using a dialysis membrane (MWCO=3.5 kDa) as described above and products were filtered using a 0.22 μm syringe filter from Merck Millipore. The percent yields for the products were 79.47% (A99), 90.04% (YIGSR), 83.17% (RAD), and 80.05% (SGIYR), respectively. Peptide-conjugated fibrinogen was lyophilized and stored at −80° C. until further use.

The concentration of fibrinogen was calculated using the following equation:

$$\text{Fibrinogen (mg/mL)} = \frac{A_{280} \times \text{Dilution Factor}}{\varepsilon_{Fib}}$$

where $\varepsilon_{Fib}$, the extinction coefficient at 280 nm for human fibrinogen, is 1.51 mLmg$^{-1}$ cm$^{-1}$ (Marder et al., *J. Biol. Chem.*, 244, 2111-9 (1969)).

Figure 2:
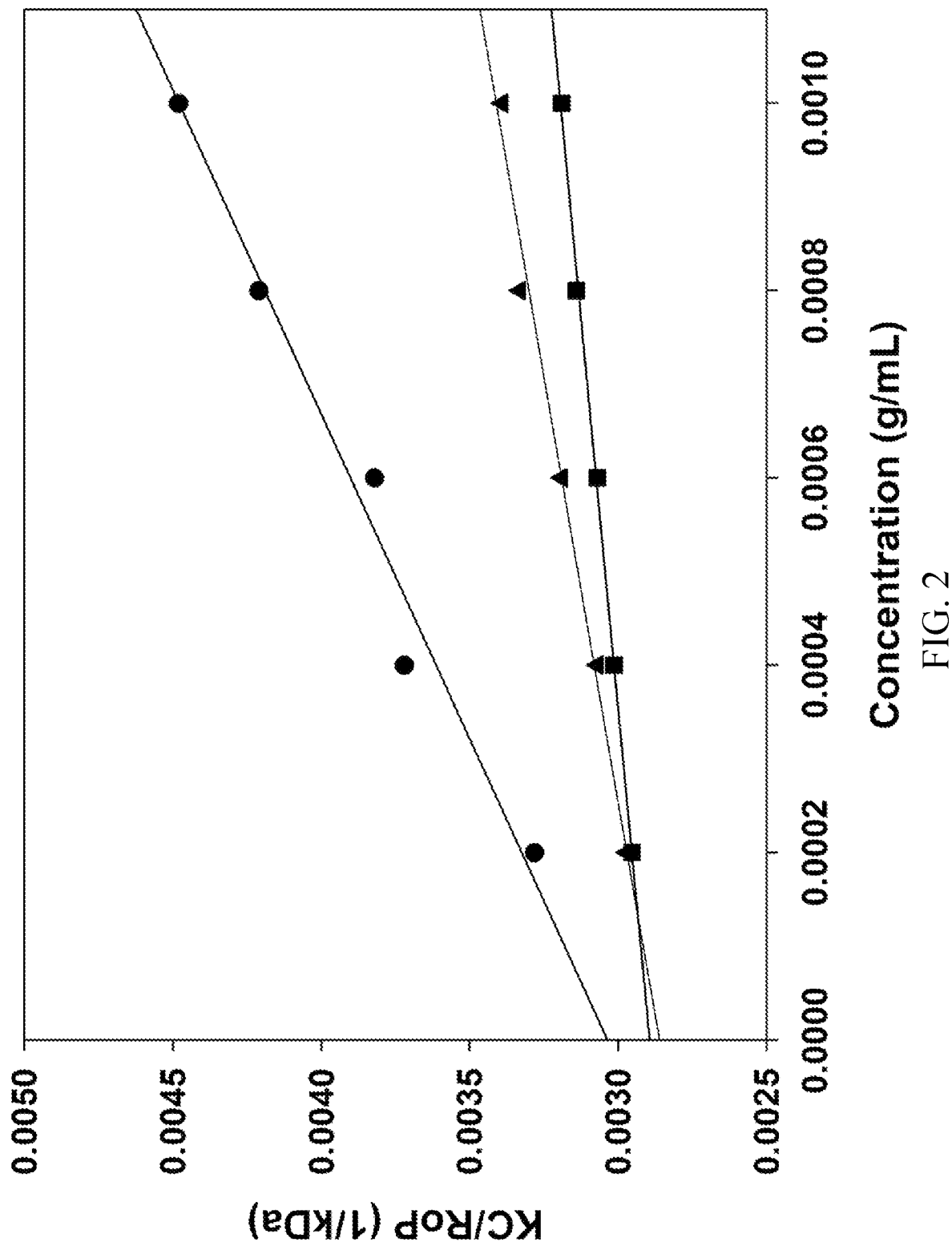
FIG. 2 is a graph illustrating Debye plots for fibrinogen (●), YIGSR-conjugated fibrinogen (▲) and A99-conjugated fibrinogen (■).

Peptide conjugation was confirmed using and UV-vis spectrum data (see FIGS. 1A and 1B) and static light scattering data (see FIG. 2). The molecular weight of L1 derived peptide-conjugated fibrinogens was slightly increased. The molecular weight was calculated using the Rayleigh equation, which describes the relationship between molecular weight and scattered light:

$$\text{Rayleigh Equation:} \frac{KC}{R_\theta} = \left(\frac{1}{M} + 2A_2 C\right)$$

where K is an optical constant, C is the sample concentration, θ is the measurement angle, $R_\theta$ is the Rayleigh ratio, M is the molecular weight, and $A_2$ is the second virial coefficient. Based on the UV-vis spectrum data it was estimated that six peptides were conjugated to a single fibrinogen molecule, as shown in Table 2.

TABLE 2

Molecular Weights of the Unmodified and Modified Fibrinogen (kDa) results are expressed as mean ± SD (n = 3)

| | |
|---|---|
| fibrinogen | 330 ± 7.87 |
| YIGSR-conjugated fibrinogen | 350 ± 3.70 |
| A99-conjugated fibrinogen | 347 ± 2.98 |
| SGIYR-conjugated fibrinogen | 349 ± 4.78 |
| RAD-conjugated fibrinogen | 345 ± 5.12 |

Cross-linked fibrin hydrogel (FH) was generated by mixing plasma-derived bovine thrombin (2.5 U/mL) and fibrinogen (2.5 mg/mL) in Tris-buffered saline (TBS) with $CaCl_2$ (2.5 mM) and εACA (2 mg/mL) as previously described (Raut et al., Controlled Release, 144, 213-20 (2010)). One hundred microliters of mixture per well in eight-well chambers was allowed to solidify in the incubator at 37° C. overnight. The overall preparation scheme of YIGSR-(50%) and A99-(50%) conjugated FH was the same as described in Example 1. YIGSR-conjugated fibrinogen (1.25 mg/mL) and A99-conjugated fibrinogen (1.25 mg/mL) were used as monomers.

FH has both elastic and viscous properties, and these properties are highly sensitive to changes in polymerization (see, e.g., Janmey et al., Soc. Interface, 6: 1-10 (2009); and Weisel, J. W., Biophys. Chem., 112: 267-76 (2004)). In addition, the rheological parameters can provide information about the structural changes (see, e.g., Wedgwood et al., Macromol. Symp., 334: 117-25 (2013). Therefore, the peptide conjugated FHs were characterized using rheological techniques. Specifically, rheological measurements of fibrin hydrogel were performed on a stress-controlled rheometer (TA Instruments, AR 2000ex). All tests were performed using the cone plate geometry (4°/20 mm) with a truncation height of 114 μm at 37° C. Human fibrinogen (2.5 mg/mL) and thrombin (2.5 U/mL) solutions were rapidly mixed in TBS buffer (2.5 mM $CaCl_2$, 2 mg/mL εACA) and then applied to the bottom of the rheometer plate. To prevent evaporation, the shear gap was covered with a solvent trap cover. The modulus of elasticity (G') and the strain (%) were recorded 5 minutes after FH addition. Data were analyzed by two-way ANOVA with pairwise comparisons where p<0.05 represents significant differences between experimental groups.

The procedure used to synthesize peptide-conjugated fibrinogen and the fibrin hydrogel is illustrated in FIGS. 3A and 3B, respectively. As shown in FIG. 4, the elasticity of YIGSR-conjugated FH and A99-conjugated FH was slightly less than unmodified FH, and RAD-conjugated FH was slightly greater than unmodified FH. These results were significantly different from the control (FH alone), except for SGIYR-conjugated FH.

The results of this example confirm the production of a fibrin hydrogel comprising two L1 peptides conjugated thereto, and that peptide conjugation affects the overall physical structure of the FH.

Example 2

This example describes a method of generating three-dimensional salivary cell clusters in vitro using L1-peptide-conjugated hydrogels.

The polarized rat parotid cell line (Par-C10) was derived from freshly isolated rat parotid gland acinar cells by transformation with simian virus 40 and exhibits morphological, biochemical, and functional characteristics of freshly isolated acinar cells (see, e.g., Quissell et al., Eur. J. Morphol, 36: 50-54 (1998); Turner et al., Am. J. Physiol., 275: C367-74 (1998)). Par-C10 cells ($5 \times 10^5$ at passages 40-60) were grown to confluence in DMEM/F12 (1:1) containing 2.5% (v/v) FBS and the following supplements: 0.1 μM retinoic acid, 80 ng/mL EGF, 2 nM triiodothyronine, 5 mM glutamine, 0.4 μg/mL hydrocortisone, 5 μg/mL insulin, 5 μg/mL transferrin, 5 ng/mL sodium selenite, and 50 μg/mL gentamicin. Two thousand cells were plated on top of different hydrogels as a two-dimensional (2D) culture and incubated at 37° C. in a humidified atmosphere of 95% air and 5% $CO_2$.

After three days in culture (shown to be optimal for sphere formation in, e.g., McCall et al., supra; and Odusanwo et al., Am. J. Physiol Cell Physiol, 302, C1331-45 (2012)), cells were fixed in 2% PFA for 20 minutes at room temperature and stained for 10 minutes using 200 μL of PBS containing 0.1% Triton X-100 with 30 μM DAPI. After washing three times with PBS, cell morphology was observed under an inverted microscope (Leica DMI6000B, Germany) at 10× magnification. The DAPI stained cells in three randomly selected fields were then counted using ImageJ software (see, e.g., Burgess et al., Proc. Natl. Acad. Sci. U.S.A., 107: 12564-9 (2010); and Turner et al., J. Am. Dent. Assoc., 138, S15-S20 (2007). All experiments were performed in triplicate and repeated three times. All data are presented as means±SD. Statistical analysis was performed using Graph-Pad Prism software. Data were analyzed by one-way ANOVA followed by pairwise post hoc Tukey's t-test where p<0.05 represented significant differences between experimental groups.

As shown in FIG. 5, Par-C10 cells formed fibroblast-like monolayers when grown on unmodified FH (panel A of FIG. 5). In addition, Par-C10 cells displayed fibroblast-like monolayers when grown on scrambled peptide-conjugated FH, such as SGIYR-conjugated FH (panel B of FIG. 5) and RAD-conjugated FH (panel C of FIG. 5). These results suggest that both unmodified FH and scrambled peptide-conjugated FH are not suitable for formation of Par-C10 salivary cell clusters. However, Par-C10 cells grown on YIGSR and/or A99 peptide-conjugated FH formed round organized structures, with an average cell cluster diameter of approximately 70 μm when grown on a combination of YIGSR-(50%) and A99-(50%) conjugated FH (panel F of FIG. 5). Moreover, a combination of the peptides (YIGSR 50% with A99 50%) showed an increase in cell attachment (537.78±62.61 cells/mm$^2$) and Par-C10 cell cluster formation (18.00±5.29 clusters/mm$^2$) as compared to the unmodified FH (444.78±61.65 cells/mm$^2$, 2.56±1.01 clusters/mm$^2$) (FIGS. 6A and 6B).

Carbachol (Cch) is a cholinergic agonist that stimulates the M3 muscarinic acetylcholine receptor in salivary glands, leading to increased intracellular free calcium concentration ($[Ca^{2+}]_i$) (see, e.g., Foskett, J. K. and Melvin, J. E., Science, 244: 1582-5 (1989)). Therefore, the intracellular free calcium levels of Par-C10 salivary cell clusters on FH were determined using a Leica DMI6000B imaging system. After three days of incubation, cells were treated with 4 μM Fura-2-acetoxymethylester (Fura-2 AM) for 20 minutes at 37° C. in cell culture medium (as described above) and washed with cell culture medium. The cells were stimulated with 100 μM carbachol (Cch). Images were then recorded and analyzed using Leica Application Suite X software. To determine statistical significance, the fluorescence intensity was measured by a Tecan Infinite M200 Pro spectrophotometer (Tecan Group Ltd., Männedorf, Switzerland) at room temperature. Dual excitation measurements at 340 and 380 nm were performed, and the emission intensity was recorded at 510 nm. All experiments were performed in sextuplicate. Data were analyzed by one-way ANOVA followed by pairwise post hoc Tukey's t-test where p<0.01 represented significant differences between experimental groups.

Cch (100 μM) induced an increase in $[Ca^{2+}]_i$ in Par-C10 cells cultured under all the conditions studied (i.e., FH, SGIYR, RAD, YIGSR, A99 alone and in combination, FIG. 7A-F), consistent with results from previous studies using rat parotid gland and Par-C10 cells (see, e.g., McCall et al., supra; and Maruyama et al., *J. Dent. Res.*, 94: 1610-7 (2015)). However, Par-C10 cells cultured on YIGSR-modified FH (FIG. 7B,G) displayed a significantly higher increase of $[Ca^{2+}]_i$ as compared to unmodified FH (FIG. 7A,G) and A99-modified FH (FIG. 7C,G). Furthermore, increases of $[Ca^{2+}]_i$ in Par-C10 cells on FH containing both YIGSR and A99 peptides (FIG. 7D,G) was significantly different from the $[Ca^{2+}]_i$ response observed on FH modified with YIGSR alone, which was notable as increases in $[Ca^{2+}]_i$ are critical for eliciting the physiological secretory function in salivary glands.

The structure of Par-C10 cells was further analyzed by immunofluorescence. Specifically, after three days of incubation, Par-C10 cells were fixed in 2% PFA for 10 minutes, incubated with 0.1% Triton X-100 in PBS for 10 minutes and washed three times with PBS for five minutes at room temperature. For ZO-1 staining, Par-C10 cells were blocked for 2 hours in 5% goat serum at room temperature and incubated with a rabbit anti-ZO-1 antibody (1:50) in 5% goat serum overnight at 4° C. The following day, cells were warmed to room temperature for 20 minutes and washed three times for five minutes with PBS. Cells were incubated for 1 hour with Alexa Fluor 488-conjugated goat anti-rabbit secondary antibody (1:500) in 5% goat serum then washed three times with PBS. For the immunofluorescent staining of F-actin, cells were stained with Alexa Fluor 568-conjugated phalloidin (1:400, PBS) for 1 hour at room temperature and washed three times for five minutes with PBS. For nuclear staining, cells were incubated with TO-PRO-3 iodide (1:1,000, PBS) for 15 minutes at room temperature and washed three times for five minutes with PBS. Cells were visualized using a Carl Zeiss 700 LSM confocal microscope. The average lumen diameter was calculated using the ZEN software (Carl Zeiss, Thornwood, N.Y.). Apical ZO-1 stained cells in randomly selected fields were counted as a cluster. However, cell aggregates were counted as beehive-like pattern structures lacking apical ZO-1. All data were presented as means±SD (n=9). Statistical analysis was performed using GraphPad Prism software. Data were analyzed by one-way ANOVA followed by pairwise post hoc Tukey's t-test where p<0.05 represents significant differences between experimental groups. Microscope settings were kept consistent for all samples.

Par-C10 cells formed monolayers when cultured on unmodified FH, as shown in FIG. 8A, FH-conjugated with L1 peptide AG73-CGGRKRLQVQLSIRT-amide (FIG. 8E; SEQ ID NO: 5), and scrambled peptide-conjugated FH, as shown in FIG. 9. On the other hand, Par-C10 cells grown on A99-modified FH formed salivary cell clusters, but with no lumens, as shown in (FIG. 8C). Notably, cells grown in the presence of YIGSR peptide (i.e., YIGSR-modified FH or YIGSR combined with A99-modified FH) were able to form lumens, as indicated by the intense F-actin and ZO-1 staining on the apical region, as shown in (FIG. 8B,D). As shown in FIG. 8, a combination of YIGSR-(50%) and A99-(50%) conjugated FH exhibited a higher level of ZO-1 polarization and a well-defined lumen structure (16.48±3.95 μm) as compared to unmodified FH (form monolayers) and A99-conjugated FH (2.64±1.60 μm).

The results of this example confirm that the L1 peptide-modified fibrin hydrogel described herein can generate salivary tissue in vitro.

Example 3

This example describes a method of promoting salivary tissue regeneration in wounded mouse submandibular glands in vitro.

The A99 and YISGR L1 peptides and L1 peptide-conjugated fibrinogen were synthesized as described in Example 1. To monitor hydrogel in vivo, DyLight 680 conjugated fibrinogen was also prepared. Briefly, lyophilized fibrinogen (51.28 mg) was dissolved in 0.05M sodium borate buffer at pH 8.5 (10 mg/mL) and DyLight 680 was dissolved in DMF (10 mg/mL). One hundred microliter of DyLight 680 solution was added to fibrinogen solution and incubated for 1 hour at room temperature. Non-reacted reagent was removed from fibrinogen solution by dialysis (MWCO=3.5 kDa). The concentration of dye labeled fibrinogen was calculated using the following equation:

$$\text{Dye labeled } fibrinogen \text{ (mg/mL)} = \frac{A_{280} - (A_{684} \times 0.128)}{\varepsilon_{Fib}} \times \text{Dilution Factor} \quad (1)$$

where $\varepsilon_{Fib}$, the extinction coefficient at 280 nm for human fibrinogen, is 1.51 mL mg$^{-1}$ cm$^{-1}$.

The degree of labeling was calculated using the following equation:

$$\text{Moles dye per mole protein} = \frac{A_{684} \text{ of the labeled protein} \times \text{Dilution Factor}}{\varepsilon_{Fluor} \times \text{protein concentration}(M)} \quad (2)$$

where $\varepsilon_{Fluor}$, the extinction coefficient at 684 nm for DyLight 680 Dye, is 140,000 (M$^{-1}$ cm$^{-1}$). Based on these results, five dyes were conjugated to fibrinogen. The dye-conjugated fibrinogen was freeze-dried and stored at −80° C. until further use.

For in vitro experiments, fibrin hydrogel (FH) was fabricated by dissolving fibrinogen (2.5 mg/mL) and plasma-derived bovine thrombin (2.5 U/mL) in Tris-buffered saline (TBS) with $CaCl_2$ (2.5 mM) and εACA (2 mg/mL). For $L_{1p}$-FH, YIGSR-conjugated fibrinogen (1.25 mg/mL) and A99-conjugated fibrinogen (1.25 mg/mL) were used as monomers instead of fibrinogen (2.5 mg/mL). One hundred microliter of hydrogel mixture per well in eight-well chambers was then allowed to solidify at 37° C. in a humidified incubator.

The components of fibrin hydrogels for in vitro and in vivo studies (discussed below) are set forth in Table 3.

TABLE 3

|  | Used Volume | Hydrogel | Composition (nmole) | | | |
|---|---|---|---|---|---|---|
|  |  |  | Fibrinogen | DyLight 680 | YIGSR | A99 |
| In vitro | 100 µL | FH | 733.1 | — | — | — |
|  | 100 µL | $L_{1p}$-FH | 716.7 | — | 2141.0 | 2159.1 |
| In vivo | 40 µL | $FH^{680}$ | 292.5 | 289.7 | — | — |
|  | 40 µL | $L_{1p}$-$FH^{680}$ | 287.3 | 289.7 | 685.1 | 690.9 |

To prepare mouse submandibular gland cell clusters, female C57BL/6 mice at 5-7 weeks of age were anesthetized via IP injection with 80-100 mg/kg ketamine and 5 mg/kg xylazine. Mice were euthanized by abdominal exsanguination and submandibular glands were removed, processed and plated as described below. All animal usage, anesthesia, and surgery were conducted with the approval of the University of Utah Institutional Animal Care and Use Committee, in accordance with their strict guidelines.

Freshly dispersed cell clusters from C57BL/6 mouse submandibular glands (mSMGs) were prepared as follows: mSMGs were minced and then placed in a 35 mL GentleMACS C Tube (Miltenyi Biotec, Auburn, Calif.) containing dispersion medium (6.5% (v/v) tumor dissociation enzyme mix (Miltentyi Biotec) in Dulbecco's Modified Eagle's Medium (DMEM)). Following the manufacturer's instructions, the tissue was enzymatically and mechanically digested using alternating steps of dissociation with the GentleMACS Dissociator (Miltenyi Biotec) and 20 minutes incubation at 37° C. in a shaking water bath. After three dissociation steps and two incubations, the cells were centrifuged at 150×g for five minutes at 37° C., and the dispersion medium was removed. Cells were then resuspended in 10 mL complete medium (i.e., DMEM/Ham's F-12 (1:1) containing 2.5% (v/v) fetal bovine serum (FBS; Life Technologies, Carlsbad, Calif.) along with the following supplements: 2 nM triiodothyronine, 0.1 µM retinoic acid, 0.4 µg/ml hydrocortisone, 80 ng/ml epidermal growth factor (EGF), 5 ng/ml sodium selenite, 5 mM glutamine, 5 µg/ml insulin, 5 µg/ml transferrin) and passed through 100 µM, 70 µM and 40 µM cell strainers. Cells were then washed via centrifugation at 150×g for five minutes at 37° C. and resuspended once more in complete medium (described above). Cells were counted using a hemocytometer and plated as described below.

To plate mSMG cell clusters on FH or $L_{1p}$-FH, one hundred microliters of FH or $L_{1p}$-FH were pipetted into wells of 8-well chambered coverglass slides and allowed to set for 24 hours at 37° C. Then, freshly dissociated mSMG cell clusters were plated at a density of approximately 20-30,000 cell clusters per well and allowed to attach for 24 hours. The following day, cells were washed once to remove dead and suspended cells, and then medium (described above) was replaced every other day prior to fixation, bright field, and confocal analysis.

After six days of growth, the mSMG cell clusters were counted via bright field imaging. Clusters were counted prior to fixation so as to capture any clusters that might wash away during fixing procedures. Using an EVOS XL Core (Life Technologies) microscope, two images were captured per well (top left and bottom right) using a 4× objective. Round sphere-like cell clusters were counted and divided by the area imaged to determine the number of cell clusters/$mm^2$ (FIG. 10). Only round clusters possessing clearly delineated smooth dark edges were counted, so as to exclude non-sphere-like clusters or clumps.

mSMG cell clusters were grown on $L_{1p}$-FH or FH for 6 days (Table 3). Cells grown on $L_{1p}$-FH formed round salivary cell clusters, as shown in (FIG. 10A). In contrast, cells grown on FH formed fewer cell clusters, as shown in (FIG. 10B). $L_{1p}$-FH appeared to promote cell clustering over FH, as shown in FIGS. 10A, 10B, and 10E. To demonstrate formation of salivary lumens, mSMG cell clusters were stained with phalloidin and TO-PRO-3 as described above. These results indicate that mSMG are able to form salivary cell clusters with an apical F-actin ring (FIG. 10C) suggesting the presence of lumens while cells grown on FH were only some clusters, with most lacking lumens (FIG. 10D).

The results of this example confirm that the L1 peptide-modified fibrin hydrogel described herein can promote salivary tissue regeneration in wounded mouse submandibular glands in vitro.

Example 4

This example describes a method of promoting salivary tissue regeneration in wounded mouse submandibular glands in vivo using the L1 peptide-modified fibrin hydrogel described herein.

Figure 3:
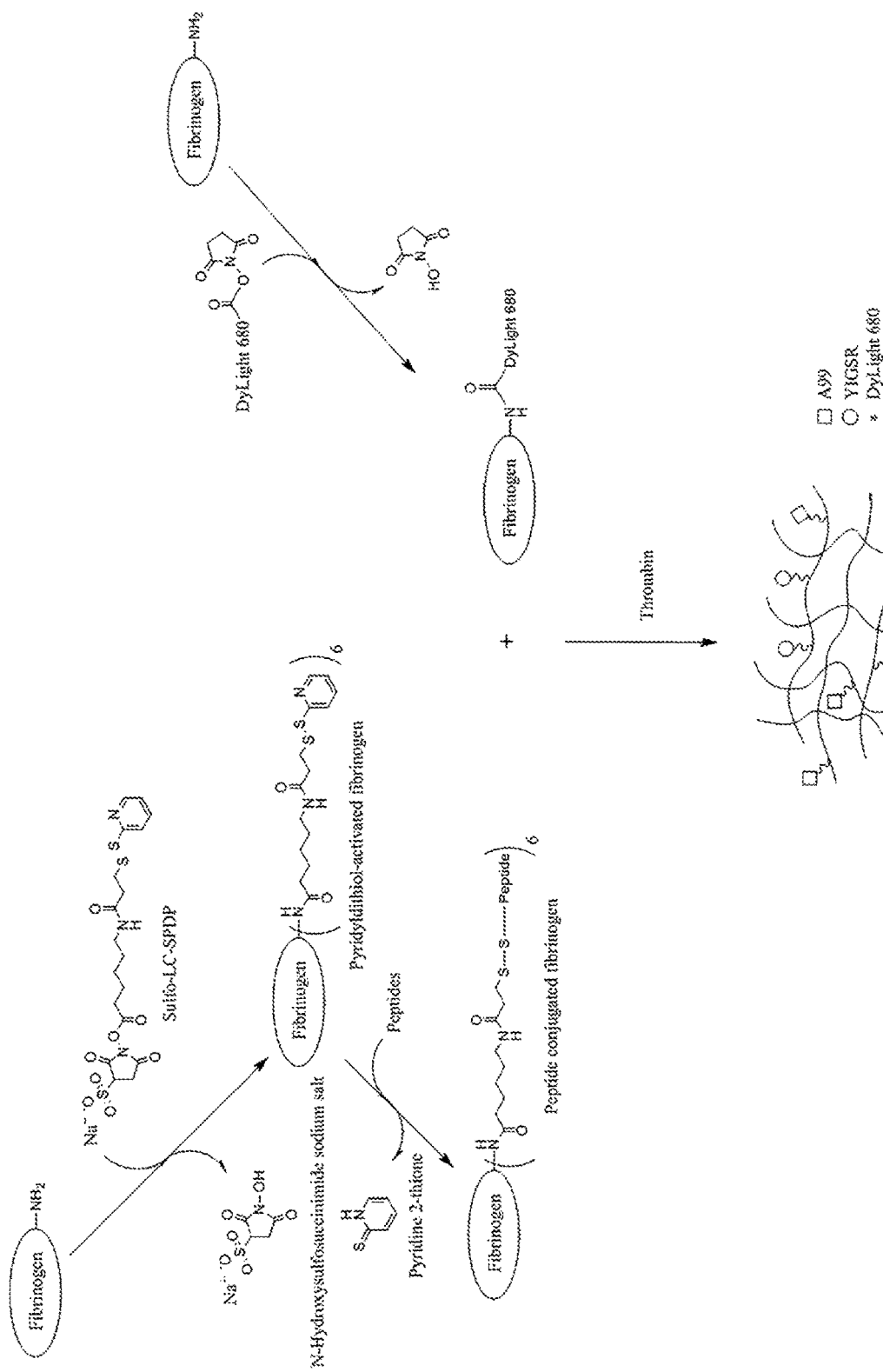
FIG. 3 is a scheme showing the synthesis of L1-peptide-conjugated fibrinogen, and the preparation of fibrin hydrogel.

To demonstrate the ability of $L_{1p}$-$FH^{680}$ to form new and functional tissue, an animal model of surgically wounded mSMG was generated. In particular, $L_{1p}$-$FH^{680}$ (DyLight 680 labeled $L_{1p}$-FH) was generated by dissolving YIGSR-conjugated fibrinogen (1.00 mg/mL) and A99-conjugated fibrinogen (1.00 mg/mL), DyLight 680 labeled fibrinogen (0.5 mg/mL) and plasma-derived bovine thrombin (2.5 U/mL) in Tris-buffered saline (TBS) with $CaCl_2$ (2.5 mM) and εACA (2 mg/mL) (FIG. 3). For the control group, $FH^{680}$ (DyLight 680 labeled FH) was fabricated by mixing fibrinogen (2 mg/mL), DyLight 680 labeled fibrinogen (0.5 mg/mL) and plasma-derived bovine thrombin (2.5 U/mL) in Tris-buffered saline (TBS) with $CaCl_2$ (2.5 mM) and εACA (2 mg/mL). Forty microliter of hydrogel mixture was then added at the wound site.

Mice were anesthetized with 3% isoflurane with an oxygen flow rate set at approximately 2.0 L/minutes. As shown in FIG. 11, a skin incision of approximately 1 cm in length was then made along the front part of the neck (panel A). Both mSMG glands were exposed and a surgical wound using a 3 mm diameter biopsy punch was created (FIG. 11, panel B). To determine the effects of $L_{1p}$-$FH^{680}$ on formation of new glandular tissue, the wound in one mSMG was filled either with $L_{1p}$-$FH^{680}$ or $FH^{680}$ while the contralateral gland was left with no scaffold, as shown in FIG. 11C. Finally, the skin incision was sutured (FIG. 11, panel D) and post-surgical studies at days 3 and 8 were performed. The number of animals used in these experiments and the times studied are summarized in Table 4.

TABLE 4

|  | None | $FH^{680}$ | $L_{1p}$-$FH^{680}$ |
|---|---|---|---|
| 3 day | 5 | 5 | 5 |
| 8 day | 5 | 5 | 5 |

Scaffold stability was monitored by measuring fluorescent signal intensity in vivo using the Xenogen IVIS 100 Bioluminescent Imager (University of Utah, Center for Quantitative Cancer Imaging) at post-surgery days 3, 8, and 20 Briefly, mice were anesthetized as described above and fluorescent images were acquired with filter set with excitation/emission at 692/712 nm. The fluorescent values were then corroborated in dissected glands using a Bio-Rad CHEMI-DOC™ MP imaging system. As shown in FIG. 11, panels E and F, fluorescent signal intensity at post-surgery day 3 (FIG. 11, panel E) is approximately 10 times higher than at post-surgery day 8 (FIG. 11, panel F). These results were corroborated by dissecting the glands measuring the fluorescent signal in a CHEMI-DOC™ MP imaging system. As shown in FIG. 11, panels G and I, both glands were visible when using bright field. In contrast, only glands filled with $L_{1p}$-$FH^{680}$ were visible under the CHEMI-DOC™ MP imaging system, as shown in FIG. 11, panels H and J.

To determine whether mSMG surgical wounds covered with $L_{1p}$-$FH^{680}$ partially induced wound healing in vivo, the mSMG sections with hematoxylin and eosin (H&E). Briefly, sections from each group were deparaffinized with xylene and rehydrated with serial ethanol solutions (100%, 70% and 50%) and distilled water. The rehydrated slides were stained with Harris hematoxylin for 6 minutes and washed for 2 minutes with distilled water, 1 minute with 0.5% Li2CO3 (w/v), and 1 minute with distilled water. Slides were washed for 1 minute with 95% ethanol, followed by a 1 minute incubation with eosin and washed for 1 minute with 95% ethanol. Finally, sections were washed three times with 100% ethanol, cleared in xylene, and mounted with a xylene-based mounting medium. The samples were examined using a Leica DMI6000B inverted microscope. As shown in FIG. 12 (panels C and G), 13 (panel A), and 14 (panel A), mSMG surgical wounds covered with $FH^{680}$ or $L_{1p}$-$FH^{680}$ displayed partial closure of the wound at post-surgery day 3. In contrast, wounded mSMG treated with no scaffold displayed empty wounded spaces at post-surgery day 3, as shown in FIG. 12 (panel E). When studying sections at day 3 at a higher magnification, mSMG surgical wounds covered with $L_{1p}$-$FH^{680}$ and $FH^{680}$ formed new blood vessels (FIGS. 15C and 15G). In contrast, wounded mSMG treated with no scaffold displayed blood clots at post-surgery day 3 (FIG. 15E, blue arrowheads).

At post-surgery day 8, mSMG surgical wounds covered with $L_{1p}$-$FH^{680}$ displayed almost complete closure of the wound, as shown in (FIG. 12, panel D and FIG. 13, panel B). In contrast, wounded mSMG treated with no scaffold only formed fibrotic tissues with incomplete wound healing, as shown in (FIG. 12, panel F). Likewise, wounded mSMG treated with $FH^{680}$ alone formed fibrotic tissue with incomplete wound healing, as shown in (FIG. 12, panel H and FIG. 14, panel B). At a higher magnification, mSMG surgical wounds covered with $L_{1p}$-$FH^{680}$ showed the presence of organized round structures with the presences of lumens indicative of acinar and ductal structures, as shown in (FIG. 15D). Conversely, wounded mSMG treated with no scaffold showed disorganized fibrotic tissue with the presence of blood clots (FIG. 15F). Additionally, wounded mSMG treated with $FH^{680}$ formed fibrotic and adipose tissues with poor wound healing (FIG. 12, panel H and FIG. 14, panel B). At post-surgery day 20, some improvement in $FH^{680}$-covered groups was also observed, as shown in FIGS. 19 and 20. As shown in FIG. 20B, mSMG surgical wounds covered with $FH^{680}$ displayed the presence of organized round structure at post-surgery day 20. However, surgical wounds covered with $FH^{680}$ (FIG. 21B) at post-surgery day 20 showed no AQP5 signal, as shown in FIG. 21B. Together, these results suggest that $L_{1p}$-$FH^{680}$ is suitable for in vivo applications and able to accelerate the mSMG wound healing process as compared to no scaffold or FH alone.

To determine whether mSMG surgical wounds covered with $L_{1p}$-$FH^{680}$ partially formed new organized conjunctive tissue, the mSMG sections were stained with Masson Trichrome stain. Specifically, the rehydrated slides were re-fixed in Bouin's solution at 60° C. for 1 hour. Slides were rinsed in running tap water for 10 minutes to remove yellow color from sections. Then, slides were washed with distilled water for 5 minutes. For nuclei staining, slides were stained in Weigert's iron hematoxylin solution for 10 minutes, rinsed with running warm tap water for 10 minutes, and washed with distilled water for 5 minutes. For cytoplasm staining, slides were incubated in Biebrich scarlet acid fuchsine solution for 5 minutes, and washed three times with distilled water for 2 minutes. For collagen staining, slides were incubated in phosphotungstic/phosphomolybdic acid for 15 minutes, transferred directly to aniline blue solution, stained for 5 minutes, and washed three times with distilled water for 2 minutes. Sections were differentiated in 1% acetic acid solution for 1 minute, washed two times with distilled water for 2 minutes. Finally, sections were dehydrated in 95% and 100% ethanol, cleared in xylene, and mounted with a xylene-based mounting medium. The samples were examined using a Leica DMI6000B imaging system. As shown in FIG. 16, panels C and G, surgical wounds covered with $L_{1p}$-$FH^{680}$ or $FH^{680}$ formed new blood vessels at post-surgery day 3 (see blue stain). In contrast, wounded mSMG treated with no scaffold displayed poor collagen formation and empty spaces (FIG. 16, panel E).

At post-surgery day 8, mSMG surgical wounds covered with $L_{1p}$-$FH^{680}$ displayed formation of new blood vessels and organized round structures (FIG. 16, panel D). In contrast, wounded mSMG treated with no scaffold only formed disorganized collagen (FIG. 16, panel F). Likewise, wounded mSMG treated with $FH^{680}$ alone formed disorganized collagen (FIG. 16, panel H).

To determine whether mSMG surgical wounds covered with $L_{1p}$-$FH^{680}$ partially formed new salivary epithelium, the mSMG sections were stained with the apical tight junction protein ZO-1 and basolateral E-cadherin. Specifically, mSMG cell clusters were fixed in 4% paraformaldehyde for 20 minutes at room temperature, incubated with 0.1% Triton X-100 in phosphate buffered saline (PBS) for 5 minutes and washed with PBS. Cells were then incubated with 5% goat serum containing 10 μM digitonin for 2 hours at room temperature and washed three times with PBS. Spheres were stained for 15 minutes with Alexa Fluor 633-conjugated phalloidin F-actin stain (1:400 dilutions in PBS; Sigma) and counter-stained with TO-PRO-3 iodide (Invitrogen) at room temperature for 15 minutes at 1:1000 dilutions and washed 3 times with PBS for 5 minutes each. Finally, specimens were analyzed using a confocal Zeiss LSM 700 microscope using a 20× objective. A total depth of 20 μm was acquired for each sample, and total projection was visualized in the xy planes.

mSMG tissue sections were immersed in 10% neutral formalin at room temperature for at least 24 hours, dehydrated in serial ethanol solutions (50%, 70% and 100% for 2 hours each), embedded in paraffin wax, and cut into 7 μm sections. Sections from each group were deparaffinized with xylene and rehydrated with serial ethanol solutions (100%, 70% and 50%). Sections were rinsed with distilled water three times, and then incubated in sodium citrate buffer (10 mM sodium citrate, 0.05% Tween 20, pH 6.0) at 95° C. for 30 minutes. Then, sections were washed with distilled water and permeabilized with 0.1% Triton X-100/PBS at room temperature for 45 minutes, blocked in 5% rabbit serum in PBS for 1 hour at room temperature, and incubated at 4° C. overnight with the following combinations of primary antibodies in 5% goat serum (1:200 dilutions unless otherwise noted): mouse-anti-E-cadherin (BD), rabbit anti-ZO-1 (Invitrogen), rabbit anti-aquaporin 5 (AQP5) (Abcam), phalloidin-Alexa 568 1:50 dilutions, rabbit anti-TMEM-16A (Abcam), rabbit anti-Von Willebrand factor (vWF), and rabbit Na$^+$/K$^+$-ATPase. Tissue sections were washed three times for five minutes with PBS and incubated for 1 hour with anti-rabbit Alexa Fluor 488 secondary antibody 1:500 dilutions (Invitrogen) and anti-mouse Alexa Fluor 568 secondary antibody 1:500 dilutions in 5% goat serum at room temperature. Sections were then washed three times with PBS for 5 minutes each, counter-stained with TO-PRO-3 Iodide (Invitrogen) at room temperature for 15 minutes at 1:1000 dilutions, and washed 3 times with PBS for 5 minutes each. Finally, specimens were analyzed using a confocal Zeiss LSM 700 microscope using a 10×objective. A total depth of 7 μm was acquired for each sample, and total projection was visualized in the xy planes.

As shown in FIG. 17 (panels A-D), surgical wounds covered with $L_{1p}$-FH$^{680}$ formed apical ZO-1 (green) and basolateral E-cadherin (red), indicative of epithelial tissue formation at post-surgery day 8. In contrast, wounded mSMG treated with no scaffold (FIG. 17, panels E-H) displayed weak ZO-1 and actin staining, indicating poor epithelial formation (see the contrast with unwounded areas, yellow-dotted areas). mSMG treated with FH$^{680}$ showed poor ZO-1 and actin staining, indicative of poor epithelial formation (FIG. 17, panels I-L).

The mSMG tissue sections also were stained with other proteins typical of salivary gland epithelium, including the water channel AQP5, the apical chloride transporter TMEM16A, the blood vessel marker Von Willebrand factor (VWF) and the basolateral Na$^+$/K$^+$-ATPase. As shown in FIG. 18, panel B, surgical wounds covered with $L_{1p}$-FH$^{680}$ showed apical TMEM16A localization (green). In contrast, wounded mSMG treated with no scaffold (FIG. 18, panel F) or FH$^{680}$ (FIG. 18, panel J) displayed no TMEM16A staining, indicating a lack of secretory epithelium in this area (see contrast with unwounded areas yellow dotted area).

When studying AQP5, it was observed that surgical wounds covered with $L_{1p}$-FH$^{680}$ (FIG. 18, panel A) showed a weak AQP5 signal (FIG. 18, panel A; see contrast with unwounded tissue, yellow dotted area). Conversely, wounded mSMG treated with no scaffold (FIG. 18, panel E) or FH$^{680}$ (FIG. 18, panel I) displayed no AQP5, indicating lack of a secretory epithelium in this area.

Surgical wounds covered with FH$^{680}$ (FIG. 21B) at post-surgery day 20 showed no AQP5 signal, as shown in FIG. 21B. Conversely, wounded mSMG treated with $L_{1p}$-FH$^{680}$ at post-surgery day 20 displayed strong AQP5 signal in acinar cell compartments and organized round structures with the presence of lumens indicative of acinar and ductal structures, as shown in FIG. 21C.

Interestingly, $L_{1p}$-FH$^{680}$-treated wounds showed basolateral Na$^+$/K$^+$-ATPase localization (FIG. 18, panel C) indicating functional epithelium. Once again, untreated or FH$^{680}$ treated wounds displayed weak Na$^+$/K$^+$-ATPase staining (FIG. 18, panels G and K), indicating poor epithelial formation (see the contrast with unwounded areas yellow dotted area). Finally, all wounds showed weak vWF staining, indicating healed tissue (FIG. 18, panels D, H and L).

The results of this example confirm that the L1 peptide-modified fibrin hydrogel described herein can repair damaged salivary tissue in vivo.

Example 5

This example demonstrates that the L1 peptide-modified fibrin hydrogel described herein promotes salivary tissue regeneration and restores salivary gland function in wounded mouse submandibular glands in vivo.

Fibrin hydrogels (FH) were prepared and conjugated to the L1 peptide ($L_{1p}$-FH) as described above. A mouse model of surgically wounded mSMG was generated as described in Example 4, and 28 mice were randomly distributed into four groups: untreated, FH treated, $L_{1p}$-FH treated and sham surgery control. A skin incision of approximately 1 cm in length was made along the anterior surface of the neck, as shown in FIG. 11, panel A. Subsequently, mSMGs were exposed and the surgical wounds were created using a 3 mm diameter biopsy punch, as shown in FIG. 11, panel B. To determine the effects of FH, 20 μL of this scaffold were added at the surgical wounds where a coverslip was placed underneath to prevent leakage, as shown in FIG. 11, panel C. The different scaffolds used in the experiments are listed in Table 5. Finally, the skin incision was sutured (see FIG. 11, panel D) and post-surgical studies at day 20 were performed.

TABLE 5

| Hydrogels | Volume Used | Composition (picomole) | | | |
|---|---|---|---|---|---|
| | | Fibrinogen | DyLight 680 | YIGSR | A99 |
| FH | 20 μL | 146.3 | 144.9 | — | — |
| $L_{1p}$-FH | 20 μL | 143.6 | 144.9 | 342.6 | 345.5 |

To monitor scaffold stability in vivo, FH were labeled with Dylight 680 and fluorescent intensity was monitored in a Xenogen IVIS 100 Bioluminescent Imager (University of Utah, Center for Quantitative Cancer Imaging) at post-surgery day 1 (FIG. 22, panel A), day 3 (FIG. 22, panel B), day 8 (FIG. 22, panel C), and day 20 (FIG. 22, panel D). Fluorescent images were acquired with a filter set using excitation/emission at 692/712 nm. As shown in FIG. 22, the fluorescent intensity of FH at day 3 (FIG. 22, panel B) was similar with the post-surgery day 1 group (FIG. 22, panel A). However, the fluorescent intensity of the FH at day 8 (FIG. 22, panel C) was approximately six times lower as compared to post-surgery day 1 or day 3 groups (FIG. 22, panels A and B). Moreover, the fluorescent intensity of FH at day 20 (FIG. 22, panel D) was undetectable. These results suggest successful attachment of FH scaffold in the wounded tissue (i.e., high stability) and likely degradation over time in vivo.

In order to monitor post-surgery body mass, mice were weighed at the start of each experiment and data was collected for 20 days. Statistical significance was assessed by two-way ANOVA ($p<0.01$) and Dunnett's post-hoc test for multiple comparisons to the untreated group. No significant weight difference was observed between untreated mice and mice treated with FH alone, as shown in FIG. 23. However, mice treated with $L_{1p}$-FH had similar weights as the sham control group, which were significantly higher as compared to untreated mice and mice treated with FH alone ($p<0.01$).

To examine saliva secretion, mice were anesthetized with ketamine (100 mg/kg) and xylazine (5 mg/kg), and injected with pilocarpine (10 mg/kg) via intraperitoneal injection to stimulate saliva secretion. Whole saliva was then collected and measured using a 200 μl pipette. Statistical significance was assessed by one-way ANOVA ($p<0.01$) and Dunnett's post-hoc test for multiple comparisons to the untreated group. As shown in FIG. 24, animals with no scaffold (untreated) or treated with FH alone displayed a significant decrease in saliva secretion rates (44% vs sham). In contrast, mice treated with $L_{1p}$-FH showed a significant increase in saliva secretion rates as compared to untreated and FH alone-treated mice. Moreover, $L_{1p}$-PH-treated mice showed increased saliva flow rates (75%), with levels close to sham controls (open incision but no surgical wound).

To determine the saliva composition of each condition, 15 μg of saliva protein from each group were fractionated by SDS-PAGE. Saliva samples were denatured at 95° C. for 5 minutes in a sample loading buffer. The denatured samples were loaded onto the Mini-PROTEAN TGX precast electrophoresis gel (Any kD™, Bio-Rad, Hercules, Calif.) and subjected to electrophoresis in 25 mM Tris/192 mM Glycine buffer with 0.1% SDS (w/v) at 100 V for 70 minutes. The electrophoresis gel was fixed in a solution of 25% ethanol, 15% formaldehyde, 60% water for 1 hour and re-fixed with 50% methanol, 40% water, and 10% glacial acetic acid for overnight. For general protein staining, the gel was stained with 0.25% Coomassie Brilliant Blue R-250 in 50% (v/v) methanol and 10% (v/v) glacial acetic acid for 1 hour and destained overnight in 20% (v/v) methanol and 10% (v/v) acetic acid. For mucin staining, the fixed gel was stained with 0.5% Alcian Blue 8GX in 2% (v/v) acetic acid for 1 hour. Then, the gel was destained overnight in 20% (v/v) methanol and 10% (v/v) acetic acid. Protein images of gels were captured using a CHEMIDOC™ mp imaging system (Bio-Rad, Hercules, Calif.). ImageJ was used to perform the image analysis. All statistical analyses were performed with GraphPad Prism 6 software (GraphPad Software Inc., La Jolla, Calif.). The total protein (see FIG. 25A) and mucin (see FIG. 25B) composition of the saliva from untreated and FH-alone treatment groups showed clearly different patterns compared to the saliva from the sham control group. The untreated group displayed a decrease in proline rich protein (15 kDa~30 kDa) and cystatin (10 kDa) levels. In addition, animals with no scaffold or with FH alone displayed a significant decrease in MUC7 ($p<0.0001$). However, the protein patterns of the $L_{1p}$-FH treated group showed comparable protein patterns to sham control (see FIG. 25C). Moreover, the ratio of MUC5B and MUC7 in the saliva slightly differed between the sham and $L_{1p}$-FH treated groups ($p=0.0111$). These results indicate that the $L_{1p}$-FH-treated SMG could produce a similar quality of saliva as compared to sham controls.

To determine whether $L_{1p}$-FH promotes tissue regeneration of mSMG surgical wounds in vivo, mSMG tissue sections were stained with hematoxylin and eosin (H&E) and picrosirius red stains. Briefly, mSMG tissue were immersed in 10% formalin at room temperature for one day, dehydrated in serial ethanol solutions (50%, 70% and 100% for 2 hours each), embedded in paraffin wax, and cut into 7 μm sections. mSMG sections from each group were deparaffinized with xylene and rehydrated with serial ethanol solutions (100%, 70%, and 50%) and distilled water. Staining with hematoxylin and eosin (H&E) and picrosirius red were performed, and tissue sections were examined using a Leica DMI6000B inverted microscope (Leica Microsystems, Wetzlar, Germany). As shown in FIG. 26, mSMG surgical wounds covered with L1p-FH displayed organized round acinar (red arrows) and ductal structures (yellow arrows) (see FIG. 26, panel C) with organized collagen formation (see FIG. 26, panel G). In contrast, wounded mSMG treated with no scaffold and FH alone formed disorganized collagen and failed to form organized round structures, as shown in FIG. 26, panels A, B, E, and F.

To verify whether mSMG surgical wounds covered with $L_{1p}$-FH regenerated salivary epithelium, mSMG sections were analyzed by confocal microscopy. Briefly, deparaffinized sections were incubated in sodium citrate buffer (10 mM sodium citrate, 0.05% Tween 20, pH 6.0) at 95° C. for 30 minutes for antigen retrieval. Sections were then washed with distilled water and permeabilized with 0.1% Triton X-100 in PBS at room temperature for 45 minutes. Sections were blocked in 5% goat serum in PBS for 1 hour at room temperature and incubated overnight at 4° C. with one of the primary antibody solutions set forth in Table 6.

TABLE 6

| Antibody Solution | Antibody | Dilutions |
|---|---|---|
| Primary Antibody Solution 1 | Rabbit anti-aquaporin 5 | 200 |
| | Mouse anti-cytokeratin 7 | 500 |
| Primary Antibody Solution 2 | Rabbit anti-TMEM-16A | 100 |
| | Mouse anti-Na$^+$/K$^+$-ATPase α antibody | 200 |
| Primary Antibody Solution 3 | Rabbit anti-PECAM-1 | 100 |
| | Mouse anti-β-tubulin III | 100 |
| Secondary Antibody Solution | Alexa Fluor 488 conjugated anti-rabbit IgG | 500 |
| | Alexa Fluor 568 conjugated anti-mouse IgG | 500 |

The following day, tissue sections were washed three times with PBS and incubated with secondary antibody solution for 1 hour at room temperature. Sections were then washed three times with PBS and counter-stained with TO-PRO-3 iodide at room temperature for 15 minutes (1:1000 dilution). Finally, tissue samples were analyzed using a confocal Zeiss LSM 700 microscope using a 20× objective. mSMG sections were stained with the following markers: aquaporin 5 (water channel protein, acinar marker), cytokeratin 7 (ductal epithelial marker), TMEM16A (apical chloride transporter), Na$^+$/K$^+$-ATPase (basolateral membrane marker), PECAM-1 (endothelial cell marker), and β-Tubulin III (neuronal cell marker). As shown in FIG. 27, the apical acinar cell marker (aquaporin 5, green) and the ductal cell marker (cytokeratin 7, red) were detected in the $L_{1p}$-FH treated group (FIG. 27, panel C) and sham control group (FIG. 27, panel D). Conversely, untreated (FIG. 27, panel A) or wounds treated with FH alone (FIG. 27, panel B) displayed very weak aquaporin 5 and disorganized cytokeratin 7 staining. Surgical wounds covered with $L_{1p}$-FH showed apical TMEM16A (green) and basolateral Na$^+$/K$^+$-ATPase localization (red) (FIG. 27, panel G) but untreated (see FIG. 27, panel E) or wounds treated with FH alone treated (see FIG. 27F) displayed very weak or no staining at all. For endothelial and neuronal markers, untreated wounds displayed poor staining (see FIG. 27I) and wounds treated with FH alone showed disorganized structure (see FIG. 27, panel J). $L_{1p}$-FH treated wounds showed endothelial marker signals and some line structure of β-tubulin III, as shown in FIG. 27, panel K.

The results of this example confirm that the L1 peptide-modified fibrin hydrogel described herein can restore salivary gland function in wounded mouse submandibular glands in vivo.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B")

is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition comprising fibrinogen conjugated to two or more peptides of laminin-111 (L1), wherein an L1 peptide comprises the amino acid sequence of CGGALRGDN-amide (SEQ ID NO: 1) and an L1 peptide comprises the amino acid sequence of CGGADPGYIGSRGAA-amide (SEQ ID NO: 2).

2. The composition of claim 1, wherein the composition comprises a fluorescent label.

3. A method of generating salivary tissue in an animal in need thereof, which method comprises administering the composition of claim 1 to an animal in need thereof, whereby salivary cells are generated in the animal.

4. The method of claim 3, wherein the animal comprises damaged salivary tissue.

5. The method of claim 3, wherein the animal is a human.

6. The method of claim 5, wherein the human suffers from hyposalivation.

7. The method of claim 5, wherein the human has Sjögren's syndrome, ectodermal dysplasia, or has undergone γ-irradiation therapy.

8. A method of repairing damaged salivary tissue, which method comprises applying the composition of claim 1 to damaged salivary tissue, whereby new salivary cells are generated and the damaged salivary tissue is repaired.

9. The method of claim 8, wherein the damaged salivary tissue is parotid gland tissue, submandibular gland tissue, or sublingual gland tissue.

10. The method of claim 8, wherein the damaged salivary tissue is mouse tissue or human tissue.

11. The method of claim 8, wherein the damaged salivary tissue is in vivo or in vitro.

12. The method of claim 11, wherein the damaged salivary tissues is in vivo.

13. The method of claim 12, wherein the damaged salivary tissue is in a human.

14. The method of claim 13, wherein the human suffers from hyposalivation.

15. The method of claim 13, wherein the human has Sjögren's syndrome, ectodermal dysplasia, or has undergone γ-irradiation therapy.

* * * * *

```
SEQUENCE LISTING

<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Cys Gly Gly Ala Leu Arg Gly Asp Asn
1               5

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Cys Gly Gly Ala Asp Pro Gly Tyr Ile Gly Ser Arg Gly Ala Ala
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Cys Gly Gly Ala Leu Arg Ala Asp Asn
1               5

<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Cys Gly Gly Ala Asp Pro Gly Ser Gly Ile Tyr Arg Gly Ala Ala
1               5                   10                  15

<210> SEQ ID NO 5
```

```
<211> LENGTH: 15
<212> TYPE: PRT
<213> ORGANISM: Artificial Sequence
<220> FEATURE:
<223> OTHER INFORMATION: Synthetic

<400> SEQUENCE: 5

Cys Gly Gly Arg Lys Arg Leu Gln Val Gln Leu Ser Ile Arg Thr
1               5                   10                  15

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Ile Lys Val Ala Val
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Tyr Ile Gly Ser Arg
1               5
```